United States Patent
Maung et al.

(10) Patent No.: US 12,384,775 B2
(45) Date of Patent: Aug. 12, 2025

(54) PYRIMID-2-YL-PYRAZOLE COMPOUNDS AS IRAK INHIBITORS

(71) Applicant: Rigel Pharmaceuticals, Inc., South San Francisco, CA (US)

(72) Inventors: Jack Maung, South San Francisco, CA (US); Yan Chen, South San Francisco, CA (US); Simon Shaw, South San Francisco, CA (US); David Sweeny, South San Francisco, CA (US); Esteban Masuda, South San Francisco, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 18/187,789

(22) Filed: Mar. 22, 2023

(65) Prior Publication Data

US 2023/0303555 A1    Sep. 28, 2023

Related U.S. Application Data

(60) Provisional application No. 63/322,955, filed on Mar. 23, 2022.

(51) Int. Cl.
C07D 417/14    (2006.01)

(52) U.S. Cl.
CPC .................................. C07D 417/14 (2013.01)

(58) Field of Classification Search
CPC .................................................... C07D 417/14
See application file for complete search history.

(56) References Cited

U.S. PATENT DOCUMENTS

| | | | |
|---|---|---|---|
| 4,738,851 A | 4/1988 | Schoenwald et al. |
| 4,882,150 A | 11/1989 | Kaufman |
| 4,921,475 A | 5/1990 | Sibalis |
| 5,008,110 A | 4/1991 | Benecke et al. |
| 5,077,033 A | 12/1991 | Viegas et al. |
| 5,087,240 A | 2/1992 | Sibalis |
| 5,088,977 A | 2/1992 | Sibalis |
| 5,163,899 A | 11/1992 | Sibalis |
| 5,164,189 A | 11/1992 | Farhadieh et al. |
| 5,254,346 A | 10/1993 | Tucker et al. |
| 5,290,561 A | 3/1994 | Farhadieh et al. |
| 5,336,168 A | 8/1994 | Sibalis |
| 5,352,456 A | 10/1994 | Fallon et al. |
| 5,403,841 A | 4/1995 | Lang et al. |
| 5,521,222 A | 5/1996 | Ali et al. |
| 5,698,219 A | 12/1997 | Valdivia et al. |
| 5,776,445 A | 7/1998 | Cohen et al. |
| 5,800,807 A | 9/1998 | Hu et al. |
| 6,056,950 A | 5/2000 | Saettone et al. |
| 6,197,934 B1 | 3/2001 | DeVore et al. |
| 6,261,547 B1 | 7/2001 | Bawa et al. |
| 7,977,477 B2 | 7/2011 | Berdini |
| 8,575,336 B2 | 11/2013 | Coe et al. |
| 8,895,544 B2 | 11/2014 | Coe et al. |
| 9,718,804 B2 | 8/2017 | Luo et al. |
| 9,732,095 B2 | 8/2017 | Gummadi et al. |
| 9,951,086 B2 | 4/2018 | Bothe et al. |
| 9,982,000 B2 | 5/2018 | Kelley et al. |
| 10,065,946 B2 | 9/2018 | Yen et al. |
| 10,208,074 B2 | 2/2019 | Kelley et al. |

(Continued)

FOREIGN PATENT DOCUMENTS

| | | |
|---|---|---|
| EP | 2 231 654 | 9/2010 |
| EP | 2 674 423 | 12/2013 |

(Continued)

OTHER PUBLICATIONS

Romagnoli . Nature. Scientific Reports 2017 7:46356 (Year: 2017).*
Berge. Journal of Pharmaceutical Sciences. 1977. 66 (1). 1-19) (Year: 1977).*
"5-Thiazolecarboxamide, 4-methyl-1-N-[2-(4-morpholinyl)-6-benzothiazolyl]-2-(2-pyridinyl)" *Chemical Library Document from STN*, Apr. 2007.
Buckley et al., "IRAK-4 inhibitors. Part 1: A series of amides," *Bioorganic & Medicinal Chemistry Letters* 18:3211-3214, available online Apr. 26, 2008.
CAS Registry No. 1376284-17-1 dated Jun. 7, 2012.

(Continued)

*Primary Examiner* — Brandon J Fetterolf
*Assistant Examiner* — Jerica Katlynn Wilson
(74) *Attorney, Agent, or Firm* — Jones Day

(57) ABSTRACT

Disclosed embodiments concern novel interleukin receptor associated kinases (IRAK) inhibitor compounds and compositions comprising such compounds. The compounds may have a structure according to Formula I Formula I

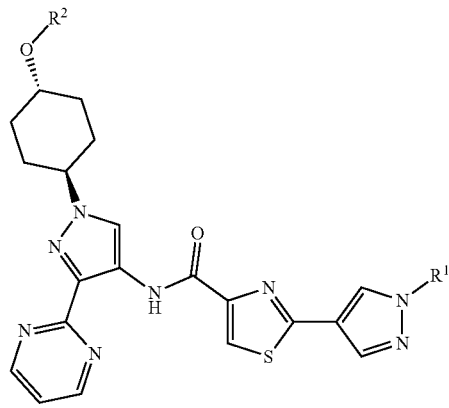

Also disclosed are methods of making and using the compounds and compositions. The disclosed compounds and/or compositions may be used to treat or prevent an IRAK-associated disease or condition.

22 Claims, No Drawings

(56) References Cited

U.S. PATENT DOCUMENTS

| | | |
|---|---|---|
| 10,208,075 B2 | 2/2019 | Kelley et al. |
| 10,370,367 B2 | 8/2019 | Li et al. |
| 10,414,753 B2 | 9/2019 | Tso et al. |
| 10,590,121 B2 | 3/2020 | Taylor et al. |
| 10,774,076 B2 | 9/2020 | Yen et al. |
| 10,941,140 B2 | 3/2021 | Li et al. |
| 10,947,216 B2 | 3/2021 | Tso et al. |
| 11,059,814 B2 | 7/2021 | Taylor et al. |
| 11,299,486 B2 | 4/2022 | Yen et al. |
| 11,370,787 B2 | 6/2022 | Chou et al. |
| 11,492,349 B2 | 11/2022 | Li et al. |
| 11,530,194 B2 | 12/2022 | Tso et al. |
| 2011/0251176 A1 | 10/2011 | Wang |
| 2014/0088117 A1 | 3/2014 | Burch |
| 2016/0068543 A1 | 3/2016 | Greenwood et al. |

FOREIGN PATENT DOCUMENTS

| | | | |
|---|---|---|---|
| WO | WO 2004/037248 | 5/2004 | |
| WO | WO 2006/070198 | 7/2006 | |
| WO | WO 2006/070202 | 7/2006 | |
| WO | WO 2009/054468 | 4/2009 | |
| WO | WO 2010/121243 | 10/2010 | |
| WO | WO 2010/121834 | 10/2010 | |
| WO | WO 2011/043371 | 4/2011 | |
| WO | WO 2011/124580 | 10/2011 | |
| WO | WO 2012/068546 | 5/2012 | |
| WO | WO 2012/072685 | 6/2012 | |
| WO | WO 2012/084704 | 6/2012 | |
| WO | WO 2012/097013 | 7/2012 | |
| WO | WO 2013/042137 | 3/2013 | |
| WO | WO 2013/045461 | 4/2013 | |
| WO | WO 2013/106535 | 7/2013 | |
| WO | WO 2014/058691 | 4/2014 | |
| WO | WO 2014/121931 | 8/2014 | |
| WO | WO 2014/121942 | 8/2014 | |
| WO | WO 2015/048281 | 4/2015 | |
| WO | WO 2015/068856 | 5/2015 | |
| WO | WO 2015/069594 | 5/2015 | |
| WO | WO 2015/089481 | 6/2015 | |
| WO | WO 2015/104662 | 7/2015 | |
| WO | WO 2015/106058 | 7/2015 | |
| WO | WO 2016/081679 | 5/2016 | |
| WO | WO 2016/172560 | 10/2016 | |
| WO | WO-2016172560 A1 * | 10/2016 | ......... A61K 31/4155 |
| WO | WO 2017/009798 | 1/2017 | |
| WO | WO 2017/023941 | 2/2017 | |
| WO | WO 2018/081294 | 5/2018 | |
| WO | WO 2018/089199 | 5/2018 | |
| WO | WO-2018089199 A1 * | 5/2018 | ............. A61P 29/00 |
| WO | WO 2019/006126 | 1/2019 | |
| WO | WO 2021/041898 | 3/2021 | |

OTHER PUBLICATIONS

Chaudhary et al., "Recent Advances in the Discovery of Small Molecule Inhibitors of Interleukin-1 Receptor-Associated Kinase (IRAK4) as a Therapeutic Target for Inflammation and Oncology Disorders," *Journal of Medical Chemistry* 58(1):96-110, Jan. 8, 2015.

Dussiau et al., "Targeting IRAK1 in T-Cell acute lymphoblastic leukemia," *Oncotarget* 6(22):18956-18965, Jun. 1, 2015.

Hirose et al., "Multidrug resistance in hematological malignancy," *The Journal of Medical Investigation* 50:126-135, 2003.

Jain et al., "IL-1 receptor-associated kinase signaling and its role in inflammation, cancer progression, and therapy resistance," *Frontiers in Immunology* vol. 5, Article 553, pp. 1-8, Nov. 17, 2014.

Lim et al., "Discovery of 5-Amino-N-(1H-pyrazol-4-yl)pyrazolo[1,5-α]pyrimidine- 3-carboxamide Inhibitors of IRAK4," *ACS Medicinal Chemistry Letters* 6(6):683-688, 2015.

Markovtsov et al., "Abstract 346: Potential role for R191, potent and selective IRAK4 kinase inhibitor, in treatment of hematologic malignancies," AACR 107th Annual Meeting 2016, vol. 76, No. 14, Supplement, Apr. 16-20, 2016, New Orleans, LA.

Patra et al., "Recent Progress in the Molecular Recognition and Therapeutic Importance of Interleukin-1 Receptor-Associated Kinase 4," *Molecules* 21(11):1529-1543, 2016.

Pourbasheer et al., "Quantitative structure-activity relationship (QSAR) study of interleukin-1 receptor associated kinase 4 (IRAK-4) inhibitor activity by the genetic algorithm and multiple linear regression (GA-MLR) method," *Journal of Enzyme Inhibition and Medicinal Chemistry* 5(6):844-853, 2010.

Rhyasen et al., "Targeting IRAK1 as a Therapeutic Approach for Myelodysplastic Syndrome," *Cancer Cell* 24:90-104, Jul. 8, 2013.

Rhyasen et al., "IRAK signalling in cancer," *British Journal of Cancer* 112:232-237, 2015, published online Oct. 7, 2014.

Singer et al., "Inhibition of interleukin-1 receptor-associated kinase 1 (IRAK1) as a therapeutic strategy," *Oncotarget* 9(70):33416-33439, 2018.

Unbekandt et al., "A novel small-molecule MRCK inhibitor cancer cell invasion," *Cell Communication and Signaling* 12(54):1-15, 2014.

Wang et al., "IRAK-4 Inhibitors for Inflammation," *Current Topics in Medical Chemistry* 9:724-737, 2009.

\* cited by examiner

PYRIMID-2-YL-PYRAZOLE COMPOUNDS AS IRAK INHIBITORS

CROSS REFERENCE TO RELATED APPLICATION

This application claims the benefit of the earlier filing date of U.S. provisional patent application No. 63/322,955, filed Mar. 23, 2022, which is incorporated herein by reference in its entirety.

FIELD

This disclosure concerns pyrazole compounds, and embodiments of a method for making and using the compounds, such as for inhibiting interleukin receptor-associated kinase (IRAK), and for treating diseases and conditions related to IRAK.

BACKGROUND

Interleukin-1 receptor-associated kinases (IRAKs) are important mediators of signaling processes, such as toll-like receptors (TLR) and interleukin-1 receptor (IL-1R) signaling processes. IRAKs have been implicated in modulating signaling networks that control inflammation, apoptosis, and cellular differentiation. Four IRAK genes have been identified in the human genome (IRAK1, IRAK2, IRAK3 and IRAK4), and studies have revealed distinct, non-redundant biological roles. IRAK1 and IRAK4 have been shown to exhibit kinase activity.

SUMMARY

Disclosed herein are embodiments of a compound having a structure according to Formula I or a pharmaceutically acceptable salt or solvate thereof:

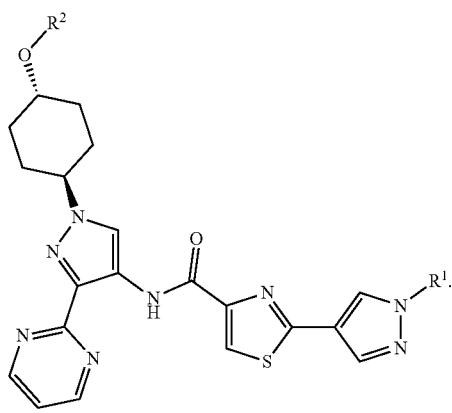

Formula I

With respect to Formula I, $R^1$ is H, aliphatic, acyl, heterocyclyl, carboxyl ester, amide, alkyl phosphoramidate, or alkyl phosphate, such as H, alkyl, or -alkylOP(O)(OR)$_2$, for example, —CH(CH$_3$)OP(O)(OR)$_2$ or —CH$_2$OP(O)(OR)$_2$, where each OR is —OH, —Oalkyl, —Oaryl, —Oheteroaryl, —Oaralkyl, or —O$^-$M$^+$ where M$^+$ is a counter ion with a single positive charge, and $R^2$ is C$_{1-6}$alkyl. In some embodiments, $R^2$ is C$_{1-4}$alkyl. In some embodiments, the compound has a structure according to Formula II, or a pharmaceutically acceptable salt or solvate thereof.

In one embodiment, $R^1$ is H. In another embodiment, $R^1$ is C$_{1-6}$alkyl. In a further embodiment, $R^1$ is —CH$_2$OP(O)(OR)$_2$, and may be —CH$_2$OP(O)(OH)$_2$, —CH$_2$OP(O)(OC$_{1-6}$alkyl)$_2$, or —CH$_2$OP(O)(O$^-$M$^+$)$_2$, such as —CH$_2$OP(O)(O$^-$Na$^+$)$_2$. In a further embodiment, $R^1$ is —CH(CH$_3$)OP(O)(OR)$_2$, and may be —CH(CH$_3$)OP(O)(OH)$_2$, —CH(CH$_3$)OP(O)(OC$_{1-6}$alkyl)$_2$, or —CH(CH$_3$)OP(O)(O$^-$M$^+$)$_2$, such as —CH(CH$_3$)OP(O)(O$^-$Na$^+$)$_2$.

The compound may be in a free base form, or a salt form, such as a co-crystal form, for example, a tartaric acid salt co-crystal or a tris salt co-crystal.

Also disclosed herein is a pharmaceutical composition comprising a compound disclosed herein, and a pharmaceutically acceptable excipient.

A method for inhibiting an IRAK enzyme is disclosed herein. The method may comprise contacting the enzyme with an effective amount of a compound disclosed herein. In some embodiments, contacting the enzyme comprises administering the compound to a subject.

Also disclosed herein is a method for treating a subject for a disease or condition wherein an IRAK inhibitor is indicated. The method may comprise administering to the subject an effective amount of a compound disclosed herein, or a pharmaceutical composition thereof. The disease or condition may comprise an auto-immune disease, inflammatory disorder, cardiovascular disease, neurodegenerative disorder, allergic disorder, multi-organ failure, kidney disease, platelet aggregation, a hyperproliferative disorder, transplantation, sperm motility, erythrocyte deficiency, graft rejection, lung injury, respiratory disease, ischemic condition, bacterial infection, viral infection, immune regulatory disorder or a combination thereof. In some embodiments, the disease or condition comprises aplastic anemia, atopic dermatitis, pustular psoriasis, palmoplantar pustulosis, primary biliary cirrhosis, pyoderma, sclerosing cholangitis, systemic juvenile idiopathic arthritis, hidradenitis suppurativa, cytokine release syndrome, or myelodysplastic syndromes (MDS).

In some embodiments, the disease or condition comprises a lymphoid neoplasm. The lymphoid neoplasm may be selected from myeloproliferative neoplasms (MPN) excluding polycythemia vera, myeloid/lymphoid neoplasms with PDGFRA rearrangement, myeloid/lymphoid neoplasms with PDGFRB rearrangement, myeloid/lymphoid neoplasms with FGFR1 rearrangement, myeloid/lymphoid neoplasms with PCM1-JAK2, myelodysplastic/myeloproliferative neoplasms (MDS/MPN), myeloid sarcoma, myeloid proliferations related to Down syndrome, blastic plasmacytoid dendritic cell neoplasm, B-lymphoblastic leukemia/lymphoma; and/or T-lymphoblastic leukemia/lymphoma. In some embodiments, the lymphoid neoplasm is a myeloproliferative neoplasm selected from chronic myeloid leukemia (CML), chronic neutrophilic leukemia (CNL), primary myelofibrosis (PMF), essential thrombocythemia, chronic eosinophilic leukemia, or a combination thereof. in certain embodiments, the lymphoid neoplasm is chronic myeloid leukemia.

In any embodiments, the method may further comprise identifying the subject having from the lymphoid neoplasm. In certain embodiments, the lymphoid neoplasm is chronic myelomonocytic leukemia and identifying the subject comprises identifying a subject having a persistent peripheral blood monocytosis of ≥1×10$^9$/L and monocytes accounting for ≥10% of the white blood cell (WBC) differential count, and rearrangements in the PDGFRA, PDGFRB or FGFR1 genes and the PCM1-JAK2 fusion gene are not observed.

The foregoing and other objects, features, and advantages of the technology will become more apparent from the following detailed description.

DETAILED DESCRIPTION

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include hydrogen so that each carbon conforms to a valence of four. For example, in the structure on the left-hand side of the schematic below there are nine hydrogen atoms implied. The nine hydrogen atoms are depicted in the right-hand structure.

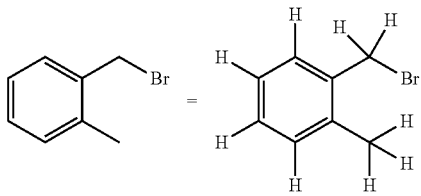

Sometimes a particular atom in a structure is described in textual formula as having a hydrogen or hydrogen atoms, for example —$CH_2CH_2$—. It will be understood by a person of ordinary skill in the art that the aforementioned descriptive techniques are common in the chemical arts to provide brevity and simplicity to description of organic structures.

A person of ordinary skill in the art will appreciate that the definitions may be combined to further describe a particular compound. For example, hydroxyaliphatic refers to an aliphatic group substituted with an hydroxy (—OH) group, and haloalkylaryl refers to an aryl group substituted with an alkyl group, where the alkyl group too is substituted with a halogen, and where the point of attachment to the parent structure is via the aryl moiety since aryl is the base name of the substituent.

As used herein, the term "substituted" refers to all subsequent modifiers in a term, for example in the term "substituted aryl$C_{1-8}$alkyl," substitution may occur on the "$C_{1-8}$alkyl" portion, the "aryl" portion or both portions of the aryl$C_{1-8}$alkyl group. Also by way of example, alkyl includes substituted cycloalkyl groups.

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted. In particular embodiments, the substituent may or may not be expressly defined as substituted, but is still contemplated to be optionally substituted. For example, an "alkyl" substituent may be unsubstituted or substituted, but an "unsubstituted alkyl" may not be substituted.

In one embodiment, a group that is substituted has 1 substituent, 2 substituents, substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(heteroaryl-1)-(heteroaryl-2)-(heteroaryl-3), heteroaryl-3 can only be substituted with substituents that are not themselves substituted.

"Aliphatic" refers to a substantially hydrocarbon-based group or moiety, including alkyl, alkenyl, alkynyl groups, cyclic versions thereof, such as cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms; for example, from one to fifteen, from one to ten, from one to six, or from one to four carbon atoms, and a cyclic aliphatic contains from three to twenty-five carbon atoms; for example, from three to fifteen, from three to ten, from three to six, or from three to four carbon atoms.

"Acyl" refers to the group —C(O)R, where R is H, aliphatic, heteroaliphatic, heterocyclic or aryl. Exemplary acyl moieties include, but are not limited to, —C(O)H, —C(O)alkyl, —C(O)$C_1$-$C_6$alkyl, —C(O)$C_1$-$C_6$haloalkyl-C(O)cycloalkyl, —C(O)alkenyl, —C(O)cycloalkenyl, —C(O)aryl, —C(O)heteroaryl, or —C(O)heterocyclyl. Specific examples include, —C(O)H, —C(O)Me, —C(O)Et, or —C(O)cyclopropyl.

"Alkyl" refers to a saturated aliphatic hydrocarbyl group having from 1 to 25 carbon atoms, typically 1 to 10 carbon atoms such as 1 to 6 carbon atoms ($C_1$-$C_6$alkyl). An alkyl moiety may be substituted or unsubstituted. This term includes, by way of example, linear and branched hydrocarbyl groups, cycloalkyl groups, and combinations thereof, such as a —$CH_2$cyclopropyl group, unless otherwise specified. Cycloalkyl refers to a cyclic aliphatic group having from 3 to 15 carbon atoms, typically, from 3 to 8 carbon atoms, from 3 to 6 carbon atoms or from 3 to 4 carbon atoms. A cycloalkyl group may be a single ring (e.g., cyclohexyl), or may comprise multiple rings, such as in a fused, bridged or spirocyclic system, at least one of which is aliphatic, provided that the point of attachment is through an atom of an aliphatic region of the cycloalkyl group. Example alkyl groups include, but are not limited to methyl ($CH_3$), ethyl (—$CH_2CH_3$), n-propyl (—$CH_2CH_2CH_3$), isopropyl (—$CH(CH_3)_2$), n-butyl (—$CH_2$—$CH_2CH_2CH_3$), isobutyl (—$CH_2CH_2(CH_3)_2$), sec-butyl (—$CH(CH_3)(CH_2CH_3)$), t-butyl (—$C(CH_3)_3$), n-pentyl (—$CH_2CH_2CH_2CH_2CH_3$), neopentyl (—$CH_2C(CH_3)_3$), cyclopropyl, cyclopropyl, cyclobutyl, cyclopentyl, cyclohexyl, cycloheptyl, —$CH_2$cyclopropyl, —$CH_2$cyclobutyl, —$CH_2$cyclopentyl, or —$CH_2$cyclohexyl.

"Amide" refers to the group —N(H)acyl, or —C(O) amino.

"Araliphatic" refers to an aryl group attached to the parent via an aliphatic moiety. Araliphatic includes aralkyl or arylalkyl groups such as benzyl and phenylethyl.

"Aralkyl" refers to an aryl group attached to the parent via an alkyl moiety. Aralkyl includes groups such as benzyl and phenylethyl.

"Aryl" refers to an aromatic group of, unless specified otherwise, from 5 to 15 ring atoms having a single ring (e.g., phenyl) or multiple fused rings in which at least one ring is aromatic (e.g., naphthyl). For groups having multiple rings, at least one of which is aromatic and one is not, such groups are nevertheless referred to as "aryl" provided that the point of attachment to the remainder of the compound is through an atom of an aromatic portion of the aryl group. Aryl groups may be monocyclic, bicyclic, tricyclic or tetracyclic. Unless otherwise stated, an aryl group may be substituted or unsubstituted.

"Carboxyl," "carboxy" or "carboxylate" refers to —$CO_2H$, —C(O)O— or salts thereof.

"Carboxyl ester" or "carboxy ester" refers to the group —C(O)OR, where R is aliphatic, heteroaliphatic, and heterocyclic, including aryl and heteroaryl.

"Cycloaliphatic" refers to a cyclic aliphatic group having a single ring (e.g., cyclohexyl), or multiple rings, such as in a fused, bridged or spirocyclic system, at least one of which is aliphatic, provided that the point of attachment is through an atom of an aliphatic region of the cycloaliphatic group. Cycloaliphatic includes saturated and unsaturated systems, including cycloalkyl, cycloalkenyl and cycloalkynyl. Exemplary cycloaliphatic groups include, but are not limited to, cyclopropyl, cyclobutyl, cyclopentyl, cyclohexyl, cycloheptyl, cyclopentenyl, or cyclohexenyl.

"Halo," "halide" or "halogen" refers to fluoro, chloro, bromo or iodo.

"Haloalkyl" refers to an alkyl moiety substituted with one or more halogens. An exemplary haloalkyl moiety is $CF_3$.

"Heterocyclyl," and "heterocycle" refer to aromatic and non-aromatic ring systems, and more specifically refer to a stable three- to fifteen-membered ring moiety comprising carbon atoms and at least one, such as from one to five heteroatoms. The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and the nitrogen, phosphorus, carbon, silicon or sulfur atoms in the heterocyclyl moiety can be optionally oxidized to various oxidation states. For convenience, nitrogens, particularly but not exclusively, those defined as annular aromatic nitrogens, are meant to include their corresponding N-oxide form, although not explicitly defined as such in a particular example. In addition, annular nitrogen atoms can be optionally quaternized. Heterocycle includes heteroaryl or aromatic heterocyclyl moieties, and nonaromatic heterocyclyl moieties, which are heterocyclyl rings which are partially or fully saturated, such as heterocycloalkyl.

"Heteroaryl" refers to an aromatic group or moiety of, unless specified otherwise, from 5 to 15 ring atoms comprising at least one carbon atom and at least one heteroatom, such as N, S, O, P, or Si. A heteroaryl group or moiety may comprise a single ring (e.g., pyridinyl, pyrimidinyl or pyrazolyl) or multiple condensed rings (e.g., indolyl, benzopyrazolyl, or pyrazolopyridinyl). Heteroaryl groups or moiety may be, for example, monocyclic, bicyclic, tricyclic or tetracyclic. Unless otherwise stated, a heteroaryl group or moiety may be substituted or unsubstituted.

"Heterocycloalkyl," refer to a stable three- to fifteen-membered non-aromatic ring moiety comprising at least one carbon atom, and typically plural carbon atoms, and at least one, such as from one to five, heteroatoms. The heteroatom(s) may be nitrogen, phosphorus, oxygen, silicon or sulfur atom(s). The heterocycloalkyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and any nitrogen, phosphorus, carbon, silicon or sulfur atoms in the heterocycloalkyl moiety can be optionally oxidized to various oxidation states, unless expressly excluded or excluded by context. For convenience, nitrogens, particularly, but not exclusively, those defined as annular aromatic nitrogens, are meant to include their corresponding N-oxide form, although not explicitly defined as such in a particular example. In addition, annular nitrogen atoms can be optionally quaternized.

Examples of heterocycloalkyl groups include, but are not limited to, tetrahydroisoquinolyl, piperidinyl, piperazinyl, 2-oxopiperazinyl, 2-oxopiperidinyl, pyrrolidinyl, 4-piperidonyl, dihydropyridinyl, tetrahydropyridinyl, morpholinyl, diazabicycloheptane, diazapane, diazepine, tetrahydrofuryl, and tetrahydropyranyl.

"Phosphate" refers to the group —O—P(O)(OR')$_2$, where each —OR' independently is —OH, —O-aliphatic, such as —O-alkyl, —O-aryl, or —O-aralkyl, or —OR' is —$O^-M^+$, where $M^+$ is a counter ion with a single positive charge as disclosed herein. For example, each $M^+$ may be an alkali ion, such as $K^+$, $Na^+$, $Li^+$; an ammonium ion, such as $^+N(R'')_4$ where each R" independently is H, aliphatic, such as alkyl, hydroxyalkyl, or a combination thereof, heterocyclyl, or aryl; an amino acid, such as arginine or lysine; an amino sugar, such as meglumine; or an alkaline earth ion, such as $[Ca^{2+}]_{0.5}$, $[Mg^{2+}]_{0.5}$, or $[Ba^{2+}]_{0.5}$. Alkyl phosphate refers to the group -alkyl-phosphate, such as, —$CH_2O$—P(O)(OR')$_2$ or —$CH_2(CH_3)O$—P(O)(OR')$_2$ for example, —$CH_2OP(O)$(O-isopropyl)$_2$, —$CH_2OP(O)(OH)$(O-tert-butyl), —$CH_2OP(O)$(O-tert-butyl)$_2$, —$CH_2OP(O)(OCH_2OCO_2$isopropyl)$_2$, —$CH_2OP(O)(OH)_2$, or a salt thereof, such as —$CH_2OP(O)(O^-Na^+)_2$, —$CH_2OP(O)(O^-)_2Mg^{2+}$, or —$CH_2OP(O)(OH)(O^-Na^+)$ "Phosphoramidate" refers to the group —O—P(O)(OR') (N(R')$_2$), where each R' independently is H, aliphatic, such as alkyl, aryl, or aralkyl, or —OR' is —$O^-M^+$, and where $M^+$ is a counter ion with a single positive charge, as disclosed herein. For example, each $M^+$ may be an alkali ion, such as $K^+$, $Na^+$, $Li^+$; an ammonium ion, such as $^+N(R'')_4$ where each R" independently is H, aliphatic, such as alkyl, hydroxyalkyl, or a combination thereof, heterocyclyl, or aryl; an amino acid, such as arginine or lysine; an amino sugar, such as meglumine; or an alkaline earth ion, such as $[Ca^{2+}]_{0.5}$, $[Mg^{2+}]_{0.5}$, or $[Ba_{2+}]_{0.5}$. Alkyl phosphoramidate refers to the group -alkyl-phosphoramidate, such as, for example, —CH$_2$O—P(O)(OR')(N(R'$_2$)) or —CH$_2$(CH$_3$)O—P(O)(OR')(N(R'$_2$)), such as, —CH$_2$OP(O)(O-phenyl)[NHC(CH$_3$)CO$_2$isopropyl], or —CH$_2$OP(O)(OH)(N(H)alkyl), or a salt thereof, such as —CH$_2$OP(O)(O$^-$Na$^+$)(N(H)alkyl).

"Patient" or "Subject" refers to mammals and other animals, particularly humans. Thus the disclosed methods are applicable to both human therapy and veterinary applications.

"Pharmaceutically acceptable excipient" refers to a substance, other than the active ingredient, that is included in a formulation of the active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is an excipient that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as Freund's complete adjuvant or Freund's incomplete adjuvant.

"Pharmaceutically acceptable carrier" refers to an excipient that is a carrier or vehicle, such as a suspension aid, solubilizing aid, or aerosolization aid. *Remington: The Science and Practice of Pharmacy*, The University of the Sciences in Philadelphia, Editor, Lippincott, Williams, & Wilkins, Philadelphia, PA, 21$^{st}$ Edition (2005), incorporated herein by reference, describes exemplary compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as formic acid, acetic acid, adipic acid, aspartic acid, trifluoroacetic acid, propionic acid, gentisic acid, glycolic acid, pyruvic acid, oxalic acid, maleic acid, malic acid, malonic acid, succinic acid, fumaric acid, tartaric acid, citric acid, benzoic acid, cinnamic acid, mandelic acid, benzene sulfonic acid, isethionic acid, lactic acid, methanesulfonic acid, ethanesulfonic acid, naphthalene-1,5-disulfonic acid, naphthalene-2-sulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, tris(hydroxymethyl)aminomethane (Tris), ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.) In particular disclosed embodiments, the pyrazole compound may be a formate or sodium salt.

"Effective amount" with respect to a compound or composition refer to an amount of the compound or composition sufficient to achieve a particular desired result, such as to inhibit a protein or enzyme, particularly an interleukin-1 receptor-associated kinase; to elicit a desired biological or medical response in a tissue, system, subject or patient; to treat or prevent a specified disorder or disease; to ameliorate or eradicate one or more of its symptoms; and/or to prevent the occurrence of the disease or disorder. The amount of a compound which constitutes an "effective amount" may vary depending on the compound, the desired result, the disease state and its severity, the age of the patient to be treated, and the like.

"Solvate" refers to a complex formed by combination of solvent molecules with molecules or ions of a solute. The solvent can be an organic solvent, an inorganic solvent, or a mixture of both. Exemplary solvents include, but are not limited to, alcohols, such as methanol, ethanol, propanol; amides such as N,N-dialiphatic amides, such as N,N-dimethylformamide; tetrahydrofuran; alkylsulfoxides, such as dimethylsulfoxide; water; and combinations thereof. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

"Treating" or "treatment" as used herein concerns treatment of a disease or condition of interest in a patient or subject, particularly a human having the disease or condition of interest, and includes by way of example, and without limitation:
  (i) inhibiting the disease or condition, for example, arresting or slowing its development;
  (ii) relieving the disease or condition, for example, causing regression of the disease or condition or a symptom thereof; or
  (iii) stabilizing the disease or condition.

"Preventing" as used herein concerns preventing the disease or condition from occurring in a patient or subject, in particular, when such patient or subject is predisposed to the condition but has not yet been diagnosed as having it.

As used herein, the terms "disease," "disorder" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

The above definitions and the following general formulas are not intended to include impermissible substitution patterns (e.g., methyl substituted with 5 fluoro groups). Such impermissible substitution patterns are easily recognized by a person having ordinary skill in the art.

Any of the groups referred to herein may be optionally substituted by at least one, possibly two or more, substituents as defined herein. That is, a substituted group has at least one, possible two or more, substitutable hydrogens replaced by a substituent or substituents as defined herein, unless the context indicates otherwise or a particular structural formula precludes substitution.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diastereomers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, it would be understood that the disclosed compounds encompass any tautomeric, conformational isomeric, optical isomeric, and/or geometric isomeric forms of the compounds described herein, as well as mixtures of these various different isomeric forms. In cases of limited rotation, e.g. around the amide bond or between two directly attached rings such as the pyrazole and pyridinyl rings, atropisomers are also possible and are also specifically included in the compounds of the disclosure.

Particular examples of the presently disclosed compounds include one or more asymmetric centers; thus these compounds can exist in different stereoisomeric forms. Accordingly, compounds and compositions may be provided as individual pure enantiomers or diastereomers, or as stereoisomeric mixtures, including racemic mixtures. In certain embodiments the compounds disclosed herein are synthesized in or are purified to be in substantially enantiopure form, such as in at least 90% enantiomeric excess, 95% enantiomeric excess, 97% enantiomeric excess, 98% enantiomeric excess, 99% enantiomeric excess, 99.5% enantiomeric excess, or greater than 99.5% enantiomeric excess, such as in enantiopure form.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl may be $C_2H_5$ or $C_2H_5$ where from 1 to 5 hydrogens are replaced by deuterium.

II. Compounds

Disclosed herein are compounds, methods of making the compounds, and methods of using the compounds. In one embodiment, the disclosed compounds are kinase inhibitors, particularly tyrosine kinase inhibitors. In a particular embodiment the compounds are useful in blocking one or more cytokine signaling pathways, such as the IL-17 signaling pathway. For certain embodiments, the disclosed compounds are useful for treating conditions in which inhibition of an interleukin-1 receptor-associated kinase (IRAK) pathway is therapeutically useful. In some embodiments, the compounds directly inhibit an IRAK protein, such as IRAK1, IRAK2, IRAK3 and/or IRAK4.

Exemplary compounds within the scope of the present disclosure have a general Formula I Formula I

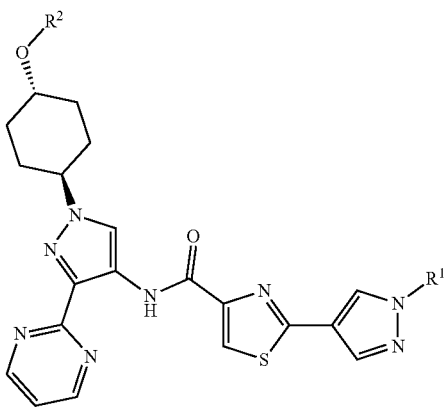

or a pharmaceutically acceptable salt or solvate thereof.

With respect to Formula I, $R^1$ is H, aliphatic, acyl, heterocyclyl, carboxyl ester, amide, alkyl phosphoramidate, or alkyl phosphate. In some embodiments, $R^1$ is not H, or alternatively, $R^1$ is hydrogen. When $R^1$ is hydrogen the compound may be a free base or in the form of a salt. In other embodiments, $R^1$ is alkyl, acyl, carboxyl ester, amide, nonaromatic heterocyclyl, alkyl phosphoramidate, or alkyl phosphate. A person of ordinary skill in the art understands that compounds where $R^1$ is not H may act a prodrug of the compound where $R^1$ is H, for example, when administered to a subject.

$R^2$ is $C_{1-6}$alkyl, such as $C_{1-4}$alkyl.

In some embodiments, $R^2$ is ethyl.

In some embodiments, $R^1$ is H, $C_{1-4}$alkyl phosphate, $C_{1-4}$alkyl phosphoramidate, $C_{1-6}$alkyl, $C_{1-6}$acyl, —C(O)O—$C_{1-6}$aliphatic, —C(O)N($R^b$)$_2$, or 5- or 6-membered nonaromatic heterocyclyl, but in certain embodiments, $R^1$ is not H, or $R^1$ is H and the compound is a salt.

With respect to the $R^1$ moiety, the $C_{1-6}$alkyl moiety may be unsubstituted, or it may be substituted, such as with a 5- or 6-membered nonaromatic heterocyclyl, OH, —OC(O)—$R^a$, —N($R^b$)$_2$, —OC(O)—$R^c$, carboxyl, or a combination thereof;

the $C_{1-6}$acyl moiety may be unsubstituted or it may be substituted with —C(O)O—$C_{1-4}$alkyl, —C(O)O—$C_{1-4}$alkyl-N($R^b$)$_2$, N($R^b$)$_2$, —NHC(O)$C_{1-4}$alkyl, or a combination thereof;

the 5- or 6-membered heterocyclyl moiety may be a 5- or 6-membered oxygen-containing heterocyclyl, and/or may be substituted with hydroxyl, hydroxymethyl, or a combination thereof; or the —C(O)O—$C_{1-6}$aliphatic may be —C(O)O—$C_{1-6}$alkyl optionally substituted with —OC(O)$C_{1-4}$alkyl, or N($R^b$)$_2$, or the —C(O)O—$C_{1-6}$aliphatic may be —C(O)O—$C_{3-6}$ cycloalkyl optionally substituted with $C_{1-4}$alkyl.

In any embodiments, each $R^a$ independently is 5-membered nonaromatic heterocyclyl, aryl substituted with —CH$_2$N($R^b$)$_2$, $C_{3-6}$cycloalkyl substituted with carboxyl, $C_{1-6}$alkoxy, unsubstituted $C_{1-6}$alkyl, or $C_{1-6}$alkyl substituted with one or more, such as 1, 2 or 3, of N($R^b$)$_2$, carboxyl, carboxyl ester, —OC$_{1-6}$acyl, —NHC(O)(NH$_2$)$C_{1-6}$alkyl, or —(OCH$_2$CH$_2$)$_{1-8}$N($R^b$)$_2$;

each $R^b$ independently is H, unsubstituted $C_{1-6}$alkyl, $C_{1-6}$alkyl substituted with —N($R^g$)$_2$, carboxyl ester, or 5- or 6-membered nonaromatic heterocyclyl, or two $R^b$ together with the nitrogen to which they are attached form a $C_{3-6}$nonaromatic heterocyclyl moiety optionally interrupted with one or two —O— or —N($R^g$), where $R^g$ is H or $C_{1-4}$alkyl; and —OC(O)—$R^c$ is derived from an amino acid where the —OC(O)— moiety of —OC(O)—$R^c$ corresponds to an acid moiety on the amino acid, and $R^c$ comprises —N($R^b$)$_2$ or a nitrogen-containing nonaromatic heterocyclyl, such as a 5- or 6-membered unsaturated nitrogen-containing heterocyclyl, for example, pyrrolidinyl. The amino acid can be any amino acid, such as a naturally occurring amino acid, and may be an amino acid selected from glycine, valine, alanine, leucine, isoleucine, methionine, phenylalanine, tryptophan, tyrosine, serine, threonine, asparagine, glutamine, arginine, histidine, lysine, aspartic acid, glutamic acid, cysteine, or proline. A person of ordinary skill in the art will understand that where the amino acid comprises one or more chiral center, all enantiomers, diastereomers and/or mixtures thereof are contemplated. For example, the amino acid may be the L-amino acid, the D-amino acid or a mixture thereof. In some embodiments, the amino acid is the L-amino acid. And in certain embodiments, —OC(O)—$R^c$ is —OC(O)CH(NH$_2$)$R^d$,

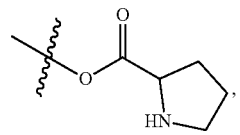 [SMILES: *OC(=O)C1CCCN1]

or —OC(O)—(CH$_2$)$_{1-2}$C(NH$_2$)CO$_2$H, where $R^d$ is an amino acid side chain, and/or may be H, —CH$_3$, isopropyl, —CH$_2$CH(CH$_3$)$_2$, —CH(CH$_3$)Et, —CH$_2$CH$_2$SCH$_3$,

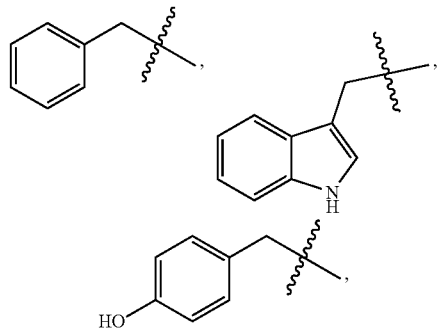

—CH$_2$OH, —CH(OH)CH$_3$, —CH$_2$C(O)NH$_2$, —CH$_2$CH$_2$C(O)NH$_2$, —CH$_2$SH, —CH$_2$CH$_2$CH$_2$NHC(O)(NH)NH$_2$,

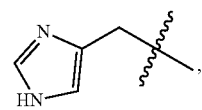 [SMILES: *Cc1c[nH]cn1]

—CH$_2$CH$_2$CH$_2$CH$_2$NH$_2$, —CH$_2$CO$_2$H, or CH$_2$CH$_2$CO$_2$H.

In some embodiments, $R^1$ is H, alkyl, or -alkylOP(O)(OR)$_2$ where each OR independently is —OH, —Oalkyl, —Oaryl, —Oheteroaryl, —Oaralkyl, or —O⁻M⁺ where M⁺ is a counter ion with a single positive charge. Each OR independently may be —OH, —O(C$_{1-6}$alkyl), —OC$_6$aryl, —O(3-15 membered heteroaryl), —OC$_7$aralkyl, or —O⁻M⁺. And in some embodiments, the two OR moieties are different, but in other embodiments, the two OR moieties are the same.

In some embodiments, R$^1$ is H, C$_{1-6}$alkyl, or —C$_{1-4}$alkylOP(O)(OR)$_2$ such as H, C$_{1-6}$alkyl, —CH$_2$OP(O)(OR)$_2$, or —CH(CH$_3$)OP(O)(OR)$_2$, and in certain embodiments, R$^1$ is H, C$_{1-6}$alkyl, or —CH$_2$OP(O)(OR)$_2$.

In particular embodiments, the compound has a structure according to Formula II or a pharmaceutically acceptable salt or solvate thereof.

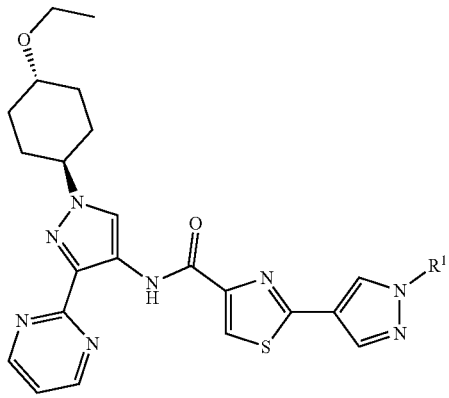

Formula II

With respect to Formula II, R$^1$ is a previously defined for Formula I.

In some embodiments of Formulas I and II, R$^1$ is H.

In other embodiments of Formulas I and II, R$^1$ is alkyl, such as C$_{1-6}$alkyl or C$_{1-4}$alkyl, and may be methyl or ethyl.

In some other embodiments of Formulas I and II, R$^1$ is -alkylOP(O)(OR)$_2$, such as —C$_{1-4}$alkylOP(O)(OR)$_2$, and may be —CH$_2$OP(O)(OR)$_2$, or —CH(CH$_3$)OP(O)(OR)$_2$.

In some embodiments, R$^1$ is —CH$_2$OP(O)(OR)$_2$. In one embodiment, R$^1$ is —CH$_2$OP(O)(OH)$_2$. In another embodiment, R$^1$ is —CH$_2$OP(O)(OH)(O⁻M⁺). In another embodiment, R$^1$ is —CH$_2$OP(O)(O⁻M⁺)$_2$, and may be —CH$_2$OP(O)(O⁻Na⁺)$_2$. And in another embodiments, R$^2$ is —CH$_2$OP(O)(OC$_{1-6}$alkyl)$_2$.

In some embodiments, R$^1$ is —CH(CH$_3$)OP(O)(OR)$_2$. In one embodiment, R$^1$ is —CH(CH$_3$)OP(O)(OH)$_2$. In another embodiment, R$^1$ is —CH(CH$_3$)OP(O)(OH)(O⁻M⁺). In another embodiment, R$^1$ is —CH(CH$_3$)OP(O)(O⁻M⁺)$_2$, and may be —CH(CH$_3$)OP(O)(O⁻Na⁺)$_2$. And in another embodiments, R$^2$ is —CH(CH$_3$)OP(O)(OC$_{1-6}$alkyl)$_2$.

In one embodiment disclosed herein the compound comprises an IRAK inhibitory moiety and a means for releasing or delivering the IRAK inhibitory moiety in vivo. By way of example, in some embodiments of Formulas I and II where R$^1$ is not H, R$^1$ comprises a means for delivering an IRAK inhibitor, such as compound I-1 disclosed herein. Exemplary embodiments of Formulas I and II comprising such means will be readily apparent to those of skill in the art upon consideration of the Formulas and working examples disclosed herein. By way of example, embodiments of Formulas I and II comprising a means for delivering an IRAK inhibitory moiety include, without limitation, compounds I-2, I-3, I-6, I-7 and I-8.

In any embodiments, the compound may be in a free base form or it may be a salt. In some embodiments, the salt is an acid addition salt, such as, but not limited to, the acid addition salts defined herein. In particular embodiments, the compound is a tartaric acid salt.

In other embodiments, the compound is in the form of a base addition salt, such as, but not limited to, the base addition salts defined herein. In some embodiments, the compound is a sodium salt, such as a disodium salt, or a tris salt.

Exemplary compounds according to Formula I include, but are not limited to:

I-1

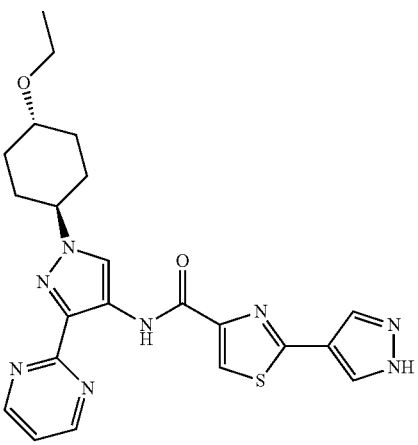

I-2

I-3

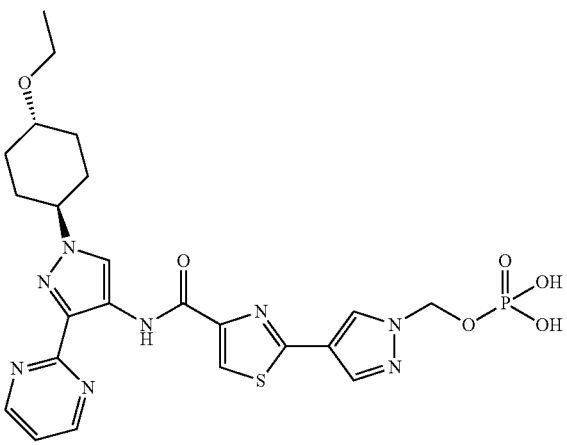

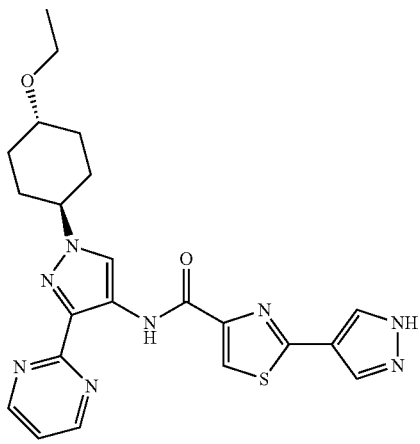

I-4

Tartaric acid salt

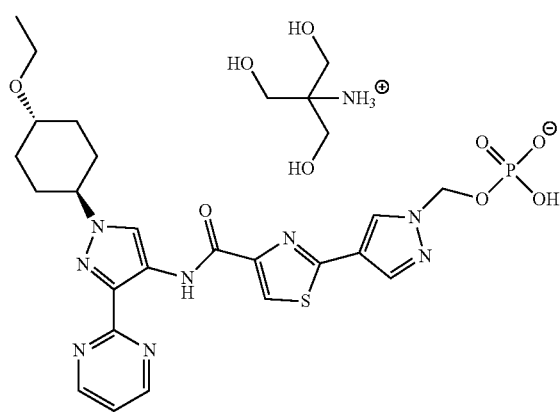

I-5

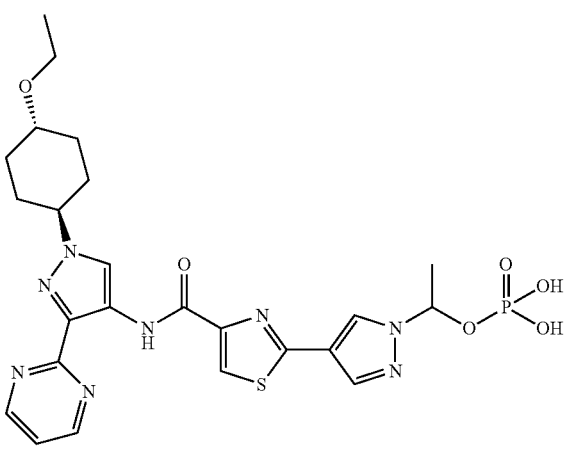

I-6

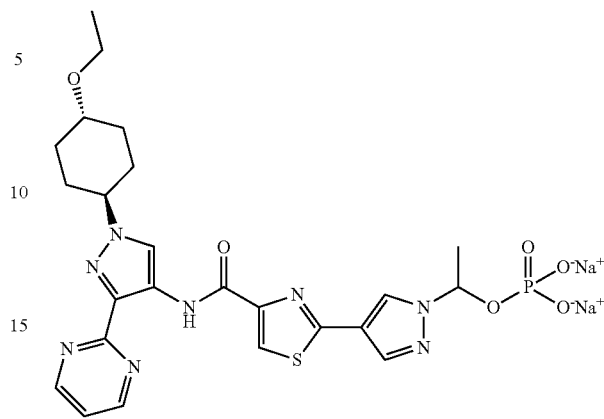

I-7

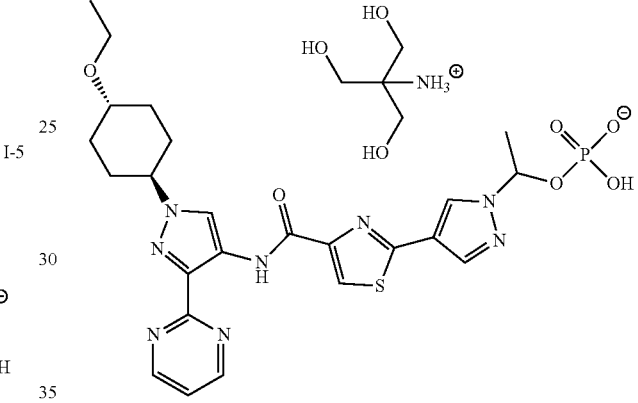

I-8

Some exemplary compounds according to formula 1 include:

I-1: N-(1-((1r,4r)-4-ethoxycyclohexyl)-3-(pyrimidin-2-yl)-1H-pyrazol-4-yl)-2-(1H-pyrazol-4-yl)thiazole-4-carboxamide;

I-2: (4-(4-((1-((1r,4r)-4-ethoxycyclohexyl)-3-(pyrimidin-2-yl)-1H-pyrazol-4-yl)carbamoyl)thiazol-2-yl)-1H-pyrazol-1-yl)methyl dihydrogen phosphate;

I-3: sodium (4-(4-((1-((1r,4r)-4-ethoxycyclohexyl)-3-(pyrimidin-2-yl)-1H-pyrazol-4-yl)carbamoyl)thiazol-2-yl)-1H-pyrazol-1-yl)methyl phosphate;

I-4: N-(1-((1r,4r)-4-ethoxycyclohexyl)-3-(pyrimidin-2-yl)-1H-pyrazol-4-yl)-2-(1H-pyrazol-4-yl)thiazole-4-carboxamide tartaric acid salt;

I-5: (4-(4-((1-((1r,4r)-4-ethoxycyclohexyl)-3-(pyrimidin-2-yl)-1H-pyrazol-4-yl)carbamoyl)thiazol-2-yl)-1H-pyrazol-1-yl)methyl hydrogen phosphate 1,3-dihydroxy-2-(hydroxymethyl)propan-2-aminium (tris salt);

I-6: 1-(4-(4-((1-((1r,4r)-4-ethoxycyclohexyl)-3-(pyrimidin-2-yl)-1H-pyrazol-4-yl)carbamoyl)thiazol-2-yl)-1H-pyrazol-1-yl)ethyl dihydrogen phosphate;

I-7: sodium 1-(4-(4-((1-((1r,4r)-4-ethoxycyclohexyl)-3-(pyrimidin-2-yl)-1H-pyrazol-4-yl)carbamoyl)thiazol-2-yl)-1H-pyrazol-1-yl)ethyl phosphate; or I-8: 1-(4-(4-((1-((1r,4r)-4-ethoxycyclohexyl)-3-(pyrimidin-2-yl)-1H-pyrazol-4-yl)carbamoyl)thiazol-2-yl)-1H-pyrazol-1-yl)ethyl hydrogen phosphate 1,3-dihydroxy-2-(hydroxymethyl)propan-2-aminium (tris salt).

In some embodiments, a compound according to any one of Formulas I and II, or a salt thereof, has at least one improved property compared to other IRAK inhibitors.

The one or more improved property may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, selectivity such as selectivity for one IRAK protein over a different IRAK protein, activity, and/or half-life.

III. Synthesis

Disclosed pyrazole compounds can be prepared as exemplified below, and as will be understood by a person of ordinary skill in the art in organic synthesis. An exemplary synthesis may include the following 1$^{st}$ reaction step according to Scheme 1:

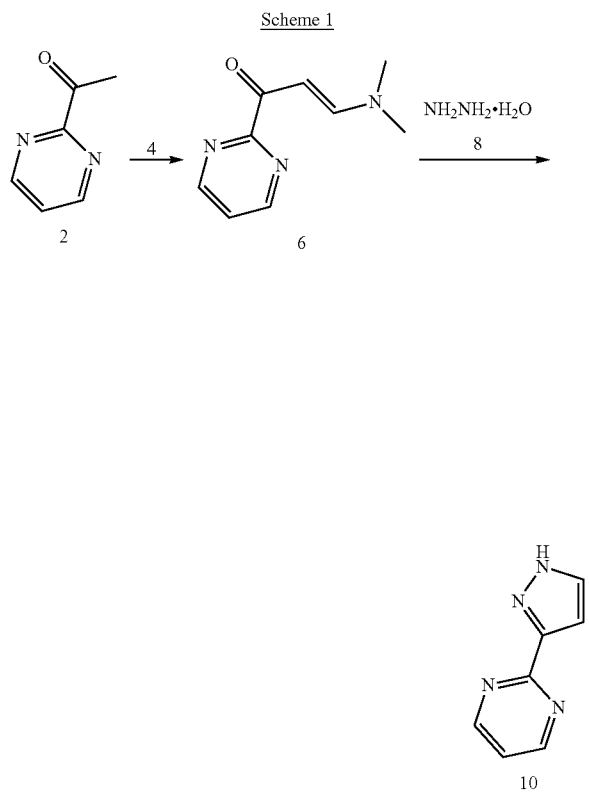

Acetyl compound 2 is reacted with dimethylformamide dimethylacetal 4 to form intermediate compound 6, at a temperature suitable to facilitate a reaction. A suitable temperature is typically from 85° C. to 130° C. Intermediate compound 6 is then reacted with hydrazine hydrate 8 to form the pyrazole compound 10. The reaction is performed in a suitable solvent, for example, an alcohol such as ethanol, methanol or isopropanol, and is typically heated, such as to reflux.

A 2$^{nd}$ reaction step in the exemplary synthesis is provided below according to Scheme 2:

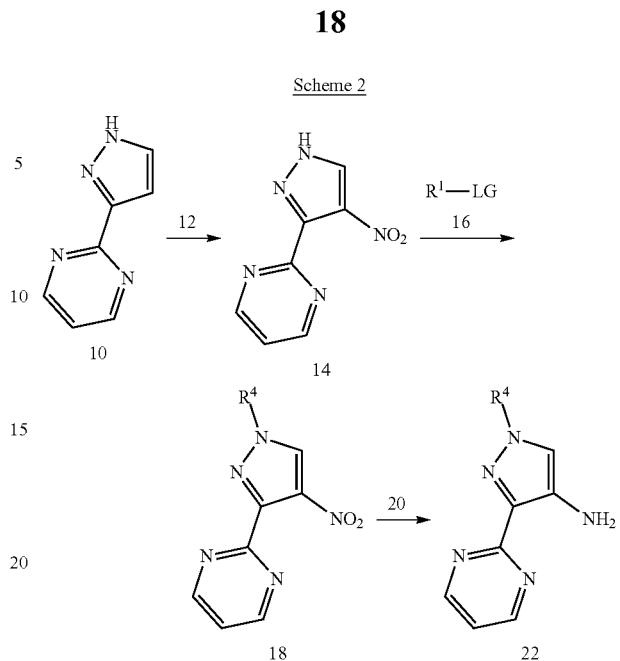

Compound 10 is nitrated using a suitable nitrating reagent or mixture of reagents 12 to form compound 14. Suitable nitrating conditions include reacting compound 10 with nitric acid, such as fuming nitric acid, optionally in the presence of sulfuric acid. Typically, compound 10 and the nitric acid are added slowly, one to the other. Cooling, such as by an ice bath, may be used to maintain the reaction temperature within a suitable range, such as from about 0° C. to less than 50° C., from 0° C. to 20° C., or from 0° C. to 10° C. After the addition is complete the reaction is allowed to proceed until the reaction is substantially complete, and may be allowed to warm to room temperature to facilitate the reaction. Optionally, additional nitrating reagent, or mixture of nitrating reagents, may be added to facilitate the reaction proceeding to completion. The reaction is then quenched, such as by addition to water and/or ice, and the product is separated or extracted from the aqueous and purified if required. Purification techniques suitable for purifying a product from any reaction disclosed herein include, but are not limited to, crystallization, distillation and/or chromatography.

With continued reference to Scheme 2, compound 14 is then reacted with compound 16 to form compound 18. Compound 16 comprises a desired $R^1$ moiety and a suitable leaving group, LG. Suitable leaving groups include any group that will act as a leaving group to facilitate the addition of the $R^1$ moiety to compound 14. Suitable leaving groups include, but are not limited to, halogens, typically bromo, chloro or iodo, and tosylate or mesylate groups. Compound 14 is reacted with compound 16 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may be heated, such as to 50° C., 100° C. or higher, as required, or the reaction may proceed at room temperature. Compound 18 is then isolated from the reaction mixture and purified if required.

Compound 18 is then reacted with a reducing agent 20 suitable to reduce the nitro moiety to an amine. Suitable reducing agents include, but are not limited to: hydrogen gas in the presence of a catalyst, such as a palladium catalyst; a borohydride, such as sodium borohydride, optionally in the presence of a catalyst, such as a nickel catalyst; zinc metal in acetic acid; or iron powder in water or water and acid. In certain embodiments, hydrogen gas is used, in the presence of a palladium on carbon catalyst, and in a suitable solvent, such as ethyl acetate or methanol. In some embodiments, a combination of reducing agents and/or techniques are used. For example, reduction may be initially performed using a first method comprising a first reducing agent and/or technique, but result in a mixture of products. The first method may be repeated, and/or a second method may be performed, comprising a second reducing agent and/or technique. Once the reaction is complete, as indicated by an analytical technique such as LC-MS, TLC or HPLC, the product compound 22 is isolated and purified if necessary.

A $3^{rd}$ step of the exemplary reaction sequence is provided below according to Scheme 3:

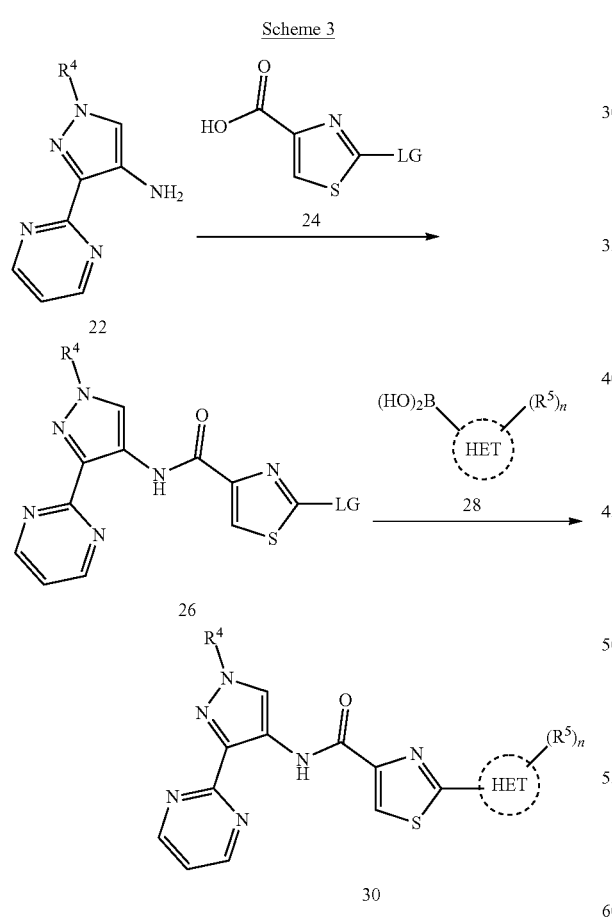

Compound 22 is reacted with a carboxylic acid 24 to form compound 26. The carboxylic acid 24 is activated by any suitable method and then reacted with the amine on compound 22. Suitable activation methods include, but are not limited to: forming the acid chloride by treatment with thionyl chloride; by treatment with 1-[Bis(dimethylamino) methylene]-1H-1,2,3-triazolo[4,5-b]pyridinium 3-oxid hexafluorophosphate (HATU) and a base such as diisopropylethylamine (DIPEA); by treatment with carbonyldiimidazole (CDI); or by treatment with a carbodiimide, such as dicyclohexylcarbodiimide (DCC) or 1-Ethyl-3-(3-dimethylaminopropyl)carbodiimide (EDC).

Compound 26 is then coupled with compound 28 to form compound 30 using any coupling reaction suitable to form a bond between two rings. In the example above, a boronic acid coupling is shown, where the leaving group LG on compound 26 is typically bromo or iodo. Other suitable coupling functional groups include trialkyl tin or boronic esters. The coupling reaction typically proceeds in the presence of a suitable catalyst. For a boronic acid coupling, the catalyst typically is a palladium catalyst, such as $PdCl_2$(dppf)$_2$, Pd[P(Ph)$_3$]$_2$Cl$_2$, palladium acetate and triphenyl phosphine, or tetrakis(triphenylphosphine)palladium(0). The reaction is performed in the presence of a base, such as sodium, potassium or cesium carbonate, and is performed in a suitable solvent or solvent mixture, such as dioxane, dioxane/water or DME/ethanol/water. The reaction may be heated at a suitable temperature, such as from 50° C. to 125° C., typically about 100° C., and/or agitated for a suitable period of time, such as from 1 hour to 3 days, from 6 hours to 24 hours, or from 12 hours to 18 hours, to facilitate the reaction proceeding to completion. Compound 30 is then isolated from the reaction mixture and purified by a suitable technique.

An alternative exemplary synthesis may include the following $1^{st}$ reaction step according to Scheme 4:

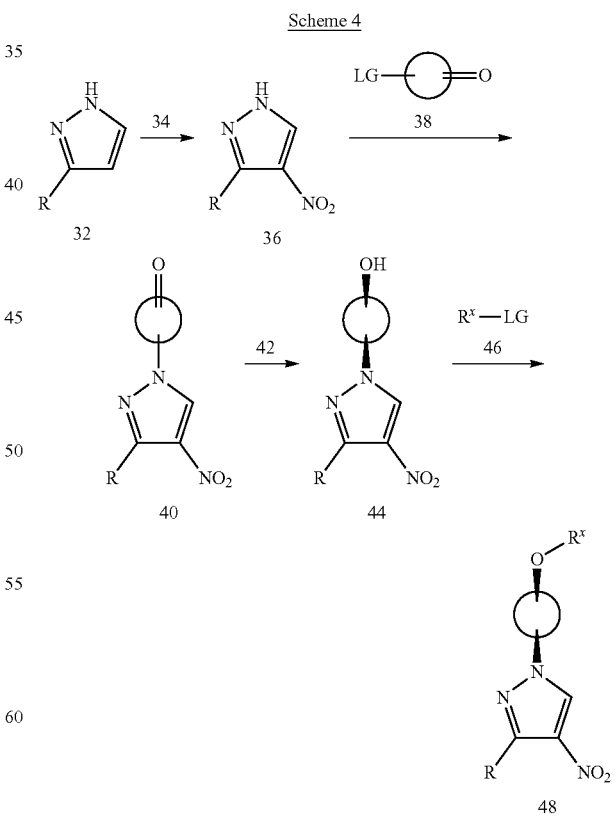

Compound 32 is nitrated using a suitable nitrating reagent or mixture of reagents 34 to form compound 36. Suitable nitrating conditions include reacting compound 32 with nitric acid, such as fuming nitric acid, optionally in the presence of sulfuric acid. Typically, compound 32 and the nitric acid are added slowly, one to the other. Cooling, such as by an ice bath, may be used to maintain the reaction temperature within a suitable range, such as from about 0° C. to less than 50° C., from 0° C. to 20° C., or from 0° C. to 10° C. After the addition is complete the reaction is allowed to proceed until the reaction is substantially complete, and may be allowed to warm to room temperature to facilitate the reaction. Optionally, additional nitrating reagent, or mixture of nitrating reagents, may be added to facilitate the reaction proceeding to completion. The reaction is then quenched, such as by addition to water and/or ice, and the product is separated or extracted from the aqueous and purified if required. Purification techniques suitable for purifying a product from any reaction disclosed herein include, but are not limited to, crystallization, distillation and/or chromatography.

With continued reference to Scheme 4, compound 36 is then reacted with compound 38 to form compound 40. Compound 38 comprises a desired ring, such as a cyclobutyl, cyclopentyl, or cyclohexyl ring, and a suitable leaving group, LG. Suitable leaving groups include any group that will act as a leaving group to facilitate the addition of the ring to compound 36. Suitable leaving groups include, but are not limited to, halogens, typically bromo, chloro or iodo, and tosylate or mesylate groups. Compound 36 is reacted with compound 38 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may be heated, such as to 50° C., 100° C. or higher, as required, or the reaction may proceed at room temperature. Compound 40 is then isolated from the reaction mixture and purified if required.

Compound 40 is then reacted with a reducing agent 42 suitable to reduce the carbonyl moiety to a hydroxyl. Suitable reducing agents include, but are not limited to, sodium borohydride, di-isobutyl aluminum hydride, or lithium aluminum hydride. The reaction is performed in a solvent suitable to facilitate the reaction, such as an alcohol, particularly methanol or ethanol; THF; or diethyl ether. The reaction may be heated, such as to 50° C., 100° C. or higher, as required, cooled, such as to below 20° C., below 10° C., below 0° C. or lower, or the reaction may proceed at room temperature. Once the reaction is complete, as indicated by an analytical technique such as LC-MS, TLC or HPLC, the product compound 44 is isolated and purified if necessary, by a suitable technique, such as column chromatography.

Optionally, compound 44 may be reacted with compound 46 to form compound 48. Compound 46 comprises a desired $R^x$ moiety and a suitable leaving group, LG. Suitable leaving groups include any group that will act as a leaving group to facilitate the addition of the $R^x$ moiety to compound 44. Suitable leaving groups include, but are not limited to, halogens, typically bromo, chloro or iodo, and tosylate or mesylate groups. Compound 44 is reacted with compound 46 in a suitable solvent and typically in the presence of a base or other reagent or reagents that facilitates the reaction. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases or reagents that facilitate the reaction include, but are not limited to, silver triflate, 2,6-di-t-butylpyridine, sodium hydride, or combinations thereof. Typically, compound 46 is slowly combined with the reaction. Cooling, such as by an ice bath, may be used to maintain the reaction temperature within a suitable range, such as from about 0° C. to less than 50° C., from 0° C. to 20° C., or from 0° C. to 10° C. After the addition is complete the reaction is allowed to proceed until the reaction is substantially complete, and may be allowed to warm to room temperature, or the reaction may be heated, such as to 50° C., 100° C. or higher, to facilitate the reaction. Once the reaction is complete, as indicated by an analytical technique such as LC-MS, TLC or HPLC, the product compound 48 is isolated and purified if necessary, by a suitable technique, such as column chromatography.

Alternatively, compound 40 may be prepared by an exemplary synthetic route according to Scheme 5:

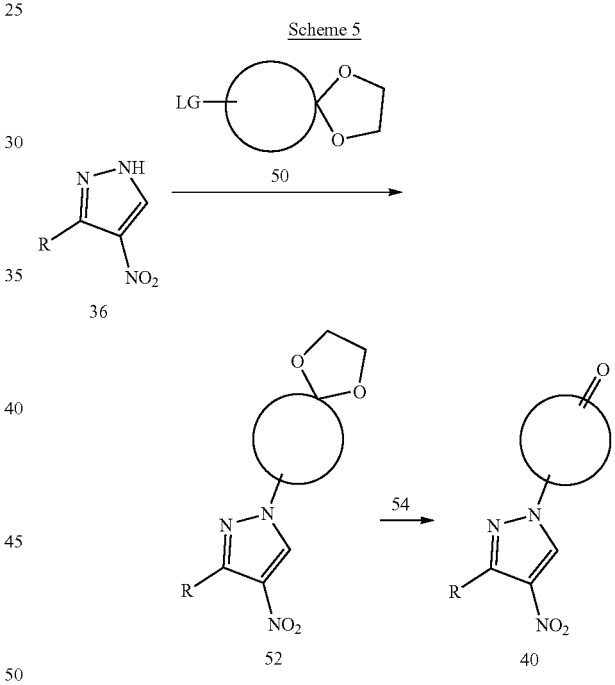

With respect to Scheme 5, compound 36 is reacted with compound 50 to form compound 52. Compound 50 comprises a desired ring, such as a cyclobutyl, cyclopentyl, or cyclohexyl ring, a suitable leaving group, LG, and a protected carbonyl moiety, such as an acetal or a ketal. In the example above a cyclic ketal moiety is shown. Suitable leaving groups include any group that will act as a leaving group to facilitate the addition of the ring to compound 36, and include, but are not limited to, halogens, typically bromo, chloro or iodo, and tosylate or mesylate groups. Compound 36 is reacted with compound 50 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may be heated, such as to 50° C., 100° C. or higher, as required, or the reaction may proceed at room temperature. Compound 52 is then isolated from the reaction mixture and purified if required by a suitable technique, such as column chromatography.

Compound 52 is then reacted with a suitable reagent 54 to form compound 40. Reagent 54 may be any reagent suitable to remove the protecting group and/or form the carbonyl moiety. In the exemplary synthesis shown in Scheme 5, the protecting group is a cyclic ketal, and suitable reagents 54 include, but are not limited to, pyridinium tosylate (PPTS), para-toluene sulfonic acid, hydrochloric acid, or acetic acid. The reaction is performed in a solvent or mixture of solvents suitable to facilitate the reaction, such as acetone, THF, acetic acid, water, or a combination thereof. The reaction may be heated, such as to 50° C., 100° C. or higher, or at reflux, as required, or the reaction may proceed at room temperature. Compound 40 is then isolated from the reaction mixture and purified if required by a suitable technique, such as column chromatography.

A $2^{nd}$ step of the exemplary reaction sequence is provided below according to Scheme 6:

Scheme 6

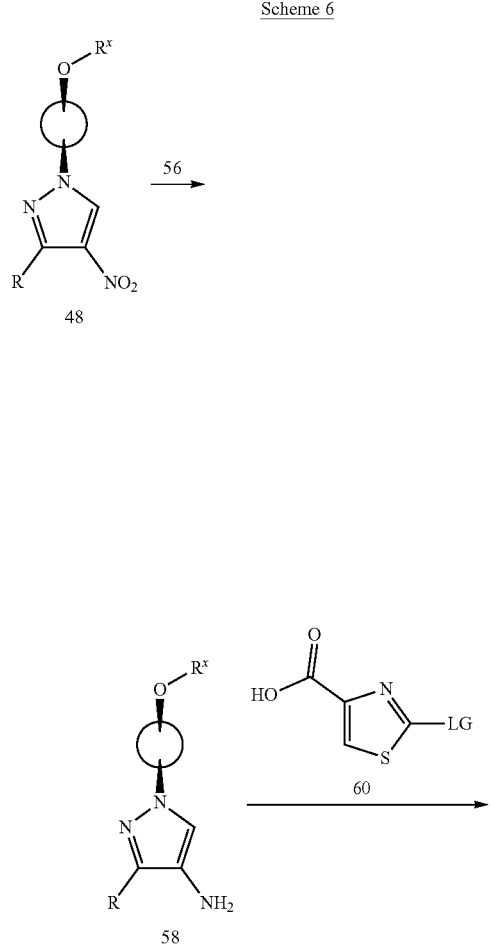

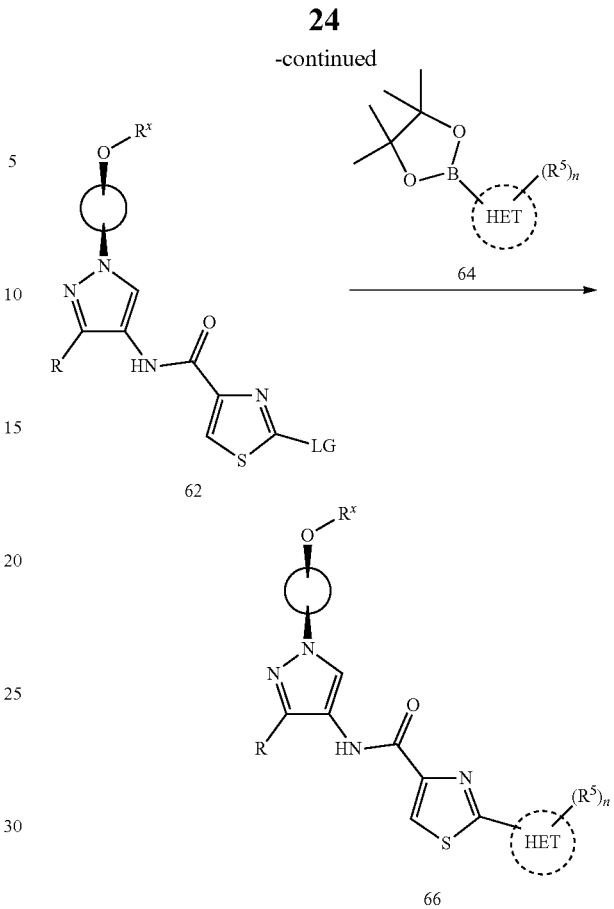

Compound 48 is then reacted with a reducing agent 56 suitable to reduce the nitro moiety to an amine. In certain embodiments where the desired product compound comprises a hydroxyl moiety, compound 44 may be used in place of compound 48. Suitable reducing agents include, but are not limited to: hydrogen gas in the presence of a catalyst, such as a palladium catalyst; a borohydride, such as sodium borohydride, optionally in the presence of a catalyst, such as a nickel catalyst; zinc metal in acetic acid; or iron powder in water or water and acid. In certain embodiments, hydrogen gas is used, in the presence of a palladium on carbon catalyst, and in a suitable solvent, such as ethyl acetate or methanol. In some embodiments, a combination of reducing agents and/or techniques are used. For example, reduction may be initially performed using a first method comprising a first reducing agent and/or technique, but result in a mixture of products. The first method may be repeated, and/or a second method may be performed, comprising a second reducing agent and/or technique. Once the reaction is complete, as indicated by an analytical technique such as LC-MS, TLC or HPLC, the product compound 58 is isolated and purified if necessary.

Compound 58 is reacted with a carboxylic acid 60 to form compound 62. The carboxylic acid 60 is activated by any suitable method and then reacted with the amine on compound 58. Suitable activation methods include, but are not limited to: forming the acid chloride by treatment with thionyl chloride; by treatment with 1-[Bis(dimethylamino) methylene]-1H-1,2,3-triazolo[4,5-b]pyridinium 3-oxid hexafluorophosphate (HATU) and a base such as diisopropylethylamine (DIPEA); by treatment with carbonyldiimidazole (CDI); or by treatment with a carbodiimide, such as dicyclohexylcarbodiimide (DCC) or 1-Ethyl-3-(3-dimethylaminopropyl)carbodiimide (EDC).

Compound 62 is then coupled with compound 64 to form compound 66 using any coupling reaction suitable to form a bond between two rings. In the example above, a boronic ester coupling is shown, where the leaving group LG on compound 62 is typically bromo or iodo. Other suitable coupling functional groups include trialkyl tin or boronic acids. The coupling reaction typically proceeds in the presence of a suitable catalyst. For a boronic ester or boronic acid coupling, the catalyst typically is a palladium catalyst, such as $PdCl_2(dppf)_2$, $Pd[P(Ph)_3]_2Cl_2$, palladium acetate and triphenyl phosphine, or tetrakis(triphenylphosphine)palladium(0). The reaction is performed in the presence of a base, such as sodium, potassium or cesium carbonate, and is performed in a suitable solvent or solvent mixture, such as dioxane, dioxane/water or DME/ethanol/water. The reaction may be heated at a suitable temperature, such as from 50° C. to 125° C., typically about 100° C., and/or agitated for a suitable period of time, such as from 1 hour to 3 days, from 6 hours to 24 hours, or from 12 hours to 18 hours, to facilitate the reaction proceeding to completion. Compound 66 is then isolated from the reaction mixture and purified by a suitable technique. Certain embodiments may comprise a phosphate moiety. Scheme 7 provides an exemplary synthesis of certain such embodiments:

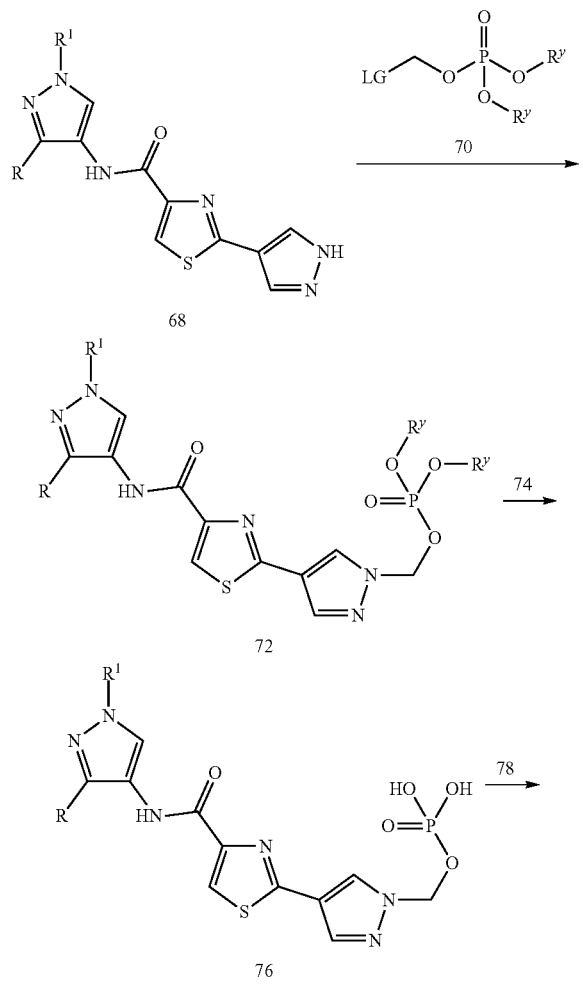

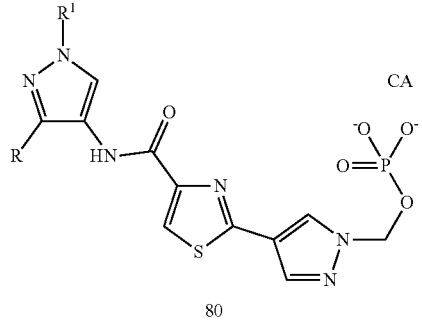

Compound 68 is reacted with compound 70 to form compound 72. Compound 70 comprises desired $R^y$ moieties and a suitable leaving group, LG. Typical $R^y$ moieties include, but are not limited to aliphatic, such as alkyl, typically methyl, ethyl, propyl, isopropyl or t-butyl; aryl; heteroaliphatic; or heterocyclic. The two $R^y$ moieties may be the same or different. Suitable leaving groups include, but are not limited to, halogens, typically bromo, chloro or iodo, and tosylate or mesylate groups. Compound 68 is reacted with compound 70 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may be heated, such as to 50° C., 100° C. or higher, as required, or the reaction may proceed at room temperature. Compound 72 is then isolated from the reaction mixture and purified if required.

Compound 72 is then reacted with compound 74 to form compound 76. Compound 74 may be any compound suitable to form the acid moieties in compound 76. Compound 74 may be an acidic reagent, such as trifluoroacetic acid, hydrochloride acid, or hydrobromic acid, or it may be a basic reagent, such as sodium hydroxide, lithium hydroxide or potassium hydroxide. Suitable solvents include, but are not limited to, chlorinated solvents such as dichloromethane and chloroform, alcohols such as methanol and ethanol, water, or combinations thereof. The reaction may be heated, such as to 50° C., 100° C. or higher, as required, cooled, such as to below 20° C., below 10° C., below 0° C. or lower, or the reaction may proceed at room temperature. Once the reaction is complete, as indicated by an analytical technique such as LC-MS, TLC or HPLC, the product compound 76 is isolated and purified if necessary, by a suitable technique, such as by agitating, such as by stirring or sonication, in a suitable solvent or solvent system. Suitable solvents or solvent systems include, but are not limited to, acetone/water, acetone, diethyl ether, or alcohol/water.

Compound 76 is then reacted with compound 78 to form the salt compound 80. Compound 78 can be any compound that will provide a suitable counterion CA for the salt compound 80, such as calcium hydroxide, sodium hydroxide, potassium hydroxide, lithium hydroxide, ammonia, trimethylamine, tris(hydroxymethyl)aminomethane, or an amino acid such as lysine or arginine. A person of ordinary skill in the art will appreciate that if counter ion CA has a single positive charge, as in $Na^+$, $K^+$, $Li^+$, or $NH_4^+$, then compound 80 will comprise two CA ions, whereas if counter ion CA has two positive charges, as in $CA^{2+}$ compound 80 will comprise one CA ion.

IV. Combinations of Therapeutic Agents

The compounds of the present disclosure may be used alone, in combination with one another, in separate pharmaceutical compositions, together in a single composition, or as an adjunct to, or in combination with, other established therapies. The compound or compounds may be administered once, or more likely plural administrations. In another aspect, the compounds of the present disclosure may be used in combination with other therapeutic agents useful for the disorder or condition being treated. These compounds and/or agents may be administered simultaneously, sequentially in any order, by the same route of administration, or by a different route. For sequential administration, the compound(s) and/or agent(s) may be administered such that an effective time period of at least one compound and/or agent overlaps with an effective time period of at least one other compound and/or agent. In an exemplary embodiment of a combination comprising four components, the effective time period of the first component administered may overlap with the effective time periods of the second, third and fourth components, but the effective time periods of the second, third and fourth components independently may or may not overlap with one another. In another exemplary embodiment of a combination comprising four components, the effective time period of the first component administered overlaps with the effective time period of the second component, but not that of the third or fourth; the effective time period of the second component overlaps with those of the first and third components; and the effective time period of the fourth component overlaps with that of the third component only. In some embodiments, the effective time periods of all compounds and/or agents overlap with each other.

In some embodiments, disclosed compounds are administered with another therapeutic agent, such as an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof. In certain embodiments, the second therapeutic is an anti-inflammatory agent, an immunosuppressant and/or may be a steroid.

The anti-inflammatory agent may be a steroid or a nonsteroidal anti-inflammatory agent. In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

In some embodiments, the present compounds may be used with anti-cancer or cytotoxic agents. Various classes of anti-cancer and anti-neoplastic compounds include, but are not limited to, alkylating agents, antimetabolites, BCL-2 inhibitors, vinca alkyloids, taxanes, antibiotics, enzymes, cytokines, platinum coordination complexes, proteasome inhibitors, substituted ureas, kinase inhibitors, hormones and hormone antagonists, and hypomethylating agents, for example DNMT inhibitors, such as azacitidine and decitabine. Exemplary alkylating agents include, without limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrmidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as an anti-neoplastic agent includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesterone caproate, medroxyprogesterone; and anti-estrogen compound tamoxifen.

These and other useful anti-cancer compounds are described in Merck Index, 13th Ed. (O'Neil M. J. et al., ed.) Merck Publishing Group (2001) and Goodman and Gilman's The Pharmacological Basis of Therapeutics, 12th Edition, Brunton L. L. ed., Chapters 60-63, McGraw Hill, (2011), both of which are incorporated by reference herein.

Among the CTLA 4 antibodies that can be used in combination with the presently disclosed inhbitors is ipilimumab, marketed as YERVOY® by Bristol-Myers Squibb.

Other chemotherapeutic agents for combination include immunooncology agents, such as checkpoint pathway inhibitors, for example, PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti-CD137 agents, such as the fully human monoclonal antibody urelumab (BMS-663513).

Additional anti-proliferative compounds useful in combination with the compounds of the present disclosure include, by way of example and not limitation, antibodies directed against growth factor receptors (e.g., anti-Her2); and cytokines such as interferon-α and interferon-γ, interleukin-2, and GM-CSF.

Additional chemotherapeutic agents useful in combination with the present compounds include proteasome inhibitors, such as bortezomib, carfilzomib, marizomib and the like.

Examples of kinase inhibitors that are useful in combination with the presently disclosed compounds, particularly in treating malignancies include: Btk inhibitors, such as ibrutinib; CDK inhibitors, such as palbociclib; EGFR inhibitors, such as afatinib, erlotinib, gefitinib, lapatinib, osimertinib and vandetinib; Mek inhibitors, such as trametinib; Raf inhibitors, such as dabrafenib, sorafenib and vemurafenib; VEGFR inhibitors, such as axitinib, lenvatinib, nintedanib, pazopanib; BCR-Abl inhibitors, such as bosutinib, dasatinib, imatinib and nilotinib; Syk inhibitors, such as fostamatinib; and JAK inhibitors, such as ruxolitinib.

In other embodiments, the second therapeutic agent may be selected from any of the following:

analgesics-morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics-aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides (e.g., daptomycin), macrolides (azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicillins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others, such as arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole;

antibodies-anti-TNF-α antibodies, e.g., infliximab (Remicade™), adalimumab, golimumab, certolizumab; anti-B cell antibodies, e.g., rituximab; anti-IL-6 antibodies, e.g., tocilizumab; anti-IL-1 antibodies, e.g., anakinra; anti PD-1 and/or anti-PD-L1 antibodies, e.g. nivolumab, pembrolizumab, pidilizumab, BMS-936559, MPDL3280A, AMP-224, MEDI4736; ixekizumab, brodalumab, ofatumumab, sirukumab, clenoliximab, clazakiumab, fezakinumab, fletikumab, mavrilimumab, ocrelizumab, sarilumab, secukinumab, toralizumab, zanolimumab;

anticoagulants-warfarin (Coumadin™), acenocoumarol, phenprocoumon, atromentin, phenindione, heparin, fondaparinux, idraparinux, rivaroxaban, apixaban, hirudin, lepirudin, bivalirudin, argatroban, dabigatran, ximelagatran, batroxobin, hementin;

anti-inflammatory agents-steroids, e.g., budesonide, nonsteroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants-mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan; mercaptopurine is currently available from Gate Pharmaceuticals, Inc. under the brand name Purinethol; prednisone and prednisolone are currently available from Roxane Laboratories, Inc.; Methyl prednisolone is currently available from Pfizer; sirolimus (rapamycin) is currently available from Wyeth-Ayerst under the brand name Rapamune; tacrolimus is currently available from Fujisawa under the brand name Prograf; cyclosporine is current available from Novartis under the brand name Sandimmune and Abbott under the brand name Gengraf; IMPDH inhibitors such as mycophenolate mofetil and mycophenolic acid are currently available from Roche under the brand name Cellcept and Novartis under the brand name Myfortic; azathioprine is currently available from Glaxo Smith Kline under the brand name Imuran; and antibodies are currently available from Ortho Biotech under the brand name Orthoclone, Novartis under the brand name Simulect (basiliximab) and Roche under the brand name Zenapax (daclizumab); and Guanylate cyclase-C receptor agonists or intestinal secretagogues, for example linaclotide, sold under the name Linzess.

In certain embodiments, the second therapeutic is, or comprises, a steroid, such as a corticosteroid, including, but not limited to, glucocorticoids and/or mineralocorticoids. Steroids suitable for use in combination with the disclosed compounds include synthetic and non-synthetic glucocorticoids. Exemplary steroids, such as glucocorticoids, suitable for use in the disclosed methods include, but are not limited to, alclomethasones, algestones, beclomethasones (e.g. beclomethasone dipropionate), betamethasones (e.g. betamethasone 17-valerate, betamethasone sodium acetate, betamethasone sodium phosphate, betamethasone valerate), budesonides, clobetasols (e.g. clobetasol propionate), clobetasones, clocortolones (e.g. clocortolone pivalate), cloprednols, corticosterones, cortisones, cortivazols, deflazacorts, desonides, desoximethasones, dexamethasones (e.g. dexamethasone 21-phosphate, dexamethasone acetate, dexamethasone sodium phosphate), diflorasones (e.g. diflorasone diacetate), diflucortolones, difluprednates, enoxolones, fluazacorts, flucloronides, fludrocortisones (e.g., fludrocortisone acetate), flumethasones (e.g. flumethasone pivalate), flunisolides, fluocinolones (e.g. fluocinolone acetonide), fluocinonides, fluocortins, fluocortolones, fluorometholones (e.g. fluorometholone acetate), fluperolones (e.g., fluperolone acetate), fluprednidenes, fluprednisolones, flurandrenolides, fluticasones (e.g. fluticasone propionate), formocortals, halcinonides, halobetasols, halometasones, halopredones, hydrocortamates, hydrocortisones (e.g. hydrocortisone 21-butyrate, hydrocortisone aceponate, hydrocortisone acetate, hydrocortisone buteprate, hydrocortisone butyrate, hydrocortisone cypionate, hydrocortisone hemisuccinate, hydrocortisone probutate, hydrocortisone sodium phosphate, hydrocortisone sodium succinate, hydrocortisone valerate), loteprednol etabonate, mazipredones, medrysones, meprednisones, methylprednisolones (methylprednisolone aceponate, methylprednisolone acetate, methylprednisolone hemi succinate, methylprednisolone sodium succinate), mometasones (e.g., mometasone furoate), paramethasones (e.g., paramethasone acetate), prednicarbates, prednisolones (e.g. prednisolone 25-diethylaminoacetate, prednisolone sodium phosphate, prednisolone 21-hemi succinate, prednisolone acetate; prednisolone farnesylate, prednisolone hemisuccinate, prednisolone-21 (beta-D-glucuronide), prednisolone metasulphobenzoate, prednisolone steaglate, prednisolone tebutate, prednisolone tetrahydrophthalate), prednisones, prednivals, prednylidenes, rimexolones, tixocortols, triamcinolones (e.g. triamcinolone acetonide, triamcinolone benetonide, triamcinolone hexacetonide, triamcinolone acetonide 21-palmitate, triamcinolone diacetate), or any combination thereof. Additional information concerning steroids, and the salts thereof, can be found, for example, in Remington's Pharmaceutical Sciences, A. Osol, ed., Mack Pub. Co., Easton, Pa. (16th ed. 1980).

In some examples, the steroid is a glucocorticoid, and may be selected from cortisone, dexamethasone, hydrocortisone, methylprednisolone, prednisolone, prednisone, or a combination thereof. In a particular example, the steroid is, or comprises, prednisone. In another particular example, the steroid is, or comprises, dexamethasone.

These various agents can be used in accordance with their standard or common dosages, as specified in the prescribing information accompanying commercially available forms of the drugs (see also, the prescribing information in the 2006 Edition of The Physician's Desk Reference), the disclosures of which are incorporated herein by reference.

V. Compositions Comprising the Disclosed Compounds

The disclosed compounds may be used alone, in any combination, and in combination with, or adjunctive to, at least one second therapeutic agent. Furthermore, the disclosed compound or compounds, and/or the at least one second therapeutic, may be used in combination with any suitable excipient useful for forming compositions for administration to a subject. Excipients can be included in pharmaceutical compositions for a variety of purposes, such as to dilute a composition for delivery to a subject, to facilitate processing of the formulation, to provide advantageous material properties to the formulation, to facilitate dispersion from a delivery device, to stabilize the formulation (e.g., antioxidants or buffers), to provide a pleasant or palatable taste or consistency to the formulation, or the like. The pharmaceutically acceptable excipient(s) may include a pharmaceutically acceptable carrier(s) and/or a pharmaceutically acceptable adjuvant(s). Exemplary excipients include, but are not limited to: mono-, di-, and polysaccharides, sugar alcohols and other polyols, such as, lactose, glucose, raffinose, melezitose, lactitol, maltitol, trehalose, sucrose, mannitol, starch, or combinations thereof; surfactants, such as sorbitols, diphosphatidyl choline, and lecithin; bulking agents; buffers, such as phosphate and citrate buffers; antiadherents, such as magnesium stearate; binders, such as saccharides (including disaccharides, such as sucrose and lactose), polysaccharides (such as starches, cellulose, microcrystalline cellulose, cellulose ethers (such as hydroxypropyl cellulose)), gelatin, synthetic polymers (such as polyvinylpyrrolidone, polyalkylene glycols); coatings (such as cellulose ethers, including hydroxypropylmethyl cellulose, shellac, corn protein zein, and gelatin); release aids (such as enteric coatings); disintegrants (such as crospovidone, crosslinked sodium carboxymethyl cellulose, and sodium starch glycolate); fillers (such as dibasic calcium phosphate, vegetable fats and oils, lactose, sucrose, glucose, mannitol, sorbitol, calcium carbonate, and magnesium stearate); flavors and sweeteners (such as mint, cherry, anise, peach, apricot or licorice, raspberry, and vanilla); lubricants (such as minerals, exemplified by talc or silica, fats, exemplified by vegetable stearin, magnesium stearate or stearic acid); preservatives (such as antioxidants exemplified by vitamin A, vitamin E, vitamin C, retinyl palmitate, and selenium, amino acids, exemplified by cysteine and methionine, citric acid and sodium citrate, parabens, exemplified by methyl paraben and propyl paraben); colorants; compression aids; emulsifying agents; encapsulation agents; gums; granulation agents; and combinations thereof.

VI. Methods of Use

A. Diseases/Disorders

The disclosed compounds, as well as combinations and/or compositions thereof, may be used to ameliorate, treat, and/or prevent a variety of diseases, conditions, and/or disorders. In particular embodiments, the disclosed compound, combinations of disclosed compounds, or compositions thereof, may be useful for treating conditions in which inhibition of an interleukin-1 receptor-associated kinase (IRAK) pathway is therapeutically useful. In some embodiments, the compounds directly inhibit an IRAK protein, such as IRAK1, IRAK2, IRAK3 and/or IRAK4. In certain embodiments, disclosed compounds are useful for treating, preventing, and/or ameliorating auto-immune diseases, inflammatory disorders, cardiovascular diseases, nerve disorders, neurodegenerative disorders, allergic disorders, asthma, pancreatitis, multi-organ failure, kidney diseases, platelet aggregation, cancer, transplantation, sperm motility, erythrocyte deficiency, graft rejection, lung injuries, respiratory diseases, ischemic conditions, and bacterial and viral infections.

In some embodiments, the disclosed compound, combinations of disclosed compounds, or compositions thereof, may be used to treat or prevent allergic diseases, amyotrophic lateral sclerosis (ALS), systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmyopathy, or asthma.

The disclosed compound, combinations of disclosed compounds, or compositions thereof, may also be useful for ameliorating, treating, and/or preventing immune regulatory disorders related to bone marrow or organ transplant rejection or graft-versus-host disease. Examples of inflammatory and immune regulatory disorders that can be treated with the present compounds include, but are not limited to, transplantation of organs or tissue, graft-versus-host diseases brought about by transplantation, autoimmune syndromes including rheumatoid arthritis, lupus, including systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, celiac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA bullous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, non-alcoholic steatohepatitis (NASH), hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, Parkinson's disease, trauma, chronic bacterial infection, palmoplantar pustulosis, hidradenitis suppurativa, cytokine release syndrome (CRS), acute respiratory distress syndrome (ARDS), acute kidney injury (AKI), kidney malfunction, or thrombosis.

In some embodiments, the disease or condition is hidradenitis suppurativa, or a lymphoid neoplasm selected from myeloproliferative neoplasms (MPN) excluding polycythemia vera, myeloid/lymphoid neoplasms with PDGFRA rearrangement, myeloid/lymphoid neoplasms with PDGFRB rearrangement, myeloid/lymphoid neoplasms with FGFR1 rearrangement, myeloid/lymphoid neoplasms with PCM1-JAK2, myelodysplastic/myeloproliferative neoplasms (MDS/MPN), myeloid sarcoma, myeloid proliferations related to Down syndrome, blastic plasmacytoid dendritic cell neoplasm, B-lymphoblastic leukemia/lymphoma; and/or T-lymphoblastic leukemia/lymphoma. In some embodiments, the lymphoid neoplasm is a myeloproliferative neoplasm selected from chronic myeloid leukemia (CML), chronic neutrophilic leukemia (CNL), primary myelofibrosis (PMF), essential thrombocythemia, chronic eosinophilic leukemia, or a combination thereof. In other embodiments, the lymphoid neoplasm is a myelodysplastic/myeloproliferative neoplasm selected from chronic myelomonocytic leukemia, atypical chronic myeloid leukemia (aCML), juvenile myelomonocytic leukemia (JMML), MDS/MPN with ring sideroblasts and thrombocytosis (MDS/MPN-RS-T), or a combination thereof.

In certain embodiments the present compounds are useful for treating nerve pain, including neuropathic pain and inflammation induced pain.

In certain embodiments, the disclosed compound, combinations of disclosed compounds, or compositions thereof, are useful for treating and/or preventing rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, in particular pustular psoriasis, type I diabetes, type II diabetes, inflammatory bowel disease (Crohn's disease and ulcerative colitis), hyperimmunoglobulinemia d and periodic fever syndrome, cryopyrin-associated periodic syndromes, Schnitzler's syndrome, systemic juvenile idiopathic arthritis, adult's onset Still's disease, gout, gout flares, pseudogout, sapho syndrome, Castleman's disease, sepsis, stroke, atherosclerosis, celiac disease, DIRA (deficiency of Il-1 receptor antagonist), Alzheimer's disease, or Parkinson's disease.

Proliferative diseases that may be treated by the disclosed compound, combinations of disclosed compounds, or compositions thereof, include benign or malignant tumors, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, IL-1 driven disorders, a MyD88 driven disorder (such as ABC diffuse large B-cell lymphoma (DLBCL), Waldenström's macroglobulinemia, Hodgkin's lymphoma, primary cutaneous T-cell lymphoma or chronic lymphocytic leukemia), smoldering or indolent multiple myeloma, or hematological malignancies (including leukemia, acute myeloid leukemia (AML), DLBCL, ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, myelodysplastic syndromes (MDS), myelofibrosis, polycythemia vera, Kaposi's sarcoma, Waldenström's macroglobulinemia (WM), splenic marginal zone lymphoma, multiple myeloma, plasmacytoma, intravascular large B-cell lymphoma). In particular, the presently disclosed compounds are useful in treating drug resistant malignancies, such as those resistant to JAK inhibitors ibrutinib resistant malignancies, including ibrutinib resistant hematological malignancies, such as ibrutinib resistant CLL and ibrutinib resistant Waldenström's macroglobulinemia.

Examples of allergic disorders that may be treated using the disclosed compound, combinations of disclosed compounds, or compositions thereof, include, but are not limited to, asthma (e.g. atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or unapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma), allergic bronchopulmonary aspergillosis (ABPA), allergic rhinitis, perennial allergic rhinitis, perennial rhinitis, vasomotor rhinitis, post-nasal drip, purulent or non-purulent sinusitis, acute or chronic sinusitis, and ethmoid, frontal, maxillary, or sphenoid sinusitis.

As another example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The disclosed compound, combinations of disclosed compounds, or compositions thereof, may be used to treat, ameliorate, or prevent any single, several or all of these symptoms of RA. Thus, in the context of RA, the compounds are considered to provide therapeutic benefit when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria include Paulu's criteria and radiographic progression (e.g. Sharp score).

In some embodiments, therapeutic benefit in patients suffering from RA is achieved when the patient exhibits an ACR20. In specific embodiments, ACR improvements of ACRC50 or even ACR70 may be achieved.

Cytokine release syndrome (CRS) is a potentially life-threatening condition that may result from a variety of factors, including severe viral infections such as influenza, administration of antibodies that are used for immunotherapy, such as cancer immunotherapy, and non-protein-based cancer drugs such as oxaliplatin and lenalidomide. Immunotherapy can involve high levels of immune activation that exceed naturally occurring immune activation levels, and CRS is a non-antigen specific toxicity that can occur as a result. As immune-based therapies become more potent, CRS is becoming increasing diagnosed. CRS has also been observed in the setting of haploidentical donor stem cell transplantation, and graft-versus-host disease. Shimabukuro-Vornhagen et al., *Journal for Immuno Therapy of Cancer* 6:56 (2018). CRS is associated with elevated circulating levels of several cytokines including interleukin (IL)-6 and interferon 7. Lee et al., *Blood* 124(2): 188-195 (10 Jul. 2014; Epub 29 May 2014).

CRS typically is clinically observed when significant numbers of lymphocytes and/or myeloid cells are activated and release inflammatory cytokines. The cytokine release may be induced by chemo- or biotherapy, and/or may be associated with therapeutic antibody treatments, such as immunotherapy, for example, for cancer treatment. Exemplary immunotherapies that may result in CRS include, but are not limited to, therapies where the cells express recombinant receptors, such as chimeric antigen receptors (CARs) and/or other transgenic receptors such as T cell receptors (TCRs). CRS induced by CAR T therapy generally occurs within days of T cell infusion at the peak of CAR T cell expansion. Giavridis et al., *Nat Med.* 24(6):731-738 (June 2018; Epub 28 May 2018). Examples of CAR T therapy that can induce CRS include axicabtagene ciloleucel (marketed as YESCARTA®) and tisagenlecleucel (marketed as KYMRIAH®).

Highly elevated interleukin 6 (IL-6) levels have been observed in patients with CRS and also in murine models of the disease, indicating that IL-6 may have a role in CRS pathophysiology. Shimabukuro-Vornhagen, *J Immunother Cancer* 6(1), 56 (2018). IL-6 can signal via two different modes. Classical IL-6 signaling involves binding of IL-6 to a membrane-bound IL-6 receptor. However, the IL-6 receptor does not possess intracellular signaling domains. Instead, after soluble IL-6 binds to membrane-bound IL-6 receptors, the IL-6/IL-6 receptor complex binds to membrane-bound gp130, which initiates signaling through its intracellular domain. In trans-signaling, IL-6 binds to a soluble form of the IL-6 receptor, which is typically cleaved from the cell surface by metalloproteinases. The resulting soluble IL-6/

IL-6 receptor complex binds to gp130 and therefore can also induce signaling in cell types that do not express membrane bound IL-6 receptors.

IL-6 contributes to many of the key symptoms of CRS. Via trans-signaling, IL-6 leads to characteristic symptoms of severe CRS, i.e. vascular leakage, and activation of the complement and coagulation cascade inducing disseminated intravascular coagulation (DIC). In addition, IL-6 likely contributes to cardiomyopathy that is often observed in patients with CRS by promoting myocardial dysfunction. In a murine model, CRS developed within 2-3 days of CAR T cell infusion and could be lethal. Giavridis et al., *Nat Med.* 24(6): 731-738 (2018). CRS symptoms may start within minutes or hours of the start of antibody treatment, and can include a fever, which may reach or exceed 40° C., nausea, fatigue, headache, tachycardia, hypotension, rash, shortness of breath, and/or myalgias. However, in certain cases, additional and potentially more serious complications may develop, including cardiac dysfunction, adult respiratory distress syndrome, neurological toxicity, renal and/or hepatic failure, and/or disseminated intravascular coagulation.

The National Cancer Institute Common Terminology Criteria for Adverse Events (CTCAE v. 5.0, pub. Nov. 27, 2017) includes a grading system for CRS.

Grade 1: Fever with or without constitutional symptoms.
Grade 2: Hypotension responding to fluids; hypoxia responding to <40% O2.
Grade 3: Hypotension managed with one pressor; hypoxia requiring ≥40% O2.
Grade 4: Life-threatening consequences; urgent intervention indicated.
Grade 5: Death.

The subject may not exhibit a sign or symptom of CRS and/or may be at risk of developing CRS. In such embodiments, administering the compound substantially prevents the onset of CRS, or prevents the onset of grade 2 or higher CRS.

Alternatively, the subject exhibits at least one sign or symptom of CRS and may exhibit at least one sign or symptom of grade 1 CRS. Or the subject may exhibit at least one sign or symptom of grade 2 or higher CRS, such as grade 3 or higher CRS. The disclosed compound(s) may be administered within 24 hours of the onset of the sign or symptom, and/or administering the compound(s) may ameliorate the sign or symptom of CRS, compared to the severity of the sign or symptom prior to administration of the compound(s), such as reducing the grade of CRS from 4 to 3, 2 or 1, or from 3, to 2 or 1, or from 2 to 1. Alternatively, CRS symptoms are substantially reduced to below grade 1 level, such that the subject no longer experiences symptoms associated with CRS. In some embodiments the sign or symptom is a fever and may be a fever of 40° C. or higher.

The disclosed compound(s)s may be administered to a subject that has previously be administered a first therapy for which CRS is a known, suspected, or potential side effect. Administration of the first therapy may be initiated from greater than zero to 10 days prior to administration of the compound(s). Alternatively, the compound(s) may be administered to a subject who will be, or is concurrently being, administered a first therapy for which CRS is a known, suspected, and/or potential side effect. The first therapy may comprise a cell therapy, including, but not limited to, chimeric antigen receptor (CAR)-expressing therapy and/or a transgenic receptor therapy. Cell-free antibodies are also known to elicit this syndrome, particularly those that activate T-cells, including, but not limited to, CAMPATH 1-H, blinatumomab, and/or rituximab.

A second therapeutic agent, for example, a steroid, an anti-inflammatory agent, an immunosuppressant, or a combination thereof, also may be administered to treat or prevent CRS. The steroid may be a corticosteroid, such as, for example, dexamethasone or prednisone, or a combination thereof. The disclosed compound(s) may be administered substantially simultaneously with the second therapeutic agent, or the compound(s) and second therapeutic agent may be administered sequentially in any order.

Acute respiratory distress syndrome (ARDS) is a syndrome characterized by a severe shortness of breath, labored and unusually rapid breathing, low blood pressure, confusion and extreme tiredness. This syndrome can be diagnosed based on a $PaO_2/FiO_2$ ratio of less than 300 mmHg despite a PEEP of more than 5 cm $H_2O$ (Fan et al JAMA. 319: 698-71).

ARDS occurs when fluid builds up in lung alveoli. The fluid prevents the lungs from filling with enough air, limiting the amount of oxygen that reaches the bloodstream which, in turn, deprives the organs of the oxygen they need to function. The symptoms of ARDS can vary in intensity, depending on its cause and severity. Severe shortness of breath—the hallmark of ARDS—usually develops within a few hours to a few days after the infection by some respiratory viruses, e.g., COVID-19 and influenza. Many people who develop ARDS do not survive, and the risk of death increases with age and severity of illness. If the patients that survive ARDS, some completely recover while others have lasting damage to their lungs. ARDS may be referred to as Acute Lung Injury (ALI) in some publications.

Acute kidney injury (AKI), also known as acute renal injury (ARI) or acute renal failure (ARF), is a syndrome characterized by an abrupt reduction of renal function including, e.g., the ability to excrete waste from a patient's blood. AKI is characterized by a decline of glomerular filtration rate, urine output, or both. This loss of filtration capacity results in retention of nitrogenous (urea and creatinine) and non-nitrogenous waste products that are normally excreted by the kidney, a reduction in urine output, or both. AKI may be categorized as prerenal, intrinsic renal, or postrenal in causation. Intrinsic renal disease can be further divided into glomerular, tubular, interstitial, and vascular abnormalities. AKI is accompanied by an inflammatory response that if unchecked can lead to renal fibrosis and chronic renal failure. AKI usually occurs over a period of hours or days and is potentially reversible. AKI may be characterized as an abrupt (i.e., for example, within 14 days, within 7 days, within 72 hours, or within 48 hours) reduction in kidney function identified by an absolute increase in serum creatinine of greater than or equal to 0.3 mg/dl (≥26.4 μmol/l), a percentage increase in serum creatinine of greater than or equal to 50% (1.5-fold from baseline), or a reduction in urine output (documented oliguria of less than 0.5 ml/kg per hour for at least 6 hours). Risk factors include, for example, a subject undergoing or having undergone major vascular surgery, coronary artery bypass, or other cardiac surgery; a subject having pre-existing congestive heart failure, preeclampsia, eclampsia, diabetes mellitus, hypertension, coronary artery disease, proteinuria, renal insufficiency, glomerular filtration below the normal range, cirrhosis, serum creatinine above the normal range, or sepsis; or a subject exposed to NSAIDs, cyclosporines, tacrolimus, aminoglycosides, foscarnet, ethylene glycol, hemoglobin, myoglobin, ifosfamide, heavy metals, methotrexate, radiopaque contrast agents, or streptozotocin. This list is not meant to be limiting.

Kidney malfunction includes, but is not limited to, kidney disorders, kidney disease, kidney dysfunction, kidney cancer, absence of at least one kidney due to accidents, surgical removal or genetic disorders, or other conditions where one or both of the kidneys are not properly functioning. Kidney malfunction may include acute kidney injury.

Thrombosis is a clotting disorder to which an excess of platelets contributes. Thrombosis may refer to the formation of a thrombus (blood clot) inside a blood vessel. The term encompasses, without limitation, arterial and venous thrombosis, including deep vein thrombosis, portal vein thrombosis, jugular vein thrombosis, renal vein thrombosis, stroke, myocardial infarction, Budd-Chiari syndrome, Paget-Schroetter disease, and cerebral venous sinus thrombosis. In some embodiments, the patient is at heightened risk relative to the general population (e.g., as measured by recognized risk factors) of a thrombotic event. In some embodiments, a patient has one or more risk factors that make the patient have a high risk of developing thrombosis relative to the general population. Risk factors for thrombosis include, e.g., classical cardiovascular disease risk factors: hyperlipidemia, smoking, diabetes, hypertension, and abdominal obesity; strong classical venous thromboembolism risk factors: trauma or fractures, major orthopedic surgery, and oncological surgery; moderate classical venous thromboembolism risk factors: non-oncological surgery, oral contraceptives and hormone replacement therapy, pregnancy and puerperium, hypercoagulability, and previous venous thromboembolism; and weak classical venous thromboembolism risk factors: age, bed rest (>3 days), prolonged travel, and metabolic syndrome. Additional risk factors include inherited, acquired and mixed coagulation or metabolic risk factors for thrombosis such as, e.g., inherited: antithrombin deficiency, protein C deficiency, Protein S deficiency, Factor V Leiden, Prothrombin G20210A; acquired: antiphospholipid syndrome; mixed: hyperhomocysteinaemia, increased fibrinogen levels, increased factor VIII levels, increased factor IX levels. In some cases, the use of heparin may increase the risk of thrombosis including, e.g., heparin-induced thrombocytopenia (HIT). Diseases and conditions associated with thrombosis include, without limitation, acute venous thrombosis, pulmonary embolism, thrombosis during pregnancy, hemorrhagic skin necrosis, acute or chronic disseminated intravascular coagulation (DIC), sepsis induced coagulopathy (SIC), clot formation from surgery, long bed rest, long periods of immobilization, venous thrombosis, fulminant meningococcemia, acute thrombotic stroke, acute coronary occlusion, acute peripheral arterial occlusion, massive pulmonary embolism, axillary vein thrombosis, massive iliofemoral vein thrombosis, occluded arterial cannulae, occluded venous cannulae, cardiomyopathy, venoocclusive disease of the liver, hypotension, decreased cardiac output, decreased vascular resistance, pulmonary hypertension, diminished lung compliance, leukopenia, thrombocytopenia (e.g., immune thrombocytopenia), and immune thrombocytic purpura. In a subject at risk for thrombosis, the subject may be monitored using methods known to those of skill in the art of maintaining hemostasis in patients at risk for thrombosis. Examples of methods for monitoring patients at risk of thrombosis included, without limitation, digital subtraction angiography, in vitro assays or non-invasive methods. Examples of in vitro assays useful for identifying and monitoring subjects at risk for thrombosis and for treatment using the present methods include, without limitation, functional assays and antibody detection assays.

Thrombotic event refers to any disorder which involves a blockage or partial blockage of an artery or vein with a thrombosis. A thrombotic event includes, but is not limited to, thrombotic disorders such as myocardial infarction, unstable angina, stroke, pulmonary embolism, transient ischemic attack, deep vein thrombosis, thrombotic re-occlusion and peripheral vascular thrombosis. A thrombotic event also includes thrombotic re-occlusion which occurs subsequent to a coronary intervention procedure or thrombolytic therapy.

COVID-19 is a disease caused by infection by SARS-CoV-2 (previously known as 2019-nCoV) which first appeared in Wuhan, China.

COVID-19-associated ARDS refers to ARDS that is caused by infection by SARS-CoV-2. Patients having COVID-19-associated ARDS may have been diagnosed as having a COVID-19, may have been exposed to another person having a COVID19, or may be suspected of having a COVID-19 based on their symptoms.

COVID-19-associated AKI refers to AKI that is caused by infection by SARS-CoV-2. Patients having COVID-19-associated AKI may have been diagnosed as having a COVID-19, may have been exposed to another person having a COVID-19, or may be suspected of having a COVID-19 based on their symptoms. In some cases, COVID-19-associated AKI includes AKI with the symptoms described, e.g., in Batlle et al. J. AM. SOC. NEPHROL. 2020, 31(7): 1380-1383 and Gabarre et al. Intensive Care Med. 2020, 46(7): 1339-1348, the disclosures of which are incorporated herein by reference in their entireties.

COVID-19-associated thrombosis refers to thrombosis that is caused by infection by SARS-CoV-2. Patients having COVID-19-associated thrombosis may have been diagnosed as having a COVID-19, may have been exposed to another person having a COVID-19, or may be suspected of having a COVID-19 based on their symptoms. In some cases, COVID-19-associated thrombosis includes any of the symptoms described in, e.g., Connors et al. Blood 2020, 135(23): 2033-2040 and Bikdeli et al. J. Am. Coll. Cardiol. 2020, 75(23): 2950-73, the disclosures of which are incorporated herein by reference in their entireties.

The term "associated with COVID-19" refers to a symptom or indication that typically develops within 28 days of hospitalization due to/signs of COVID-19.

For COVID-19-associated ARDS, successful treatment may include a decrease in shortness of breath, less labored or less rapid breathing, higher blood pressure, decreased confusion and/or a decrease tiredness. A treatment may be administered prophylactically, i.e., before the onset of ARDS. A prophylactic treatment prevents ARDS and can be administered to patients that have or are suspected of having a COVID-19 infection, but without the severe symptoms of ARDS. For example, prophylactic treatment can be administered to patients that have a cough without the other symptoms of ARDS.

For COVID-19-associated AKI, successful treatment may include increased kidney function. Kidney function may be assessed by measuring serum creatinine levels, serum creatinine clearance, or blood urea nitrogen levels. In some cases, the successful treatment includes a reduction in metabolic acidosis, hyperkalaemia, oliguria or anuria, azotemia, restoration in body fluid balance, and improved effects on other organ systems. A treatment may be administered prophylactically, i.e., before the onset of AKI. A prophylactic treatment prevents AKI and can be administered to patients that have or are suspected of having a COVID-19 infection, but without the severe symptoms of AKI. For example, prophylactic treatment can be administered to patients that have one or more of increased serum or urine creatinine, hematuria, hypoproteinemia, decreased antithrombin III levels, hypalbuminaemia, leucozyturia, or proteinuria without the other symptoms of AKI.

For COVID-19-associated thrombosis, successful treatment may include improvement in the subject's coagulation profile, or preventing, slowing, delaying, or arresting, a worsening of the coagulation profile for which the subject is at risk. A coagulation profile may be assessed by measurement of one or more coagulation parameters including, e.g., a subject's serum level of one or more of D-dimer, Factor II, Factor V (e.g., Factor V Leiden), Factor VII, Factor VIII, Factor IX, Factor XI, Factor XII, Factor XIII, F/fibrin degradation products, thrombin-antithrombin 111 complex, fibrinogen, plasminogen, prothrombin, and von Willebrand factor. Additional coagulation parameters that may be measured for the coagulation profile include, e.g., prothrombin time, thromboplastin time, activated partial thromboplast time (aPTT), antithrombin activity, platelet count, protein C levels, and protein S levels. In addition, the levels of C reactive protein may also be assessed in the patient prior to treatment and if elevated this may be used as a further indicator as to an increased risk of thrombosis in the patient.

Sepsis is a clinical syndrome of life-threatening organ dysfunction caused by a dysregulated immune response to infection. The more severe form of sepsis "septic shock" is characterized by a critical reduction in tissue perfusion; acute failure of multiple organs, including the lungs, kidneys, and liver. Common causes in immunocompetent patients include many different species of gram-positive and gram-negative bacteria. Immunocompromised patients may have uncommon bacterial or fungal species as a cause. Signs include fever, hypotension, oliguria, and confusion. Diagnosis is primarily clinical combined with culture results showing infection; early recognition and treatment is critical. Treatment is aggressive fluid resuscitation, antibiotics, surgical excision of infected or necrotic tissue and drainage of pus, and supportive care.

Influenza is a disease generally known as the "flu." Influenza is caused by a group of viruses that can be broken down into 4 separate groups: Influenza A, Influenza B, Influenza C and Influenza D which are separated based on their nuceloproteins and matrix proteins. Influenza causes viral respiratory infection resulting in fever, coryza, cough, headache, and malaise. Influenza A, B, and C all infect humans while there have been no documented cases of human Influenza D infection. Influenza C on the other hand does not cause typical influenza illness seen in individuals infected with Influenza A, B or C.

Influenza A strains are further classified based on two surface proteins, hemagglutinin (H) and neuraminidase (N). There are 18 different hemagglutinin subtypes and 11 different neuraminidase subtypes (H1 through H18 and N1 through N11, respectively). While there are potentially 198 different influenza A subtype combinations, only 131 subtypes have been detected in nature. Current subtypes of influenza A viruses that routinely circulate in people include: A(H1N1) and A(H3N2).

Cytokine release-related condition associated with influenza refers to any condition associated with influenza that leads to high levels of cytokine releases in the lungs and/or kidneys. Cytokine releases-related conditions, include without limitation, influenza-associated ARDS, influenza-associated AKI, influenza-associated thrombosis, influenza-associated sepsis, influenza-associated septic shock, etc.

Influenza-associated ARDS is ARDS that is caused by influenza infection. Patients having influenza-associated ARDS may have been diagnosed as having an influenza infection, may have been exposed to another person having an influenza infection, or may be suspected of having an influenza infection based on their symptoms.

Influenza-associated AKI is AKI that is caused by influenza infection. Patients having influenza-associated AKI may have been diagnosed as having an influenza infection, may have been exposed to another person having an influenza infection, or may be suspected of having an influenza infection based on their symptoms. In some cases, influenza-associated AKI includes AKI with the symptoms described, e.g., in Batlle et al. J. AM. SOC. NEPHROL. 2020, 31(7): 1380-1383 and Gabarre et al. Intensive Care Med. 2020, 46(7): 1339-1348, the disclosures of which are incorporated herein by reference in their entireties.

Influenza-associated thrombosis is thrombosis that is caused by influenza infection. Patients having influenza-associated thrombosis may have been diagnosed as having an influenza infection, may have been exposed to another person having an influenza infection, or may be suspected of having an influenza infection based on their symptoms. In some cases, influenza-associated thrombosis includes any of the symptoms described in, e.g., Connors et al. Blood 2020, 135(23): 2033-2040 and Bikdeli et al. J. Am. Coll. Cardiol. 2020, 75(23): 2950-73, the disclosures of which are incorporated herein by reference in their entireties.

Influenza-associated sepsis is sepsis that is caused by influenza infection. Patients having influenza-associated sepsis may have been diagnosed as having an influenza infection, may have been exposed to another person having an influenza infection, or may be suspected of having an influenza infection based on their symptoms. In some cases, influenza-associated thrombosis includes any of the symptoms described in, e.g., Florescu et al. Virulence. 2014 Jan. 1; 5(1): 137-142. and Gu et al. Eur Respir Rev. 2020 Jul. 21; 29(157):200038, the disclosures of which are incorporated herein by reference in their entireties.

The term "associated with influenza" refers to a symptom or indication that develops within 28 days of hospitalization/signs of influenza infection.

For influenza-associated ARDS, successful treatment may include a decrease in shortness of breath, less labored or less rapid breathing, higher blood pressure, decreased confusion and/or a decrease tiredness. A treatment may be administered prophylactically, i.e., before the onset of ARDS. A prophylactic treatment prevents ARDS and can be administered to patients that have or are suspected of having an influenza infection, but without the severe symptoms of ARDS. For example, prophylactic treatment can be administered to patients that have a cough without the other symptoms of ARDS.

For influenza-associated AKI, successful treatment may include increased kidney function. Kidney function may be assessed by measuring serum creatinine levels, serum creatinine clearance, or blood urea nitrogen levels. In some cases, the successful treatment includes a reduction in metabolic acidosis, hyperkalaemia, oliguria or anuria, azotemia, restoration in body fluid balance, and improved effects on other organ systems. A treatment may be administered prophylactically, i.e., before the onset of AKI. A prophylactic treatment prevents AKI and can be administered to patients that have or are suspected of having an influenza infection, but without the severe symptoms of AKI. For example, prophylactic treatment can be administered to patients that have one or more of increased serum or urine creatinine, hematuria, hypoproteinemia, decreased antithrombin III levels, hypalbuminaemia, leucozyturia, or proteinuria without the other symptoms of AKI.

For influenza-associated thrombosis, successful treatment may include improvement in the subject's coagulation profile, or preventing, slowing, delaying, or arresting, a worsening of the coagulation profile for which the subject is at risk. A coagulation profile may be assessed by measurement of one or more coagulation parameters including, e.g., a subject's serum level of one or more of D-dimer, Factor II, Factor V (e.g., Factor V Leiden), Factor VII, Factor VIII, Factor IX, Factor XI, Factor XII, Factor XIII, F/fibrin degradation products, thrombin-antithrombin 111 complex, fibrinogen, plasminogen, prothrombin, and von Willebrand factor. Additional coagulation parameters that may be measured for the coagulation profile include, e.g., prothrombin time, thromboplastin time, activated partial thromboplast time (aPTT), antithrombin activity, platelet count, protein C levels, and protein S levels. In addition, the levels of C reactive protein may also be assessed in the patient prior to treatment and if elevated this may be used as a further indicator as to an increased risk of thrombosis in the patient.

For influenza-associated sepsis or septic shock, successful treatment may include a reduction in fever, a reduction in high or moderately-high heartbeat (e.g. tachycardia), a reduction in sweating (i.e. diaphoresis), decreased confusion and/or a decrease tiredness, and/or a decrease in shortness of breath, less labored or less rapid breathing. A treatment may be administered prophylactically, i.e., before the onset of sepsis or septic shock. A prophylactic treatment prevents sepsis or septic shock and can be administered to patients that have or are suspected of having an influenza infection, but without the severe symptoms of sepsis or septic shock. For example, prophylactic treatment can be administered to patients that have a cough without the other symptoms of sepsis or septic shock.

Additionally, the disclosed compounds, combinations of disclosed compounds, or compositions thereof, may be used to treat sickle cell disease, particularly to reduce immunological responses that manifest in the disease. In some embodiments, the subject may exhibiting one or more of the following symptoms: anemia, sickle cell crisis, vaso-occlusive crisis, splenic sequestration crisis, splenic sequestration crises, acute chest syndrome, acute chest syndrome, aplastic crisis, hemolytic crisis, dactylitis, pneumonia, respiratory infection, bone-marrow embolization, or atelectasis.

Sickle cell disease (SCD) is a group of blood disorders typically inherited. The most common type is known as sickle cell anemia, which results in an abnormality in the oxygen carrying protein hemoglobin found in red blood cells. This leads to a rigid, sickle-like shape under certain circumstances. Problems in sickle cell disease typically begin around 5 to 6 months of age and a number of health problems may develop, such as attacks of pain (known as a sickle cell crisis), anemia, swelling in the hands and feet, bacterial infections and stroke. Long-term pain may develop as people get older.

Sickle cell disease occurs when a person inherits two abnormal copies of the (3-globin gene (HBB) that makes hemoglobin, one from each parent. That gene occurs in chromosome 11. Several subtypes exist, depending on the exact mutation in each hemoglobin gene. An attack can be set off by temperature changes, stress, dehydration, and high altitude.

The care of people with sickle cell disease may include infection prevention with vaccination and antibiotics, high fluid intake, folic acid supplementation, and pain medication. Tther measures may include blood transfusion and the medication hydroxycarbamide (hydroxyurea). A small percentage of people can be cured by a transplant of bone marrow cells. Patients with sickle cell disease may exhibit the following symptoms:

Sickle cell crisis: The terms "sickle cell crisis" or "sickling crisis" may be used to describe several independent acute conditions occurring in subjects with SCD, which results in anemia and crises that could be of many types, including the vaso-occlusive crisis, aplastic crisis, splenic sequestration crisis, hemolytic crisis, and others. Most episodes of sickle cell crises last between five and seven days. Although infection, dehydration, and acidosis (all of which favor sickling) can act as triggers, in most instances, no predisposing cause is identified.

Vaso-occlusive crisis: The vaso-occlusive crisis is caused by sickle-shaped red blood cells that obstruct capillaries and restrict blood flow to an organ, resulting in ischaemia, pain, necrosis, and often organ damage. The frequency, severity, and duration of these crises vary considerably. Painful crises are treated with hydration, analgesics, and blood transfusion; pain management requires opioid drug administration at regular intervals until the crisis has settled. For milder crises, a subgroup of subjects manages on nonsteroidal anti-inflammatory drugs such as diclofenac or naproxen. For more severe crises, most subjects require in-subject management for intravenous opioids; subject-controlled analgesia devices are commonly used in this setting. Vaso-occlusive crisis involving organs such as the penis or lungs are considered an emergency and treated with red blood cell transfusions. Incentive spirometry, a technique to encourage deep breathing to minimize the development of atelectasis, is recommended.

Splenic sequestration crisis: The spleen is frequently affected in sickle cell disease, as the sickle-shaped red blood cells cause narrowing of blood vessels and reduced function in clearing the defective cells. It is usually infarcted before the end of childhood in individuals with sickle cell anemia. This spleen damage increases the risk of infection from encapsulated organisms; preventive antibiotics and vaccinations are recommended for those lacking proper spleen function.

Splenic sequestration crises are acute, painful enlargements of the spleen, caused by intrasplenic trapping of red cells and resulting in a precipitous fall in hemoglobin levels with the potential for hypovolemic shock. Sequestration crises are considered an emergency. If not treated, subjects may die within 1-2 hours due to circulatory failure. Management is supportive, sometimes with blood transfusion. These crises are transient; they continue for 3-4 hours and may last for one day.

Acute chest syndrome: Acute chest syndrome is defined by at least two of these signs or symptoms: chest pain, fever, pulmonary infiltrate or focal abnormality, respiratory symptoms, or hypoxemia. It is the second-most common complication and it accounts for about 25% of deaths in subjects with SCD. Most cases present with vaso-occlusive crises, and then develop acute chest syndrome. Nevertheless, about 80% of people have vaso-occlusive crises during acute chest syndrome.

Aplastic crisis: Aplastic crises are instances of an acute worsening of the subject's baseline anemia, producing pale appearance, fast heart rate, and fatigue. This crisis is normally triggered by parvovirus B19, which directly affects production of red blood cells by invading the red cell precursors and multiplying in and destroying them. Parvovirus infection almost completely prevents red blood cell production for two to three days. In normal individuals, this is of little consequence, but the shortened red cell life of SCD subjects results in an abrupt, life-threatening situation. Reticulocyte counts drop dramatically during the disease (causing reticulocytopenia), and the rapid turnover of red cells leads to the drop in hemoglobin. This crisis takes 4 to 7 days to disappear. Most subjects can be managed supportively; some need a blood transfusion.

Hemolytic crisis: Hemolytic crises are acute accelerated drops in hemoglobin level. The red blood cells break down at a faster rate. This is particularly common in people with coexistent G6PD deficiency. Another influence of hemolytic crises in Sickle Cell Disease is oxidative stress on the erythrocytes, leukocytes, and platelets. When there is not enough red blood cell production in the bone marrow, the oxygen that the body receives, processes, and transports is unbalanced with the body's antioxidants. There is an imbalance in the oxygen reactive species in the cells, which leads to more production of red blood cells that are not properly oxygenated or formed. Txidative stress may lead to anemia because of the imbalance of oxygen in the tissue. Management is supportive, sometimes with blood transfusions.

In addition, one of the earliest clinical manifestations is dactylitis, presenting as early as six months of age, and may occur in children with sickle cell trait. The crisis can last up to a month. Given that pneumonia and sickling in the lung can both produce symptoms of acute chest syndrome, the subject is treated for both conditions. It can be triggered by painful crisis, respiratory infection, bone-marrow embolization, or possibly by atelectasis, opiate administration, or surgery. Hematopoietic ulcers may also occur.

Additionally, the disclosed compounds, combinations of disclosed compounds, or compositions thereof, may be used to treat a lung injury. The lung injury may be a chemical- or radiation-induced lung injury.

In some embodiments, the subject may have inhaled or may be expected to be exposed to a pulmonary irritant. In some embodiments, the subject may have inhaled or may be expected to inhale a choking agent. A pulmonary agent, or choking agent, is a chemical agent designed to impede a subject's ability to breathe. These compounds generally operate by causing a build-up of fluids in the lungs, which then leads to suffocation. Inhalation of these agents cause burning of the throat, coughing, vomiting, headache, pain in chest, tightness in chest, and respiratory and circulatory failure. Examples of such agents include: chlorine gas, chloropicrin (PS), diphosgene (DP), phosgene (CG), disulfur decafluoride, perfluoroisobutene, acrolein, and piphenylcyanoarsine. Phosgene-induced acute lung injury (P-ALI) is commonly associated with short-term phosgene inhalation. Prolonged exposure can cause chronic hypoventilation, refractory pulmonary edema, and other associated lung injuries, ultimately resulting in ARDS. Chemical pneumonitis is inflammation of the lungs or breathing difficulty due to inhaling chemical fumes or breathing in and choking on certain chemicals.

Additionally, the disclosed compounds, combinations of disclosed compounds, or compositions thereof, may be used to treat or prevent acute inhalation injury (AII) and e-cigarette, or vaping, product use-associated lung injury (EVALI).

In other embodiments, the subject has been exposed to or is expected to be exposed to ionizing radiation. In these embodiments, the subject may have or may be expected to develop radiation induced lung injury (RILI). In some embodiments, the subject may have radiation pneumonitis or radiation pulmonary fibrosis. In these embodiments, the subject may have received or is undergoing thoracic radiotherapy, may have inhaled a radioactive agent or may have had direct exposure to ionizing radiation. For example, the subject may have inhaled a radioactive agent or have had direct exposure to ionizing radiation as a result of a nuclear weapon or leak at a nuclear power plant, for example.

The disclosed compounds, combinations of disclosed compounds, or compositions thereof, also may be used to treat or prevent hemorrhagic fever, or symptoms thereof, including Ebola virus disease, Alkhurma hemorrhagic fever, Chapare hemorrhagic fever, Crimean-Congo hemorrhagic fever, Hantavirus Pulmonary Syndrome (HPS), Hemorrhagic fever with renal syndrome (HFRS), Kyasanur Forest Disease (KFD), Lassa fever, Lujo hemorrhagic fever, Marburg hemorrhagic fever, Omsk hemorrhagic fever, Rift Valley fever, Yellow Fever, or Dengue fever, such as severe dengue fever (dengue hemorrhagic fever).

B. Formulations and Administration

Pharmaceutical compositions comprising one or more active compounds of the disclosure may be manufactured by any suitable method, such as mixing, dissolving, granulating, dragee-making, levigating, emulsifying, encapsulating, entrapping or lyophilization processes. The compositions may be formulated using one or more physiologically acceptable excipients, diluents, carriers, adjuvants or auxiliaries to provide preparations which can be used pharmaceutically.

The active compound(s) may be formulated in the pharmaceutical compositions per se, or in the form of a hydrate, solvate, N-oxide or pharmaceutically acceptable salt. Typically, such salts are more soluble in aqueous solutions than the corresponding free acids and bases, but salts having lower solubility than the corresponding free acids and bases may also be formed.

Pharmaceutical compositions comprising the disclosed compound(s) may take a form suitable for virtually any mode of administration, including, for example, topical, ocular, oral, buccal, systemic, nasal, injection, such as i.v. or i.p., transdermal, rectal, vaginal, etc., or a form suitable for administration by inhalation or insufflation.

For topical administration, the active compound(s) (or a hydrate, solvate, N-oxide or pharmaceutically acceptable salt thereof) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions, or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile, pyrogen-free water, buffer, dextrose solution, etc., before use. To this end, the active compound(s) maybe dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients, such as: binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); and/or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable excipients such as: suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases, such as cocoa butter or other glycerides.

For nasal administration or administration by inhalation or insufflation, the active compound(s), hydrate, solvate, N-oxide, or pharmaceutically acceptable salt can be conveniently delivered in the form of an aerosol spray from pressurized packs or a nebulizer with the use of a suitable propellant, e.g.,) dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

The pharmaceutical compositions can be in the form of a sterile injectable aqueous or oleagenous suspension. This suspension can be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that can be employed are water, Ringer's solution and isotonic sodium chloride solution.

According to the present disclosure, a form of the disclosed compound(s), solvates, N-oxides, pharmaceutically acceptable salts or prodrug(s) thereof, can also be delivered by any of a variety of inhalation devices and methods known in the art, including, for example: U.S. Pat. Nos. 6,241,969; 6,060,069; 6,238,647; 6,335,316; 5,364,838; 5,672,581; WO96/32149; WO95/24183; U.S. Pat. Nos. 5,654,007; 5,404,871; 5,672,581; 5,743,250; 5,419,315; 5,558,085; WO98/33480; U.S. Pat. Nos. 5,364,833; 5,320,094; 5,780,014; 5,658,878; 5,518,998; 5,506,203; 5,661,130; 5,655,523; 5,645,051; 5,622,166; 5,577,497; 5,492,112; 5,327,883; 5,277,195; U.S. Publication No. 20010041190; U.S. Publication No. 20020006901; and U.S. Publication No. 20020034477.

Included among the devices which can be used to administer a form of the active compound(s) are those well-known in the art, such as, metered dose inhalers, liquid nebulizers, dry powder inhalers, sprayers, thermal vaporizers, and the like. Tther suitable technology for administration of particular 2,4-pyrimidinediamine compounds includes electrohydrodynamic aerosolizers.

In addition, the inhalation device is preferably practical, in the sense of being easy to use, small enough to carry conveniently, capable of providing multiple doses, and durable. Some specific examples of commercially available inhalation devices are Turbohaler (Astra, Wilmington, DE), Rotahaler (Glaxo, Research Triangle Park, NC), Diskus (Glaxo, Research Triangle Park, NC), the Ultravent nebulizer (Mallinckrodt), the Acorn II nebulizer (Marquest Medical Products, Totowa, NJ) the Ventolin metered dose inhaler (Glaxo, Research Triangle Park, NC), or the like. In one embodiment, the disclosed compound(s), solvates, N-oxides, pharmaceutically acceptable salts or prodrug(s) thereof can be delivered by a dry powder inhaler or a sprayer.

As those skilled in the art will recognize, the formulation of the form of the disclosed compound(s), solvates, N-oxides, pharmaceutically acceptable salts or prodrug(s) thereof, the quantity of the formulation delivered, and the duration of administration of a single dose depend on the type of inhalation device employed as well as other factors. For some aerosol delivery systems, such as nebulizers, the frequency of administration and length of time for which the system is activated will depend mainly on the concentration of the disclosed compound(s) in the aerosol. For example, shorter periods of administration can be used at higher concentrations the disclosed compound(s) in the nebulizer solution. Devices such as metered dose inhalers can produce higher aerosol concentrations, and can be operated for shorter periods to deliver the desired amount of active compound in some embodiments. Devices such as dry powder inhalers deliver active agent until a given charge of agent is expelled from the device. In this type of inhaler, the amount of the disclosed compound(s), solvates, N-oxides, pharmaceutically acceptable salts or prodrug(s) thereof in a given quantity of the powder determines the dose delivered in a single administration. The formulation of the disclosed compound(s) is selected to yield the desired particle size in the chosen inhalation device.

Formulations of a disclosed compound for administration from a dry powder inhaler may typically include a finely divided dry powder containing the disclosed compound(s), but the powder can also include a bulking agent, buffer, carrier, excipient, another additive, or the like. Additives can be included in a dry powder formulation, for example, to dilute the powder as required for delivery from the particular powder inhaler, to facilitate processing of the formulation, to provide advantageous powder properties to the formulation, to facilitate dispersion of the powder from the inhalation device, to stabilize to the formulation (e.g., antioxidants or buffers), to provide taste to the formulation, or the like. Typical additives include mono-, di-, and polysaccharides;

sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like.

The disclosed method can be conducted a pharmaceutical composition including the disclosed compound(s) suitable for administration by inhalation. For example, a dry powder formulation can be manufactured in several ways, using conventional techniques, such as described in any of the publications mentioned above and incorporated expressly herein by reference, and for example, Baker, et al., U.S. Pat. No. 5,700,904, the entire disclosure of which is incorporated expressly herein by reference. Particles in the size range appropriate for maximal deposition in the lower respiratory tract can be made by micronizing, milling, or the like. And a liquid formulation can be manufactured by dissolving the compound in a suitable solvent, such as water, at an appropriate pH, including buffers or other excipients.

A specific example of an aqueous suspension formulation suitable for nasal administration using commercially-available nasal spray devices includes the following ingredients: active compound (0.5 20 mg/ml); benzalkonium chloride (0.1 0.2 mg/mL); polysorbate 80 (TWEEN® 80; 0.5 5 mg/ml); carboxymethylcellulose sodium or microcrystalline cellulose (1 15 mg/ml); phenylethanol (1 4 mg/ml); and dextrose (20 50 mg/ml). The pH of the final suspension can be adjusted to range from about pH 5 to pH 7, with a pH of about pH 5.5 being typical.

Another specific example of an aqueous suspension suitable for administration of the compounds via inhalation contains 20 mg/mL of the disclosed compound(s), 1% (v/v) polysorbate 80 (TWEEN® 80), 50 mM citrate and/or 0.9% sodium chloride.

For ocular administration, the active compound(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776, 445; 5,698,219; 5,521,222; 5,403,841; 5,077,033; 4,882, 150; and 4,738,851, which are incorporated herein by reference.

For prolonged delivery, the active compound(s) can be formulated as a depot preparation for administration by implantation or intramuscular injection. The active ingredient maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352, 456; 5,332,213; 5,336,168; 5,290,561; 5,254,346; 5,164, 189; 5,163,899; 5,088,977; 5,087,240; 5,008,110; and 4,921, 475, which are incorporated herein by reference.

Alternatively, other pharmaceutical delivery systems may be employed. Liposomes and emulsions are well-known examples of delivery vehicles that may be used to deliver active compound(s). Certain organic solvents, such as dimethylsulfoxide (DMSO), may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

C. Dosages

The disclosed compound or combinations of disclosed compounds will generally be used in an amount effective to achieve the intended result, for example, in an amount effective to treat, prevent or ameliorate a particular condition. The disclosed compound(s), or compositions thereof, can be administered therapeutically to achieve therapeutic benefit or prophylactically to achieve a prophylactic benefit. Therapeutic benefit means eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. Therapeutic benefit also includes halting or slowing the progression of the disease, regardless of whether improvement is realized.

As known by those of ordinary skill in the art, the preferred dosage of disclosed compounds may depend on various factors, including the age, weight, general health, and severity of the condition of the patient or subject being treated. Dosage also may need to be tailored to the sex of the individual and/or the lung capacity of the individual, when administered by inhalation. Dosage may also be tailored to individuals suffering from more than one condition or those individuals who have additional conditions that affect lung capacity and the ability to breathe normally, for example, emphysema, bronchitis, pneumonia, and respiratory infections. Dosage, and frequency of administration of the disclosed compound(s) or compositions thereof, will also depend on whether the disclosed compound(s) are formulated for treatment of acute episodes of a condition or for the prophylactic treatment of a disorder. A person of ordinary skill in the art will be able to determine the optimal dose for a particular individual.

For prophylactic administration, the disclosed compound, combinations of disclosed compounds, or compositions thereof, can be administered to a patient or subject at risk of developing one of the previously described conditions. For example, if it is unknown whether a patient or subject is allergic to a particular drug, the disclosed compound, combinations of disclosed compounds, or compositions thereof, can be administered prior to administration of the drug to avoid or ameliorate an allergic response to the drug. Alternatively, prophylactic administration can be used to avoid or ameliorate the onset of symptoms in a patient diagnosed with the underlying disorder. For example, a disclosed compound(s), or composition thereof, can be administered to an allergy sufferer prior to expected exposure to the allergen. A disclosed compound, combinations of disclosed compounds, or compositions thereof, can also be administered prophylactically to healthy individuals who are repeatedly exposed to agents known to one of the above-described maladies to prevent the onset of the disorder. For example, a disclosed compound, combinations of disclosed compounds, or compositions thereof, can be administered to a healthy individual who is repeatedly exposed to an allergen known to induce allergies, such as latex, in an effort to prevent the individual from developing an allergy. Alternatively, a disclosed compound, combinations of disclosed compounds, or compositions thereof, can be administered to a patient suffering from asthma prior to partaking in activities which trigger asthma attacks to lessen the severity of, or avoid altogether, an asthmatic episode.

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound. Fingl & Woodbury, "General Principles," In: Goodman and Gilman's The Pharmaceutical Basis of Therapeutics, Chapter 1, pages 1-46, Pergamon Press, and the references cited therein, provide additional guidance concerning effective dosages.

In some embodiments, the disclosed compounds have an $EC_{50}$ with respect to a kinase protein, such as an IRAK protein, of from greater than 0 to 20 PM, such as from greater than 0 to 10 µM, from greater than 0 to 5 µM, from greater than 0 to 1 µM, from greater than 0 to 0.5 µM, from greater than 0 to 0.1 µM, or from greater than 0 to 0.05 µM.

Initial dosages can also be estimated from in vivo data, such as animal models.

Animal models useful for testing the efficacy of compounds to treat or prevent the various diseases described above are well-known in the art. Suitable animal models of hypersensitivity or allergic reactions are described in Foster, (1995) Allergy 50(21Suppl): 6-9, discussion 34-38 and Tumas et al., (2001), J. Allergy Clin. Immunol. 107(6):1025-1033. Suitable animal models of allergic rhinitis are described in Szelenyi et al., (2000), Arzneimittelforschung 50(11):1037-42; Kawaguchi et al., (1994), Clin. Exp. Allergy 24(3):238-244 and Sugimoto et al., (2000), Immunopharmacology 48(1):1-7. Persons of ordinary skill in the art can adapt such information to determine dosages suitable for human administration.

Dosage amounts of disclosed compounds will typically be in the range of from about greater than 0 mg/kg/day, such as 0.0001 mg/kg/day or 0.001 mg/kg/day or 0.01 mg/kg/day, up to at least about 100 mg/kg/day. More typically, the dosage (or effective amount) may range from about 0.0025 mg/kg to about 1 mg/kg administered at least once per day, such as from 0.01 mg/kg to about 0.5 mg/kg or from about 0.05 mg/kg to about 0.15 mg/kg. The total daily dosage typically ranges from about 0.1 mg/kg to about 5 mg/kg or to about 20 mg/kg per day, such as from 0.5 mg/kg to about 10 mg/kg per day or from about 0.7 mg/kg per day to about 2.5 mg/kg/day. Dosage amounts can be higher or lower depending upon, among other factors, the activity of the disclosed compound, its bioavailability, the mode of administration, and various factors discussed above.

Dosage amount and dosage interval can be adjusted for individuals to provide plasma levels of the disclosed compound that are sufficient to maintain therapeutic or prophylactic effect. For example, the compounds can be administered once per day, multiple times per day, once per week, multiple times per week (e.g., every other day), one per month, multiple times per month, or once per year, depending upon, amongst other things, the mode of administration, the specific indication being treated, and the judgment of the prescribing physician. Persons of ordinary skill in the art will be able to optimize effective local dosages without undue experimentation.

Compositions comprising one or more of the disclosed compounds typically comprise from greater than 0 up to 99% of the disclosed compound, or compounds, and/or other therapeutic agent by total weight percent. More typically, compositions comprising one or more of the disclosed compounds comprise from about 1 to about 20 total weight percent of the disclosed compound and other therapeutic agent, and from about 80 to about 99 weight percent of a pharmaceutically acceptable excipient. Typical daily administrations may be in the range of 100-300 mg/day, e.g., 100, 150, 200, 250, or 300 mg/day. Administration may be once or twice daily or more, e.g., 100 or 150 mg BID. Accordingly, pharmaceutical dosage forms comprising a compound disclosed herein may contain from 50-300 mg of the disclosed compound, e.g., 50, 100, 150, 200, 250, 300 mg of the disclosed compound.

Preferably, the disclosed compound, combinations of disclosed compounds, or compositions thereof, will provide therapeutic or prophylactic benefit without causing substantial toxicity. Toxicity of the disclosed compound can be determined using standard pharmaceutical procedures. The dose ratio between toxic and therapeutic (or prophylactic) effect is the therapeutic index. Disclosed compounds that exhibit high therapeutic indices are preferred.

VII. Examples

Example 1

3-(dimethylamino)-1-(pyrimidin-2-yl)prop-2-en-1-one (D-2)

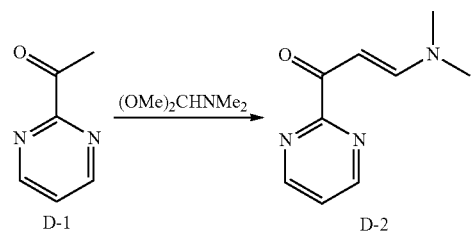

1,1-Dimethoxy-N,N-dimethylmethanamine (11 mL, 81.9 mmol) solution of 1-(pyrimidin-2-yl)ethan-1-one (D-1, 5 g, 40.95 mmol) was stirred at 90° C. overnight. The reaction went to completion as monitored by LCMS. Volatiles were removed in vacuo, and the crude product was used in next reaction without further purification: $^1$H NMR (400 MHz, Chloroform-d) δ 8.89 (d, J=4.9 Hz, 2H), 8.00 (d, J=10.3 Hz, 1H), 7.35 (dd, J=4.9, 4.9 Hz, 1H), 6.39 (d, J=10.3 Hz, 1H), 3.20 (s, 3H), 3.00 (s, 3H); LRMS (M+H) m/z 178.2.

Example 2

2-(1H-pyrazol-3-yl)pyrimidine (D-3)

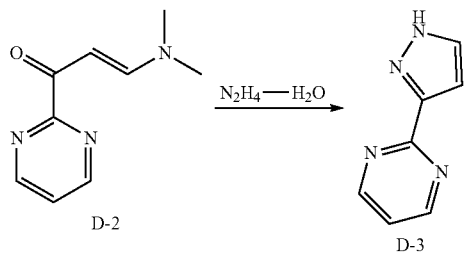

Hydrazine monohydrate solution (64-65% aqueous, 2.8 mL, ~0.9 eq) was added to an EtOH (15 mL) solution of 3-(dimethylamino)-1-(pyrimidin-2-yl)prop-2-en-1-one (D-2, 41 mmol), with cooling in an ice bath. After refluxing for 3 hours, the reaction went to completion as monitored by LCMS. Volatiles were removed in vacuo, and the crude product was used in next reaction without further purification; $^1$H NMR (400 MHz, Chloroform-d) δ 11.20 (br s, 1H), 8.79 (d, J=4.9 Hz, 2H), 7.71 (d, J=2.0 Hz, 1H), 7.22 (dd, J=4.9, 4.9 Hz, 1H), 7.08 (d, J=2.0 Hz, 1H); LRMS (M+H) m/z 147.1.

Example 3

2-(4-nitro-1H-pyrazol-3-yl)pyrimidine (D-4)

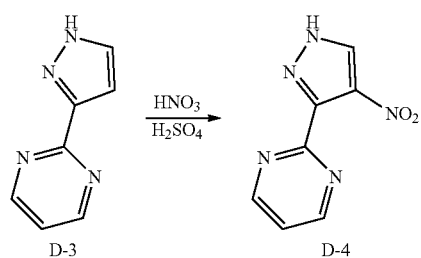

90% Fuming nitric acid (3.8 mL, 81.9 mmol) was added dropwise to a conc. H$_2$SO$_4$ (10 mL) suspension of 2-(1H-pyrazol-3-yl)pyrimidine (D-3, ~41 mmol), with cooling in an ice bath. Upon complete addition of the nitric acid, the mixture was stirred at 70° C. overnight. The reaction went to completion as monitored by LCMS. After cooling to room temperature, the mixture was carefully poured onto ice-water. The pH was adjusted to 8 with NaOH aqueous solution, and the product was extracted with EtOAc (100 mL×5). The combined organic layers were dried (Na$_2$SO$_4$), filtered, and the solvent was removed in vacuo. After silica gel chromatography purification, compound 2-(4-nitro-1H-pyrazol-3-yl)pyrimidine (D-4) was obtained as an off-white solid: 5.6 g (71.5% yield over 3 steps); $^1$H NMR (400 MHz, Chloroform-d) δ 11.26 (br s, 1H), 8.90 (d, J=4.9 Hz, 2H), 8.28 (s, 1H), 7.40 (dd, J=4.9, 4.9 Hz, 1H); LRMS (M+H) m/z 192.1.

Alternative Procedure:

To a conc. H$_2$SO$_4$ (200 mL) suspension of 2-(1H-pyrazol-3-yl)pyrimidine (D-3, 32.6 g, 223 mmol), was added fuming nitric acid (100 mL) dropwise, and the reaction mixture was stirred at room temperature overnight. The mixture was carefully poured onto ice, and 27N NaOH aqueous solution was added to adjust pH to 6. Solid was collected by filtration, washed with water, and dried in vacuo. Compound 2-(4-nitro-1H-pyrazol-3-yl)pyrimidine was obtained as an off-white solid: 29.2 g (69% yield).

Example 4

8-ethoxy-1,4-dioxaspiro[4.5]decane (B-2)

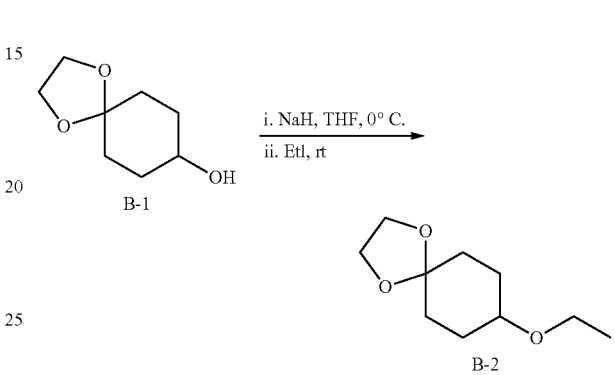

A solution of 1,4-dioxaspiro[4.5]decanol B-1 (158 g, 1.0 mol, 1.0 eq) in tetrahydrofuran (500 mL) was added to a suspension of hexane-washed sodium hydride (48 g of a 60% suspension in mineral oil, 1.2 mol, 1.2 eq) in tetrahydrofuran (500 mL) at 0° C. The reaction stirred at 0° C. for 15 minutes and room temperature for 4 hours before cooling to 0° C. and adding iodoethane (104.5 mL, 1.3 mol, 1.3 eq). The reaction was stirred at 0° C. for 10 minutes and room temperature 14 hours. The reaction was quenched by the careful addition of NH$_4$Cl (approximately 100 mL). The reaction was concentrated to remove tetrahydrofuran and the concentrate partitioned between EtOAc (800 mL) and water (600 mL). The aqueous phase was extracted with EtOAc (300 mL). The combined organics were washed with NaHCO$_3$ (500 mL) and brine (500 mL), dried (Na$_2$SO$_4$) and concentrated under reduced pressure to yield the title compound (177 g, 95%) as an orange oil, which was used without purification; $^1$H nmr (400 MHz, CD$_3$Cl) δ 3.90, 3.89 (4H, 2d AB system, J 2.5 Hz, OCH$_2$CH$_2$O), 3.44 (2H, q, J 7.0 Hz, OCH$_2$CH$_3$), 3.35 (1H, tt, J 7.5, 3.0 Hz, H-8), 1.82-1.74 (4H, m, 4H of H-6, H-7, H-9, H-10), 1.70-1.63 (2H, m, 2H of H-6, H-7, H-9, H-10), 1.54-1.47 (2H, m, 2H of H-6, H-7, H-9, H-10), 1.15 (3H, t, J 7.0 Hz, OCH$_2$CH$_3$).

Example 5

4-ethoxycyclohexan-1-one (B-3)

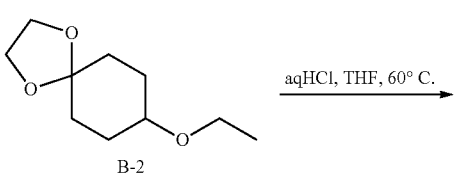

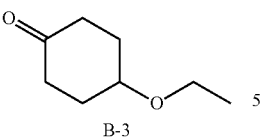

B-3

Hydrochloric acid (450 mL of a 3M solution) was added to a solution of the dioxalane B-2 (177 g, 952 mmol) in tetrahydrofuran (450 mL). The reaction was stirred vigorously at 60° C. for 20 hours. NMR analysis suggested 75% completion. Further hydrochloric acid (100 mL of a 4M solution) was added and the reaction stirred at 60° C. for a further 24 hours before cooling and concentrating to remove tetrahydrofuran. The organics were extracted with EtOAc (3×400 mL). The combined organics were washed with brine (400 mL), dried (Na$_2$SO$_4$) and concentrated under reduced pressure to yield the title compound (142.2 g, theoretical yield 135.1 g) as an orange oil; $^1$H nmr (400 MHz, CD$_3$Cl) δ 3.71 (1H, m, cyclohexaneH-4), 3.55 (2H, q, J 7.0 Hz, OCH$_2$CH$_3$), 2.58 (2H, ddd, J 15.5, 10.5, 6.0 Hz, 2H of cyclohexaneH-2, H-6), 2.25 (2H, m, 2H of cyclohexaneH-2, H-6), 2.10-2.02 (2H, m, 2H of cyclohexaneH-3, H-5), 1.98-1.90 (2H, m, 2H of cyclohexaneH-3, H-5), 1.24 (3H, t, J 7.0 Hz, OCH$_2$CH$_3$).

Example 6

(1s,4s)-4-ethoxycyclohexan-1-ol (B-4)

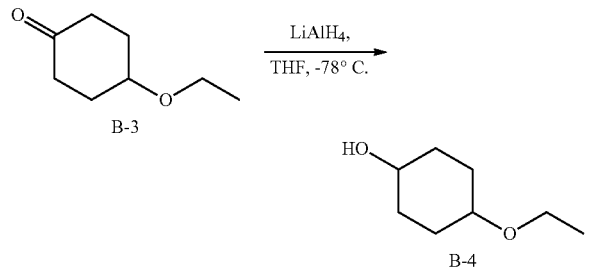

A solution of the ketone B-3 (146.2 g, 1.0 eq) in tetrahydrofuran (300 mL) was cooled to −78° C. Lithium aluminum hydride (400 mL of a 1M solution in tetrahydrofuran, 400 mmol, 0.4 eq) was added dropwise over 90 minutes. The reaction was stirred at −78° C. for a further 30 minutes and the reaction quenched by the dropwise addition of NaOH (1M, 300 mL) initially at −78° C. before removing from the cold bath. A gel resulted. The reaction was diluted with EtOAc (400 mL) and stirred before decanting to remove the gel. The decanted organics were washed with Rochelle's salt (400 mL), back-extracting the aqueous phase with EtOAc (200 mL). The combined organics were washed with Rochelle's salt (300 mL) and brine (400 mL), dried (Na$_2$SO$_4$) and concentrated under reduced pressure to obtain the title compound (131.1 g) as an orange oil without purification; $^1$H nmr (400 MHz, CD$_3$Cl) δ 3.74 (1H major, m, cyclohexaneH-1), 3.68 (1H minor, m, cyclohexaneH-1), 3.48 (2H minor, J 7.0 Hz, OCH$_2$CH$_3$), 3.47 (2H minor, J 7.0 Hz, OCH$_2$CH$_3$), 3.37 (1H major, tt, J 6.5, 3.0 Hz, H-4), 3.25 (1H minor, m, H-4), 1.99 (1H, m, 1H of H-2, H-3, H-5, H-6), 1.81 (2H, m, 2H of H-2, H-3, H-5, H-6), 1.73-1.51 (5H, m, 5H of H-2, H-3, H-5, H-6), 1.19 (3H major, t, J 7.0 Hz, OCH$_2$CH$_3$), 1.19 (3H minor, J 7.0 Hz, OCH$_2$CH$_3$).

Example 7

(1r,4r)-4-ethoxycyclohexyl 4-nitrobenzenesulfonate (B-5)

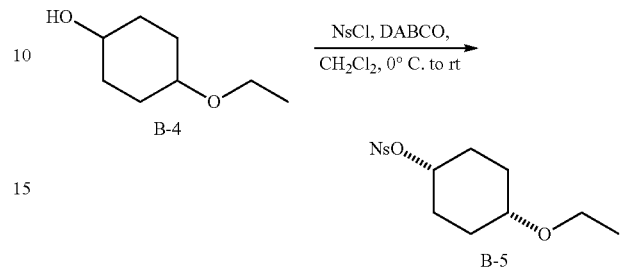

To a solution of 4-ethoxycyclohexan-1-ol B-4 (112.9 g as an approximately 2:1 ratio of the 1s,4s and 1r,4s diastereomers, 782.9 mmol, 1.0 eq) in dichloromethane (800 mL) at 0° C. was added 1,4-diazabicyclo[2.2.2]octane (105.4 g, 939.5 mmol, 1.2 eq). 4-Nitrobenzenesulfonyl chloride (190.8 g, 861.2 mmol, 1.1 eq) was added portionwise at 0° C. over 1 hour and the reaction allowed to warm to room temperature over 16 hours. The reaction was diluted with CH$_2$Cl$_2$ (400 mL) and washed with NaHCO$_3$ (1 L), water (1 L) and brine (1 L). The organics were dried (Na$_2$SO$_4$) and concentrated under reduced pressure. The resulting solid was triturated from ethyl acetate and hexanes to yield 160.8 g of 4-ethoxycyclohexyl 4-nitrobenzenesulfonate (as a mixture of 1r,4r and 1s,4s) as an off-white solid; $^1$H nmr (400 MHz, CD$_3$Cl) δ 8.39 (2H, d, J 9.0 Hz, 2H of C$_6$H$_4$NO$_2$), 8.11 (2H, d, J 9.0 Hz, 2H of C$_6$H$_4$NO$_2$), 4.75 (1H major, tt, J 7.5, 3.5 Hz, H-1), 4.70 (1H minor, m, H-1), 3.45 (2H minor, J 7.0 Hz, OCH$_2$CH$_3$), 3.44 (2H major, J 7.0 Hz, OCH$_2$CH$_3$), 3.34 (1H, tt, J 6.5, 3.0 Hz, H-4), 1.99-1.88 (3H, m, 3H of H-2, H-3, H-5, H-6), 1.80-1.71 (1H, m, 1H of H-2, H-3, H-5, H-6), 1.67-1.56 (3H, m, 3H of H-2, H-3, H-5, H-6), 1.48-1.40 (1H, m, 1H of H-2, H-3, H-5, H-6), 1.17 (3H major, t, J 7.0 Hz, OCH$_2$CH$_3$), 1.16 (3H minor, J 7.0 Hz, OCH$_2$CH$_3$).

Example 8

2-(1-(trans-4-ethoxycyclohexyl)-4-nitro-1H-pyrazol-3-yl)pyrimidine (E-1)

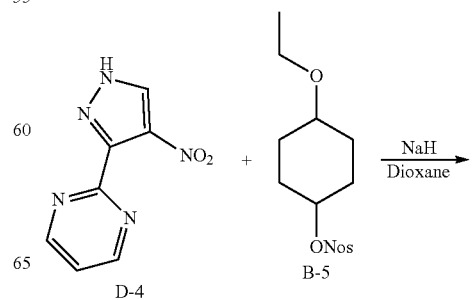

57
-continued

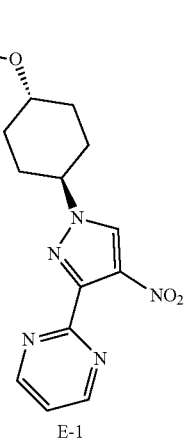

E-1

Under a nitrogen atmosphere and with cooling in an ice bath, NaH (60% dispersion in Mineral Oil, 1.68 g, 42 mmol) was added portion-wise to a 1,4-Dioxane (150 mL, 0.2 M) suspension of 2-(4-nitro-1H-pyrazol-3-yl)pyrimidine (D-4, 5.73 g, 30 mmol). After removal of the ice bath, the suspension was stirred at 25° C. After 3 hours, compound 4-ethoxycyclohexyl 4-nitrobenzenesulfonate (B-5, 11.86 g, 36 mmol, with cis/trans ratio ≥2) was added, and the reaction mixture was stirred at 100° C. with gentle reflux. After 19 hours, another about 0.4 eq (5 g) of B-5 was added and the reaction continued. Reaction progress was monitored by LC-MS and it was stopped at day 4. After cooling to room temperature, the reaction was quenched with NaHCO$_3$ sat. Aq. solution (100 mL), and most of the dioxane was removed by rotary evaporation under reduced pressure. The product was extracted with EtOAc (150 mL) which was further washed with brine. The organic layer was dried (Na$_2$SO$_4$), filtered, and the solvent was removed by rotary evaporation under reduced pressure. The product was purified by silica gel chromatography, followed by trituration from hexanes-EtOAc (8 mL-2 mL, 35° C., overnight, then collected as a precipitate at room temperature). Compound 2-(1-(trans-4-ethoxycyclohexyl)-4-nitro-1H-pyrazol-3-yl)pyrimidine (E-1) was obtained as an off-white solid: 1.98 g (21% yield); $^1$H NMR (400 MHz, Chloroform-d) δ 8.89 (d, J=4.9 Hz, 2H), 8.24 (s, 1H), 7.37 (dd, J=4.9, 4.9 Hz, 1H), 4.27 (tt, J=11.8, 3.9 Hz, 1H), 3.55 (q, J=7.0 Hz, 1H), 3.35 (tt, J=10.7, 4.2 Hz, 1H), 2.35-2.29 (m, 2H), 2.26-2.20 (m, 2H), 1.94-1.83 (m, 2H), 1.50-1.40 (m, 2H), 1.22 (t, J=7.0 Hz, 3H); LRMS (M+H) m/z 318.3.

58

Example 9

1-(trans-4-ethoxycyclohexyl)-3-(pyrimidin-2-yl)-1H-pyrazol-4-amine

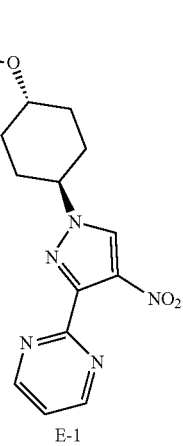

E-1

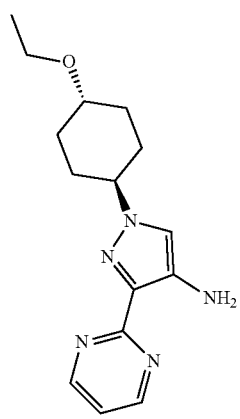

In a Parr flask, under 15 psi of Hydrogen, a MeOH (30 mL) solution of 2-(1-(trans-4-ethoxycyclohexyl)-4-nitro-1H-pyrazol-3-yl)pyrimidine (E-1, 974.2 mg, 3.07 mmol) and Pd—BaSO$_4$ (5% Pd on BaSO$_4$, 450 mg) was shaken at room temperature for 4 hours. The reaction went to completion as monitored by LC-MS. Under nitrogen atmosphere, the reaction mixture was passed through a celite pad, which was further washed with MeOH. Filtrate was collected and solvent was removed in vacuo. Compound 1-(trans-4-ethoxycyclohexyl)-3-(pyrimidin-2-yl)-1H-pyrazol-4-amine was obtained as a light yellow solid (used in next reaction without further purification); $^1$H NMR (400 MHz, Chloroform-d) δ 8.75 (d, J=4.9 Hz, 2H), 7.09-7.06 (m, 2H), 4.56 (br s, 2H), 4.20 (tt, J=12.1, 3.7 Hz, 1H), 3.54 (q, J=7.0 Hz, 2H), 3.33 (tt, J=10.7, 4.0 Hz, 1H), 2.26-2.17 (m, 4H), 1.88-1.78 (m, 2H), 1.47-1.36 (m, 2H), 1.21 (t, J=7.0, Hz, 3H); LRMS (M+H) m/z 288.3.

Example 10

N-(1-(trans-4-ethoxycyclohexyl)-3-(pyrimidin-2-yl)-1H-pyrazol-4-yl)-2-(1H-pyrazol-4-yl)oxazole-4-carboxamide (I-1)

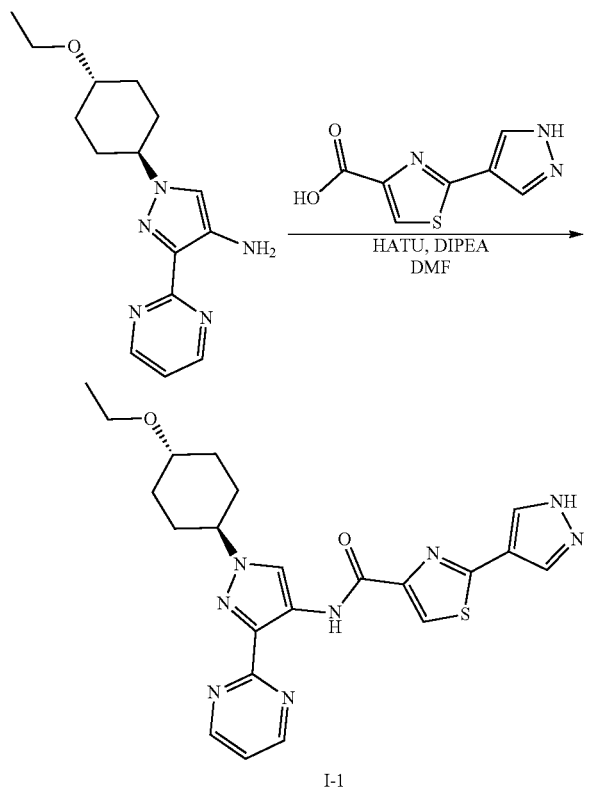

2-(1H-pyrazol-4-yl)thiazole-4-carboxylic acid (599.2 mg, 3.07 mmol) was added to a DMF (12 mL) solution of 1-(trans-4-ethoxycyclohexyl)-3-(pyrimidin-2-yl)-1H-pyrazol-4-amine (3.07 mmol) with cooling in an ice bath, followed by HATU (1.28 g, 3.38 mmol) after 30 minutes. After another 1 hour, N-ethyl-N-isopropylpropan-2-amine (DIPEA, 1.6 mL, 9.2 mmol) was added dropwise. The ice bath was removed, and the mixture was stirred at room temperature for 16 hours. The reaction was quenched by dropwise addition of NaHCO$_3$ sat. aq. solution (300 mL), and after 1 hour the precipitate was collected by filtration, washed with H$_2$O, then dried in vacuo. A yellow color solid (about 1.17 g) was obtained and was dissolved in CH$_2$Cl$_2$-MeOH (10:1). The solution was then passed through a silica gel pad to remove darker color impurities. Compound N-(1-(trans-4-ethoxycyclohexyl)-3-(pyrimidin-2-yl)-1H-pyrazol-4-yl)-2-(1H-pyrazol-4-yl)oxazole-4-carboxamide (I-1) was obtained as a light yellow solid: 1.10 g (77% yield); $^1$H NMR (400 MHz, Chloroform-d) δ 12.04 (s, 1H), 11.10 (v br s, 1H), 8.90 (d, J=4.9 Hz, 2H), 8.49 (s, 1H), 8.16 (s, 2H), 8.10 (s, 1H), 7.23 (dd, J=4.9, 4.9 Hz, 1H), 4.34 (tt, J=12.0, 3.9 Hz, 1H), 3.56 (q, J=7.0 Hz, 2H), 3.37 (tt, J=10.8, 4.2 Hz, 1H), 2.33-2.29 (m, 2H), 2.25-2.20 (m, 2H), 2.00-1.89 (m, 2H), 1.51-1.41 (m, 2H), 1.22 (t, J=7.0 Hz, 3H); $^{13}$C NMR (101 MHz, Chloroform-d) δ 161.47, 160.21, 158.35, 157.15, 150.29, 136.25, 132.67, 122.71, 121.86, 119.89, 118.68, 117.15, 76.33, 63.62, 61.83, 31.09, 31.01, 15.65; LRMS (M+H) m/z 465.4.

The compound was used without further purification to make the tartrate salt/co-crystal and for pro-drug synthesis. Additionally, if required, the compound is further purified by silica gel chromatography or RP-HPLC.

Example 11

Alternative Synthesis of I-1

A. 2-bromo-N-(1-(trans-4-ethoxycyclohexyl)-3-(pyrimidin-2-yl)-1H-pyrazol-4-yl)thiazole-4-carboxamide (E-2)

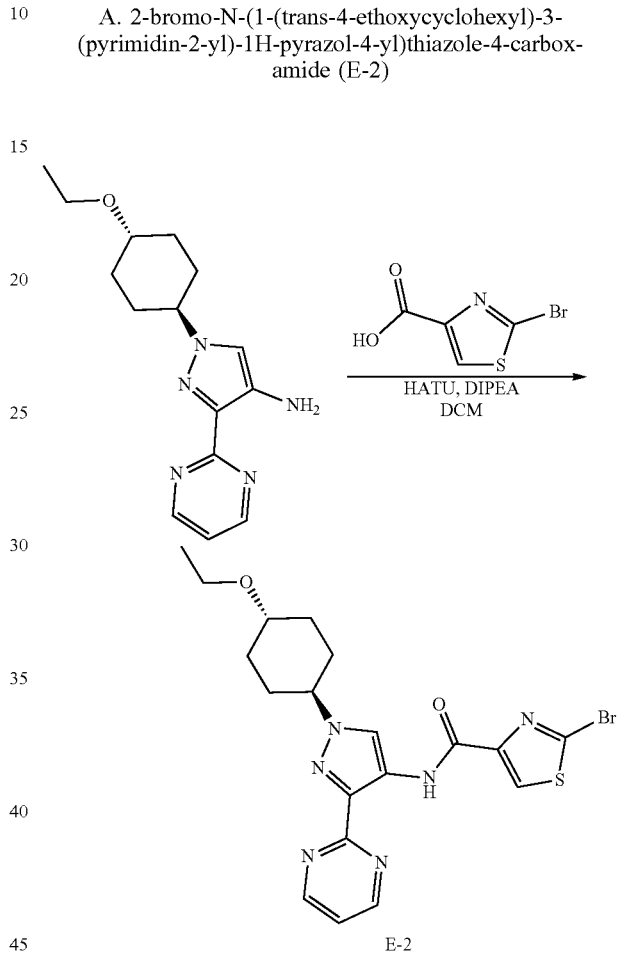

A CH$_2$Cl$_2$ (20 mL) solution of 2-bromothiazole-4-carboxylic acid (298 mg, 1.43 mmol) and HATU (572 mg, 1.50 mmol) was stirred at room temperature for 15 minutes. N-ethyl-N-isopropylpropan-2-amine (0.623 mL, 3.58 mmol) was added with cooling in an ice bath, followed by a CH$_2$Cl$_2$ (5 mL) solution of 1-(trans-4-ethoxycyclohexyl)-3-(pyrimidin-2-yl)-1H-pyrazol-4-amine (452 mg, 1.576 mmol). The reaction mixture was stirred at room temperature for 17 hours, after which time LC-MS indicated that the reaction was complete. The reaction was quenched by addition of NaHCO$_3$ sat. aq. solution, and stirring was continued for 30 minutes. Two layers were separated, and organic layer was washed again with NaHCO$_3$ sat. aq. solution, dried over Na$_2$SO$_4$, filtered, and the solvent was removed by rotary evaporation under reduce pressure. After silica gel chromatography, compound 2-bromo-N-(1-(trans-4-ethoxycyclohexyl)-3-(pyrimidin-2-yl)-1H-pyrazol-4-yl)thiazole-4-carboxamide (E-2) was obtained as a white solid: 581.1 mg (85% yield); $^1$H NMR (400 MHz, Chloroform-d) δ 8.89 (d, J=4.9 Hz, 2H), 8.42 (s, 1H), 8.12 (s, 1H), 7.22 (dd, J=4.9, 4.9 Hz, 1H), 4.33 (tt, J=12.0, 3.9 Hz, 1H), 3.56 (q, J=7.0 Hz, 2H), 3.36 (tt, J=10.8, 4.2 Hz, 1H), 2.32-2.28 (m, 2H), 2.24-2.20 (m, 2H), 1.99-1.89 (m, 2H), 1.50-1.41 (m, 2H), 1.22 (t, J=7.0 Hz, 3H); LRMS (M+H) m/z 477.3, 479.3.

B. N-(1-(trans-4-ethoxycyclohexyl)-3-(pyrimidin-2-yl)-1H-pyrazol-4-yl)-2-(1H-pyrazol-4-yl)oxazole-4-carboxamide (I-1)

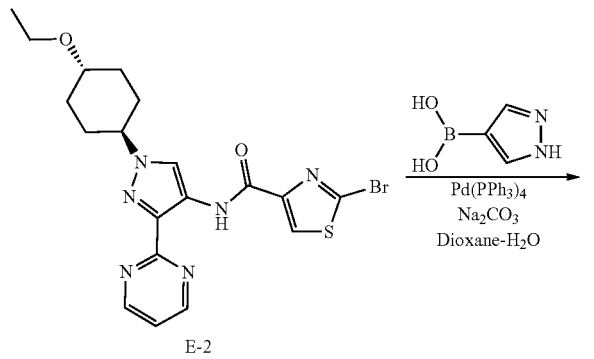

A 1,4-dioxane-H$_2$O (4 mL-1 mL) suspension of 2-bromo-N-(1-(trans-4-ethoxycyclohexyl)-3-(pyrimidin-2-yl)-1H-pyrazol-4-yl)thiazole-4-carboxamide (E-2, 477.4 mg, 1 mmol), (1H-pyrazol-4-yl)boronic acid (279.8 mg, 2.5 mmol), Na$_2$CO$_3$ (318 mg, 3 mmol) and tetrakis(triphenylphosphine)palladium(0) (28 mg, 0.02 mmol) was degassed and then back-filled with nitrogen, three times. The mixture was heated at 90° C. under nitrogen atmosphere for 21.5 hours, after which time, LC-MS indicated that the reaction was complete. Most of the dioxane was removed by rotary evaporation under reduced pressure, and the crude product was mixed with water and NaHCO$_3$ sat aq. solution until free-flowing solid appeared. The solid was collected by filtration, washed with H$_2$O, and then stirred in hexane-EtOAc-EtOH (1 mL-3 mL-0.5 mL) at 35° C. over a weekend. The solid product was collected by filtration, washed with ice-cold hexane-EtOAc (~1:1), and dried in vacuo. Compound N-(1-(trans-4-ethoxycyclohexyl)-3-(pyrimidin-2-yl)-1H-pyrazol-4-yl)-2-(1H-pyrazol-4-yl)oxazole-4-carboxamide (I-1) was obtained as a light beige color solid: 287.1 mg (62% yield); $^1$H NMR (400 MHz, Chloroform-d) δ 12.04 (s, 1H), 11.10 (v br s, 1H), 8.90 (d, J=4.9 Hz, 2H), 8.49 (s, 1H), 8.16 (s, 2H), 8.10 (s, 1H), 7.23 (dd, J=4.9, 4.9 Hz, 1H), 4.34 (tt, J=12.0, 3.9 Hz, 1H), 3.56 (q, J=7.0 Hz, 2H), 3.37 (tt, J=10.8, 4.2 Hz, 1H), 2.33-2.29 (m, 2H), 2.25-2.20 (m, 2H), 2.00-1.89 (m, 2H), 1.51-1.41 (m, 2H), 1.22 (t, J=7.0 Hz, 3H); LRMS (M+H) m/z 465.4.

Example 12

N-(1-(trans-4-ethoxycyclohexyl)-3-(pyrimidin-2-yl)-1H-pyrazol-4-yl)-2-(1H-pyrazol-4-yl)thiazole-4-carboxamide (2R,3R)-2,3-dihydroxysuccinic acid (I-4; tartaric acid salt/co-crystal of I-1)

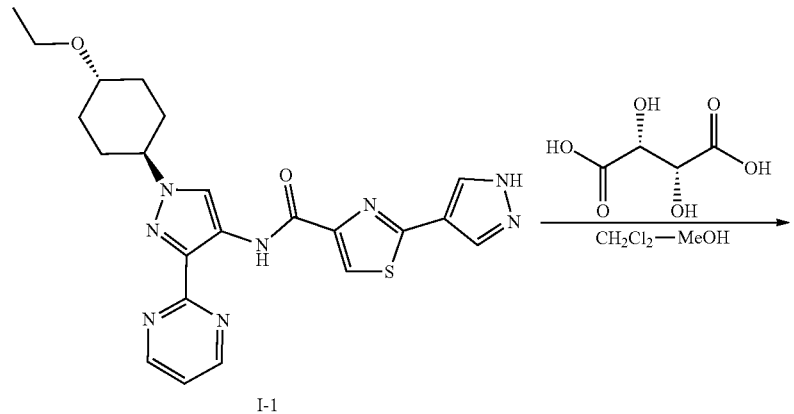

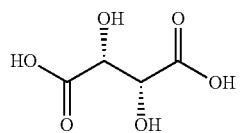
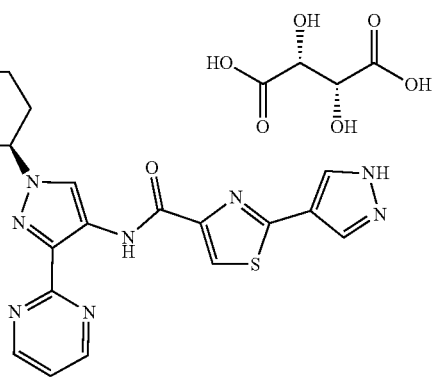

I-4

A CH₂Cl₂-MeOH (12 mL-1 mL) solution of N-(1-(trans-4-ethoxycyclohexyl)-3-(pyrimidin-2-yl)-1H-pyrazol-4-yl)-2-(1H-pyrazol-4-yl)oxazole-4-carboxamide (I-1, 1.10 g, 2.37 mmol) and (L)-Tartaric Acid (177.9 mg, 1.19 mmol) was stirred at 35° C. for 18 hours. Another 12 mL of CH₂Cl₂ was added, and stirring was continued for additional 5 hours. After cooling to room temperature, the precipitate was collected by filtration, washed with ice-cold CH₂Cl₂, and dried in vacuo. The product was obtained as pale yellow solid: 702.7 mg; ¹H NMR (400 MHz, DMSO-d₆) δ 13.41 (br s, 1H), 12.68 (br s, 2H), 11.93 (s, 1H), 8.98 (d, J=4.9 Hz, 2H), 8.52 (v br s, 1H), 8.50 (s, 1H), 8.31 (s, 1H), 8.13 (v br s, 1H), 7.49 (dd, J=4.9, 4.9 Hz, 1H), 5.08 (br s, 2H), 4.39-4.31 (m, 3H), 3.50 (q, J=7.0 Hz, 2H), 3.41-3.31 (m, overlapped with H₂O, 1H), 2.13-2.06 (m, 4H), 1.96-1.86 (m, 2H), 1.41-1.32 (m, 2H), 1.12 (t, J=7.0 Hz, 3H); ¹³C NMR (101 MHz, DMSO-d₆) δ 173.14, 161.27, 160.61, 157.55, 157.31, 149.07, 135.61, 132.61, 123.08, 121.86, 120.21, 119.46, 115.64, 75.64, 72.13, 62.58, 60.34, 30.60, 30.50, 15.67; LRMS (M+H) m/z 465.5.

For the filtrate: after removal of solvent, material was re-dissolved in CH₂Cl₂-MeOH (12 mL-1 mL), and additional (L)-Tartaric Acid (177.9 mg, 1.19 mmol) was added. After similar reaction and work-up procedures, another crop of product was obtained as a light yellow solid: 280.9 mg, with same ¹H NMR as 1ˢᵗ crop. Combined total: 983.6 mg, 68% yield.

Example 13 di-tert-butyl ((4-(4-((1-(trans-4-ethoxycyclohexyl)-3-(pyrimidin-2-yl)-1H-pyrazol-4-yl)carbamoyl)oxazol-2-yl)-1H-pyrazol-1-yl)methyl) phosphate tert-butyl ((4-(4-((1-(trans-4-ethoxycyclohexyl)-3-(pyrimidin-2-yl)-1H-pyrazol-4-yl)carbamoyl)thiazol-2-yl)-1H-pyrazol-1-yl)methyl) hydrogen phosphate

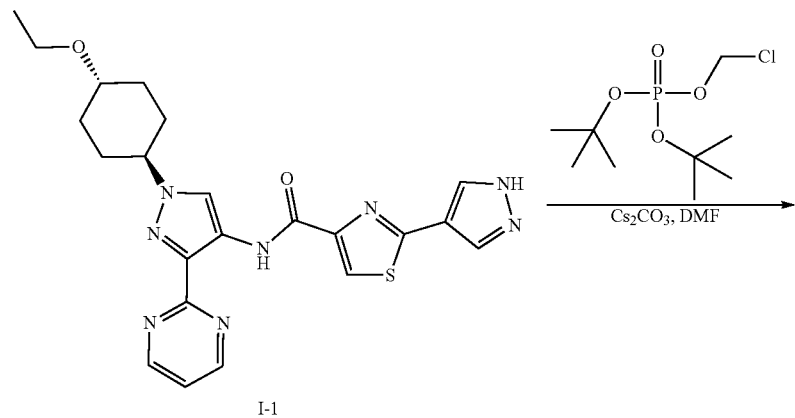

I-1

-continued

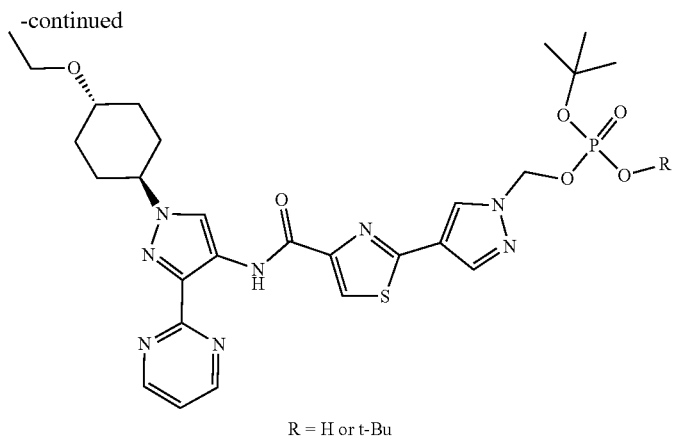

R = H or t-Bu

Cs$_2$CO$_3$ (495 mg, 1.52 mmol) was added to a DMF (5 mL) solution of N-(1-(trans-4-ethoxycyclohexyl)-3-(pyrimidin-2-yl)-1H-pyrazol-4-yl)-2-(1H-pyrazol-4-yl)oxazole-4-carboxamide (I-1, 470.6 mg, 1.01 mmol) at room temperature. After 10 minutes, di-tert-butyl (chloromethyl) phosphate (524 mg, 2.03 mmol) was added. After 22 hours, the major peak on the LC-MS was desired product (m/z 687.7 (M+H)), with <5% of compound I-1 remaining. With cooling in an ice bath, the reaction was quenched by dropwise addition of water (60 mL), and stirring was continued at room temperature. After 3 hours the product was extracted with CH$_2$Cl$_2$ (50 mL×2). The combined organic layers were dried (Na$_2$SO$_4$), filtered, and the solvent was removed in vacuo. A light brown oil was obtained, and appeared to be mainly mono-$^t$Bu product: 635 mg; $^1$H NMR (400 MHz, Chloroform-d) δ 11.97 (s, 1H), 8.88 (d, J=4.9 Hz, 2H), 8.01-8.00 (m, 3H), 7.97 (s, 1H), 7.25 (dd, J=4.9, 4.9 Hz, 1H), 5.96 (d, J=12.1 Hz, 2H), 4.32 (tt, J=11.8, 3.9 Hz, 1H), 3.57 (q, J=7.0 Hz, 2H), 3.37 (tt, J=10.7, 4.2 Hz, 1H), 2.33-2.30 (m, 2H), 2.25-2.21 (m, 2H), 1.99-1.89 (m, 2H), 1.45 (s, partially overlapped, 9H), 1.51-1.36 (m, partially overlapped, 2H), 1.23 (t, J=7.0 Hz, 3H); $^{31}$P NMR (162 MHz, Chloroform-d) 6-5.03; LRMS (M+H) m/z 631.6.

The aqueous layer was adjusted to pH 2 with 1N HCl (aq), and the precipitate was collected, which was further washed with H$_2$O to give 55.3 mg of a bright yellow solid, which was mainly acid by LCMS.

From a different reaction with similar work-up procedures, di-$^t$Bu product was obtained from organic layer: $^1$H NMR (400 MHz, Chloroform-d) δ 12.08 (s, 1H), 8.96 (d, J=4.9 Hz, 2H), 8.47 (s, 1H), 8.35 (s, 1H), 8.09 (s, 1H), 8.08 (s, 1H), 7.25 (dd, J=4.9, 4.9 Hz, 1H), 5.96 (d, J=13.2 Hz, 2H), 4.34 (tt, J=11.6, 3.8 Hz, 1H), 3.56 (q, J=7.0 Hz, 2H), 3.37 (tt, J=10.4, 4.5 Hz, 1H), 2.33-2.30 (m, 2H), 2.24-2.20 (m, 2H), 2.00-1.89 (m, 4H), 1.50-1.41 (m, partially overlapped, 2H), 1.44 (s, partially overlapped, 18H), 1.22 (t, J=7.0 Hz, 3H); LRMS (M+H) m/z 687.7.)

Example 14

(4-(4-((1-(trans-4-ethoxycyclohexyl)-3-(pyrimidin-2-yl)-1H-pyrazol-4-yl)carbamoyl)thiazol-2-yl)-1H-pyrazol-1-yl)methyl dihydrogen phosphate (I-2)

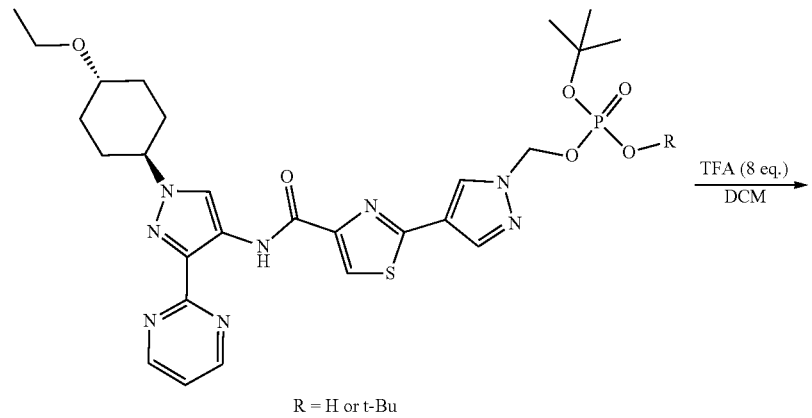

R = H or t-Bu

TFA (8 eq.)
DCM

-continued

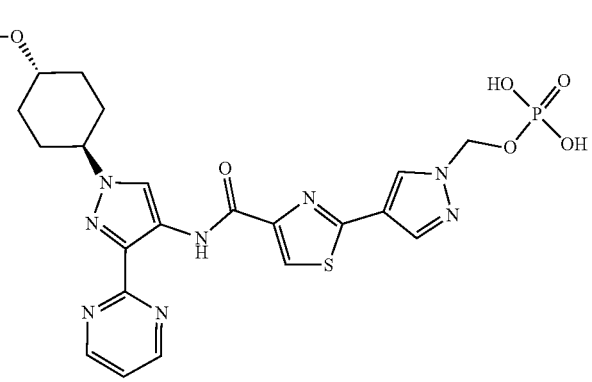

I-2

Trifluoroacetic acid (TFA) (0.613 mL, 8 mmol) was added to a CH$_2$Cl$_2$ (7 mL) solution of tert-butyl ((4-(4-((1-(trans-4-ethoxycyclohexyl)-3-(pyrimidin-2-yl)-1H-pyrazol-4-yl)carbamoyl)thiazol-2-yl)-1H-pyrazol-1-yl)methyl) hydrogen phosphate (635 mg, 1 mmol) with cooling in an ice bath, and the stirring was continued at room temperature. After 2 hours, LC-MS indicated that the reaction was complete. Volatiles were removed in vacuo, and a light brown oil was obtained. The crude product was suspended in acetone-H$_2$O (10:1, 12 mL) at 35° C. for 15 hours. The solid was collected by filtration, washed with acetone, and then further suspended in CH$_2$Cl$_2$ (5 mL) at room temperature for 1 hour. The precipitate was collected by filtration, washed with CH$_2$Cl$_2$ and dried in vacuo. Compound (4-(4-((1-(trans-4-ethoxycyclohexyl)-3-(pyrimidin-2-yl)-1H-pyrazol-4-yl)carbamoyl)thiazol-2-yl)-1H-pyrazol-1-yl)methyl dihydrogen phosphate (I-2) was obtained as a light yellow solid: 277.6 mg (52% yield); $^1$H NMR (400 MHz, DMSO-d$_6$) δ 11.97 (s, 1H), 11.62 (v br s, 1H), 9.02 (d, J=4.9 Hz, 2H), 8.63 (d, J=0.8 Hz, 1H), 8.49 (s, 1H), 8.36 (s, 1H), 8.20 (d, J=0.8 Hz, 1H), 7.46 (dd, J=4.9, 4.9 Hz, 1H), 5.92 (d, J=11.2 Hz, 2H), 4.35 (tt, J=11.5, 3.7 Hz, 1H), 3.50 (q, J=7.0 Hz, 2H), 3.37 (tt, J=10.7, 3.8 Hz, 1H), 2.13-2.07 (m, 4H), 1.96-1.85 (m, 2H), 1.41-1.31 (m, 2H), 1.12 (t, J=7.0 Hz, 3H); $^{31}$P NMR (162 MHz, DMSO-d$_6$) δ −2.17; LRMS (M+H) m/z 575.5.

Example 15 sodium (4-(4-((1-(trans-4-ethoxycyclohexyl)-3-(pyrimidin-2-yl)-1H-pyrazol-4-yl)carbamoyl)thiazol-2-yl)-1H-pyrazol-1-yl)methyl phosphate (I-3)

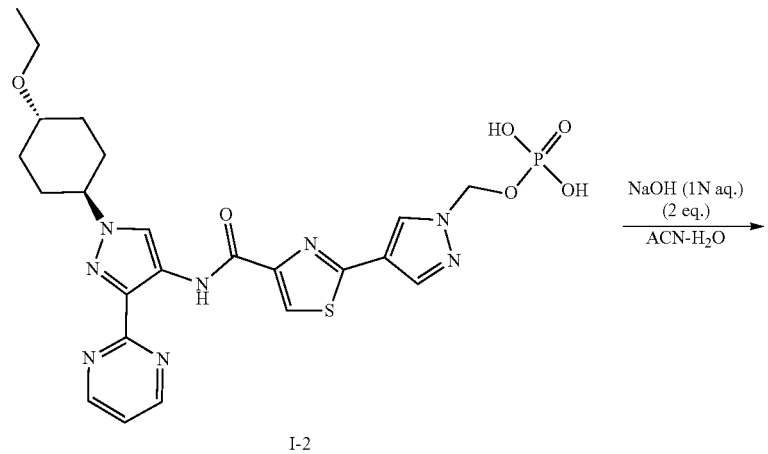

I-2

-continued

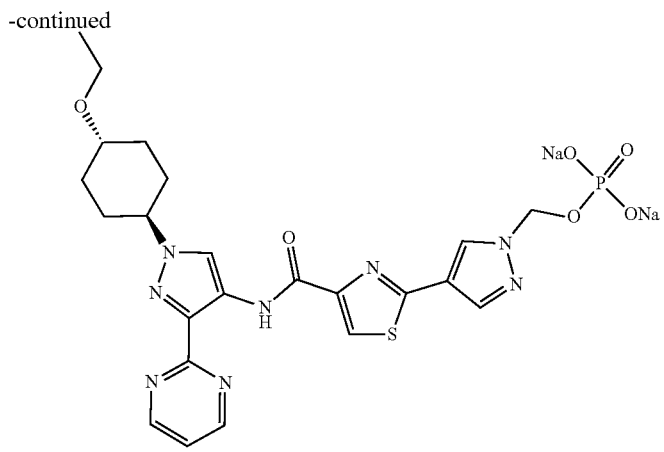

I-3

1N NaOH solution (0.9 mL, 0.9 mmol) was added dropwise to a CH₃CN (2 mL) and H₂O (2 mL) suspension of (4-(4-((1-(trans-4-ethoxycyclohexyl)-3-(pyrimidin-2-yl)-1H-pyrazol-4-yl)carbamoyl)thiazol-2-yl)-1H-pyrazol-1-yl)methyl dihydrogen phosphate (I-2, 258.5 mg, 0.45 mmol) with cooling in an ice bath, until pH=8 was obtained. Stirring was continued for another 10 minutes at room temperature, and the solvent was removed by lyophilization. Compound sodium (4-(4-((1-(trans-4-ethoxycyclohexyl)-3-(pyrimidin-2-yl)-1H-pyrazol-4-yl)carbamoyl)thiazol-2-yl)-1H-pyrazol-1-yl)methyl phosphate (I-3) was obtained as a cream color solid: 278 mg (99% yield); ¹H NMR (400 MHz, Deuterium Oxide) δ 8.63 (d, J=5.0 Hz, 2H), 8.23 (s, 1H), 8.10 (s, 1H), 7.81 (s, 1H), 7.74 (s, 1H), 7.27 (dd, J=5.0, 5.0 Hz, 1H), 5.74 (d, J=6.8 Hz, 2H), 4.21 (br t, J=12.1 Hz, 1H), 3.73 (q, J=7.1 Hz, 2H), 3.69-3.59 (m, 1H), 2.31-2.23 (m, 4H), 1.93-1.84 (m, 2H), 1.53-1.44 (m, 2H), 1.25 (t, J=7.1 Hz, 3H); ³¹P NMR (162 MHz, Deuterium Oxide) δ 2.10; LRMS (M+H) m/z 575.4.

Example 16

1,3-dihydroxy-2-(hydroxymethyl)propan-2-aminium (4-(4-((1-(trans-4-ethoxycyclohexyl)-3-(pyrimidin-2-yl)-1H-pyrazol-4-yl)carbamoyl)thiazol-2-yl)-1H-pyrazol-1-yl)methyl hydrogen phosphate (I-5)

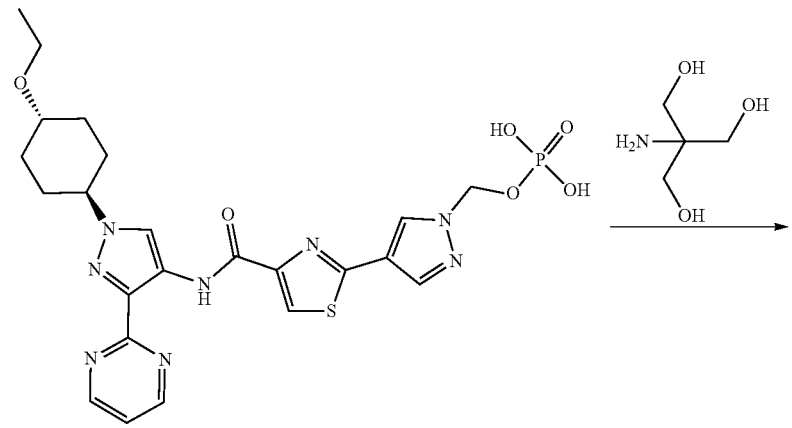

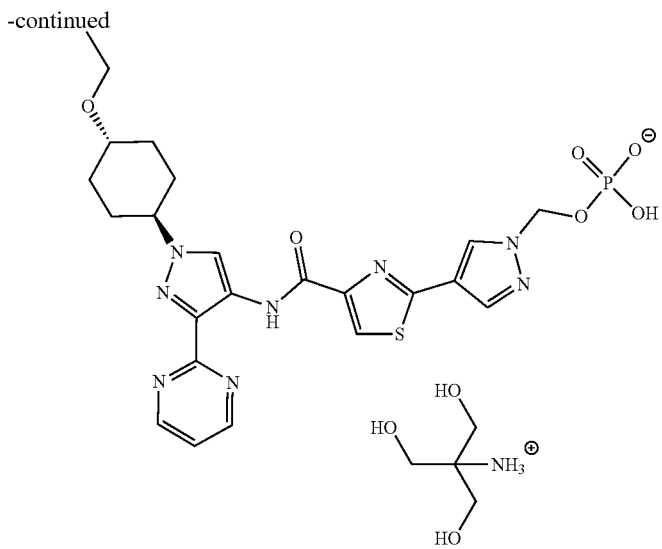

To an i-PrOH—H₂O (0.2 mL-0.2 mL) suspension of (4-(4-((1-(trans-4-ethoxycyclohexyl)-3-(pyrimidin-2-yl)-1H-pyrazol-4-yl)carbamoyl)thiazol-2-yl)-1H-pyrazol-1-yl)methyl dihydrogen phosphate (I-2, 25 mg, 0.0435 mmol), 2-amino-2-(hydroxymethyl)propane-1,3-diol (5.4 mg, 0.044 mmol) was added, and the thin suspension was stirred at 30° C. overnight. After cooling to room temperature, additional i-PrOH was added (0.2 mL, then up to 0.5 mL), and the mixture remained cloudy without free-flowing precipitate. After removing most organic solvent by rotary evaporation under reduced pressure, mixture was re-suspended in i-PrOH-ACN—H₂O until white solid appeared. After filtration, the collected (hygroscopic) solid was dissolved in water and solvent was removed in vacuo. Title compound 1,3-dihydroxy-2-(hydroxymethyl)propan-2-aminium (4-(4-((1-(trans-4-ethoxycyclohexyl)-3-(pyrimidin-2-yl)-1H-pyrazol-4-yl)carbamoyl)thiazol-2-yl)-1H-pyrazol-1-yl) methyl hydrogen phosphate (I-5) was obtained as an off-white solid: 15.2 mg (50% yield); $^1$H NMR (400 MHz, Deuterium Oxide) δ 8.45 (d, J=4.9 Hz, 2H), 8.01 (s, 1H), 7.92 (s, 1H), 7.60 (s, 1H), 7.51 (s, 1H), 7.13 (dd, J=4.9, 4.9 Hz, 1H), 5.68 (d, J=7.9 Hz, 2H), 4.11 (br t, J=12.2 Hz, 1H), 3.72-3.67 (m, 8H), 3.58 (tt, J=11.1, 3.9 Hz, 1H), 2.28-2.25 (m, 2H), 2.20-2.17 (m, 2H), 1.86-1.77 (m, 2H), 1.49-1.40 (m, 2H), 1.23 (t, J=7.0 Hz, 3H); $^{31}$P NMR (162 MHz, Deuterium Oxide) δ 0.18; LRMS (M+H) m/z 576.1.

Example 17

LPS Induced IL23p19 in THP-1 Cells (with IFNγ Primed) Assay

Materials and Equipment

THP-1 Cells (ATCC, Cat #TIB-202), Dimethyl Sulfoxide (DMSO) (Sigma-Aldrich, Cat #D2650), RPMI 1640 (Cellgro, Cat #10-040-CM), Fetal Bovine Serum (Sigma, Cat #F4135), Albumin From Bovine Serum (BSA) (Sigma-Aldrich, Cat #A7906), LPS (Serotype K-235, Sigma, Product Number L 2143), IFNγ (Peprotech, Cat #300-02), Capture antibody: Human IL-23p19 ELISA (e-Bioscience, Cat. #14-7238-85), Detection antibody: Primary Mouse Biotinylated anti-human IL-12 (p40/p70) (e-Bioscience, Cat. #13-7129-85), Secondary HRP-conjugated Streptavidin (R&D Systems, Cat #DY998), 1×PBST Washing Buffer (PBS-Tween tablet) (VWR International, Cat #80058-558), ELISA Blocking Buffer (PBS with 1% BSA), ELISA Dilution Buffer (PBS with 1% BSA), 384 Well Flat-Bottom, MaxiSorp Black Immuno Plates (Thermo Scientific, Cat #12-565-346), 384 Well Flat-Bottom, White Tissue Culture Plates (Thermo Scientific, Cat #12-565-343), Super Signal ELISA Pico Chemiluminescent Substrate (Thermo Scientific, Cat #37070), Cell Titer Glo reagent (Promega, Cat #G7573), Positive control, IKK2VI inhibitor (Calbiochem, Cat #401483), AquaMax 4000 plate washer (Molecular Devices), Luminometer, Wallac Victor2 1420 Multilabel Counter.

Method

THP-1 Cells Stimulation:

On day 1, 50K/well THP-1 cells were seeded and primed with IFNγ (50 ng/mL) in 384-well plates for about 18 hours in RPMI media with 10% FBS. On day 2, the compound was serially diluted in DMSO from 5 mM in 3-fold dilutions, and then diluted 1:125 in RPMI media with 10% FBS. 50 μL/well 2× compound was added to 50 μL/well THP-1 cells (with IFNγ primed) in duplicate in 384 well tissue culture plates. The cells were pre-incubated with compound for 1 hour at 37° C., 5% CO₂ before addition of 10 μL/well 11×LPS to give a final concentration of 1 μg/mL LPS. Day 3, after stimulation for 18 hours at 37° C., 5% CO₂, the assay plate was centrifuged and 70 μL/well supernatant was harvested. IL-23p19 protein in 70 μL/well of supernatant was measured by sandwich ELISA, and 25 μl/well Cell Titer Glo reagent was added to the remaining cells to measure compound toxicity.

Human IL-23p19 Sandwich ELISA:

Maxisorp immuno ELISA plates were pre-coated with 25 μL/well of anti-IL-23p19 capture antibody (2.5 ug/mL) in PBS overnight at room temperature. After washing with 1×PBST, the plates were blocked using 100 μL/well of 1% BSA in PBS for 2 hours at room temperature. The plates were washed three times with 1×PBST and 70 μL/well supernatant were added. The plates were incubated at room temperature for 2 hours with shaking and washed three times with 1×PBST. 25 μL/well of biotin labeled anti-IL-12 (p40/p70) detection antibody (100 ng/mL) in PBS with 1% BSA was added and the plates were incubated at room temperature for 2 hours with shaking. After washing three times with 1× PBST, 25 μL/well of streptavidin-HRP (1:200) in PBS with 1% BSA was added and the plates were incubated at room temperature for 20 minutes with shaking. The plates were washed three times with 1× PBST and 25 μL/well of Super Signal ELISA Pico Chemiluminescent Substrate were added. The plates were read with a luminometer, and the chemiluminescence values were entered into Athena (Rigel) for curve fitting, $EC_{50}$ calculation, and database storage. The results are shown in Table 1.

Example 18

Compound Screening Using DC Cells

Materials
　Human PBMC cells (All Cells, Cat No. PB002)
　RPMI growth media containing 10% FBS
　IFNγ (Peprotech, Cat No. 300-02)
　GMCSF (Peprotech, Cat No. 300-03) and IL4 (Peprotech Cat No. 200-04)
　White clear bottom 96 well plates (Fisher, Cat No. 07-200-587, Corning #3903)
　LPS (Make 2.5 mg/ml Stock in PBS) from Sigma Aldrich (Cat No. L2018-5MG)
　Cell Titer Glo reagent (Promega, Cat No. G7573)
　Positive controls, IKK2VI inhibitor (Calbiochem, Cat No. 401483)

Protocol

1. Differentiation of PBMC's to DC Cells:

Human PBMC cells (400 million) obtained from the vendor were transferred into a T-175 flask containing 15 ml RPMI media (10% FBS) and incubate for 2 hours at 37° C. After 2 hours, the media including floating cells was aspirated out carefully and 12 ml of fresh RPMI media (10% FBS) containing GMCSF (100 ng/ml) and IL4 (20 ng/ml) was added, and the flask was kept in a 37° C. incubator for 7 days.

After 3 days, fresh GMCSF (100 ng/ml) and IL4 (20 ng/ml) were added to the flask and the incubation continued. After 7 days, the fully differentiated cells were harvested by spinning down (1200 rpm/5 min) and aspirating the media. The cells were suspended in fresh RPMI media (10% FBS) containing 50 ng/ml IFNγ (1000 U/ml) and then plated (50K/well in 100 μl) onto a white clear bottom 96 well plate and left in a 37° C. incubator for 24 hours.

2. Addition of Compounds:

After 24 hours incubation, 100 μl of RPMI media was added containing 2× concentrated test compound per well to the above cell-culture media (final concentration becomes 1×) and the plates were pre-incubated for 1 hour at 37° C. before stimulating with LPS.

After 1 hour compound pre-incubation, 10 μl per well of 20× concentrated LPS solution in RPMI media was added to give a final concentration of 1 μg/ml. The mixture was shaken and incubated the plates at 37° C. for an additional 18 hours.

155 μl of the supernatant was harvested from each well carefully (without the tip touching the bottom of the well) and to the remaining 50 μl/well of the cell culture plate was added 50 μl of Cell Titer Glo reagent. The mixture was incubated for 1-2 minutes on a shaker and the plate was read for luminescence intensity to determine the compound cytotoxicity. The cell culture supernatant collected above was used to carry out IL23 ELISA (65 μl-Supernatant) and IL10 ELISA (90 μl—Supernatant) as described below.

Example 19

Human IL-23 (p19/p40) ELISA Protocol
(e-Biosciences)

Materials:
　96-well high binding opaque white plates (from Pierce, Cat No. 15042);
　1×PBS; 1×TBST washing buffer;
　Blocking Solution: 0.5% Casein in PBS (from BDH, Cat No. 440203H);
　Dilution Solution: 1% BSA in PBS (10% BSA from Fisher, Cat No. 37525);
　Capture antibody: Rat anti-human IL-23 (p19) (e-Biosciences, Cat. No. 14-7238-85);
　Detection antibody: Primary Mouse Biotinylated anti-human IL-12 (p40/p70) (e-biosciences, Cat No. 13-7129-85);
　Secondary HRP-conjugated Streptavidin (R&D Systems, Cat No. DY998);
　rHuman-IL-23 (e-biosciences, Cat No. 34-8239) (Suggested starting concentration=5 ng/ml in RPMI cell culture media);
　Cell Culture Supernatant (65 μl from THP-1 cells primed with IFNγ (50 ng/ml-1000 U/ml) and stimulated with 0.01% SAC);
　SuperSignal ELISA Pico Chemiluminescent substrate [Pierce, Cat No. 37069].

Coating Plates:

To 10.5 ml PBS add 50 μl of anti-IL23 (p19) was added capture antibody (2.5 μg/ml). The mixture was mixed well and 100 μl of the coating solution was added to each well of the 96 well white plates from Pierce. The wells were covered and incubated overnight at 4° C.

Blocking the Plates:

The anti-IL23 (p19)-antibody-coated plates were washed 2× using TBST (use plate washer) and blocked using 200 μl of 0.5% Casein for 1.5-2 hours at room temperature with shaking.

Addition of Supernatant and Detection:

The plates were washed 2× using TBST and the supernatant was transferred (65 μl/well) to the above pre-blocked/IL23 (p19)-antibody-coated 96 well plate, and incubated at room temperature for 1.5 hours with shaking.

The plates were washed 4× using TBST (plate washer) and 100 μl/well detection antibody solution prepared from 2 μl of biotin labeled anti-IL-12 (p40/p70) antibody in 11 ml 1% BSA/PBS solution (1-5000 dilution) was added. The plates were incubated for 1 hour with shaking at room temperature.

Again, the plates were washed 4× with TBST and 100 μl of HRP labeled Streptavidin (R&D Systems) solution (10 μl/10 ml 1% BSA solution) was added, and the plates were incubated at room temperature for another 45 minutes with shaking.

After 45 minutes, the plates were washed with TBST 4× and 100 ul/well Super Signal ELISA Pico Chemiluminescent Substrate from Pierce (3.5 ml A+3.5 ml B+3.5 ml MQ water) was added. The plates were shaken for 1-2 minutes then read on a plate reader.

Example 20

IRAK4 ADP-Glo Assay

Materials
　IRAK4 Kinase Enzyme (Signalchem, I12-10G-20); 0.1M DTT (Signalchem, D86-09B); MBP Substrate (Signalchem, M42-51N); ADP Glo (Promega, V9101); 1M MgCl$_2$ (Teknova, M03304); 1M Tris-HCl pH7.4 (Teknova, T1074); BSA (Sigma (A3059); Distilled H$_2$O Equipment Wallac Victor2 1420 Multilabel Counter Method The ADP-Glo™ reagents were thawed at ambient temperature. The Kinase Detection Reagent was prepared by mixing kinase detection buffer with the lyophilized kinase detection substrate, and set aside.

A stock volume of 5× Reaction Kinase Buffer was made with a final concentration of 100 mM MgCl$_2$, 200 mM Tris-HCl, and 0.5 mg/ml of BSA, in distilled H$_2$O with a final pH7.4. A 2× working stock volume of Reaction Kinase Buffer was made containing a final concentration of 100 µM DTT.

The components of IRAK4 Enzyme were thawed on ice. Diluted IRAK4 in 1× Kinase Reaction Buffer (diluted from 2× buffer) was prepared at 5.0 ng/l. A 250 µM working stock ATP Assay Solution was prepared in 1× Kinase Reaction Buffer (diluted from 2× buffer).

The compound was diluted in DMSO from 250 M in 4-fold series dilutions for 8 points. Then diluted 1:5 in 2× Reaction Buffer in a 96 well plate. 1.0 µl was transferred to a 384 well plate in duplicate. 2 µl of diluted Active IRAK4 was added (do not add to column 1) and 2× reaction buffer was added to column 1. 1 µl of 1 mg/ml stock solution of MBP substrate was added NOTE: MBP can be combined with ATP mix with equal volume and then added at 2 µl/well. Final reaction volume was 5 µl. The plate was centrifuged and the reaction mixture was incubated at room temperature for 60 minutes or at 30° C. for 30 minutes.

The reaction was terminated and the remaining ATP was depleted by adding 5 µl of ADP-Glo™ Reagent. The 384-well plate was centrifuged and then the reaction mixture was incubated for another 40 minutes at ambient temperature.

10 µl of the Kinase Detection Reagent was added. The plate was centrifuged and then the reaction mixture was incubated for another 30 minutes at ambient temperature.

The 384-well reaction plate was read using the WALLAC plate reader (Luminescence 0.1s).

Example 21

IRAK1 Adapta Assay

Materials

Bar-coded Corning, low volume, white 384-well plate (Corning Cat. #4512)

Test Compounds: The Test Compounds are screened in 1% DMSO (final) in the well. For 10 point titrations, 3-fold serial dilutions 10 µM.

Substrate/Kinase Mixture: The 2×IRAK1/Histone H3 (1-20) peptide mixture is prepared in 50 mM HEPES pH 7.5, 0.01% BRIJ-35, 10 mM MgCl$_2$, 1 mM EGTA.

ATP Solution: All ATP Solutions are diluted to a 4× working concentration in water.

ATP Km apparent is previously determined using a radiometric assay except when no substrate is available in which case an Adapta assay is conducted.

Detection Mix: The Detection Mix is prepared in TR-FRET Dilution Buffer. The Detection mix consists of EDTA (30 mM), Eu-anti-ADP antibody (6 nM) and ADP tracer. The detection mix contains the EC$_{60}$ concentration of tracer for 5-150 µM ATP.

IRAK1 Method 1. 100 nL—100× Test Compound in 100% DMSO
2. 2.4 µL—30 mM HEPES
3. 2.5 µL—4×ATP Solution
4. 5 µL—2× Substrate/Kinase Mixture The final 10 µL Kinase Reaction consists of 3.17-42 ng IRAK1 and 100 µM Histone H3 (1-20) peptide in 32.5 mM HEPES pH 7.5, 0.005% BRIJ-35, 5 mM MgCl$_2$, 0.5 mM EGTA.

5. 30-second plate shake
6. 1-minute centrifuge at 1000× g
7. 60-minute Kinase Reaction incubation at room temperature
8. 5 µL—Detection Mix
9. 30-second plate shake
10. 1-minute centrifuge at 1000× g
11. 60-minute Detection Mix equilibration at room temperature
12. Read on fluorescence plate reader and analyze the data Example 22

IRAK4 Z'-LYTE Assay

Materials

Bar-coded Corning, low volume NBS, black 384-well plate (Corning Cat. #4514)

Test Compounds: The Test Compounds are screened in 1% DMSO (final) in the well. For 10 point titrations, 3-fold serial dilutions are conducted from 10 µM.

Peptide/Kinase Mixture: The 2×IRAK4/Ser/Thr 07 mixture is prepared in 50 mM HEPES pH 7.5, 0.01% BRIJ-35, 10 mM MnCl$_2$, 1 mM EGTA, 2 mM DTT, 0.02% NaN$_3$.

ATP Solution: All ATP Solutions are diluted to a 4× working concentration in Kinase Buffer (50 mM HEPES pH 7.5, 0.01% BRIJ-35, 10 mM MgCl$_2$, 1 mM EGTA). ATP Km apparent is previously determined using a Z-LYTE® assay.

Development Reagent Solution: The Development Reagent is diluted 1:45000 in Development Buffer.

General Method 1. 100 nL—100× Test Compound in 100% DMSO
2. 2.4 L—Kinase buffer
3. 5 µL—2× Peptide/Kinase Mixture
4. 2.5 µL—4×ATP Solution The final 10 µL Kinase Reaction consists of 3.45-63.6 ng IRAK4 and 2 µM Ser/Thr 07 in 50 mM HEPES pH 7.5, 0.01% BRIJ-35, 5 mM MgCl$_2$, 5 mM MnCl$_2$, 1 mM EGTA, 1 mM DTT, 0.01% NaN$_3$.

5. 30-second plate shake
6. 60-minute Kinase Reaction incubation at room temperature
7. 5 µL—Development Reagent Solution
8. 30-second plate shake
9. 60-minute Development Reaction incubation at room temperature
10. Read on fluorescence plate reader and analyze the data Results from the assays are shown in Table 1.

TABLE 1

In vitro results.

| | IL23-p19 ELISA, THP1-IFNy, LPS, 10 pt EC$_{50}$ (μM) | IL23-p19 ELISA, Dendritic, LPS, 10 pt EC$_{50}$ (μM) | IRAK4 ADP-Glo Kinase, 8 pt EC$_{50}$ (μM) | IRAK1 ADP-Glo Kinase, 8 pt EC$_{50}$ (μM) | IRAK4 Z'-LYTE ASSAY EC$_{50}$ (μM) | IRAK1 ADAPTA ASSAY EC$_{50}$ (μM) |
|---|---|---|---|---|---|---|
| I-1 | 0.008 | 0.18 | 0.007 | 0.0081 | 0.006 | 0.004 |
| I-2 | 0.011 | | 0.0464 | 3.909 | | |
| I-3 | 0.0544 | | 0.1284 | 0.0618 | | |
| I-4 | 0.0025 | | 0.0188 | 0.0281 | | |

Example 23

Plasma Protein Binding for I-1

Experimental Procedure

Brain and plasma drug binding were performed by equilibrium dialysis using the Rapid Equilibrium Dialysis (RED) device. Briefly, 300 μL of plasma or brain homogenate (1 brain/3 buffer) containing drug (5 μM) was equilibrated (4-18 h) against 500 μL of buffered saline. After incubation, the concentration of drug in plasma/brain homogenate and buffer was determined by LC-MS/MS.

Recovery Value

Recovery is calculated by determining the total amount of drug in 50 μL of plasma and 50 μL buffer after the incubation and comparing that value to the amount of drug in 50 μL of a plasma sample that was not incubated. For the protein binding assay, drug was added to the plasma and this plasma was added to one side of the dialysis device while buffer was added to the other. After filing the plasma chamber of the equilibrium device, a 50 μL aliquot of plasma was mixed with 50 μL of buffer and then quenched with stop reagent.

Drug recovery=(Drug buffer+Drug plasma)/(drug in initial plasma)

Lower recoveries could result from hydrolysis of drug in plasma (i.e., amide hydrolysis) of loss to binding to apparatus.

Free Drug

Higher free drug in plasma and brain allow for more drug to interact with the target.

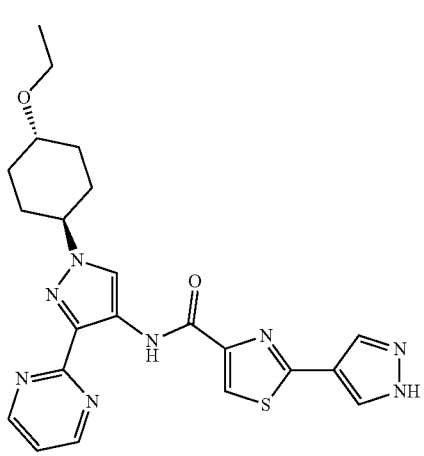

I-1

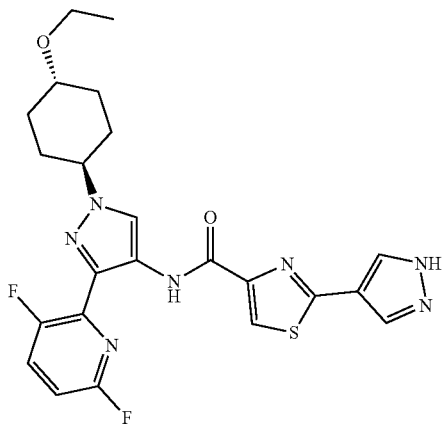

Comparision-1

From a free drug perspective compound I-1 was approximately 6-times more free than Comparison-1 in rat, dog, monkey and human proteins.

Mouse recovery was low due to hydrolysis, which is commensurate with other similar trials in mice.

TABLE 2

Plasma protein binding results

| | Comparision-1 | | I-1 | |
|---|---|---|---|---|
| | % bound | recovery (%) | % bound | recovery (%) |
| Dog | 99.0 | 77.2 | 93.4 | 70.7 |
| Rat | 99.3 | 68.3 | 96.3 | 73.9 |
| Human | 99.6 | 75.5 | 97.0 | 77.1 |
| Monkey | 99.7 | 71.6 | 98.3 | 104* |
| Mouse | 97.8 | 10 | 91.5 | 23.6 |

*result appears to be greater than 100% due to experimental error.

Two runs of rat brain homogenate binding with I-1 compared to Comparison-1. I-1 is approximately 10-fold more free in rat brain than Comparison-1.

Comparison-1 0.102% and 0.114%

I-1 1.06% and 1.43%

Example 24

Whole Blood Assay

Compound I-1 demonstrated similar biochemical potency in in vitro assays to Comparison-1 (See example 23 for the structure of Comparison-1) but I-1 is significantly more potent in cells and in assays conducted in the presence of whole blood.

TABLE 3

In vitro assays

IRAK4 IC$_{50}$ (μM)

| Compound | ADP-Glo (n >= 3) | Z'LYTE (n = 1) | Adapta (n = 1) |
|---|---|---|---|
| I-1 | 0.007 ± 0.004 | 0.006 | 0.004 |
| Comparisoon-1 | 0.006 ± 0.006 | 0.015 | 0.014 |

TABLE 4

Free Fraction in Whole Blood Assay

| Compound | Rat | Human |
|---|---|---|
| I-1 | 3.7% | 3.0% |
| Comparison-1 | 0.7% | 0.4% |

The greater potency of I-1 in whole blood assays is driven by the plasma free fraction. And the free fraction percentage is consistent across species.

To evaluate the effect of compound I-1 on TLR and IL-1R-dependent cytokine release, multiple cell types were isolated and stimulated in the presence of compound I-1 or Comparison-1. The results are provided in Table 5.

TABLE 5

Cell Assays

Cell Assays IC$_{50}$ (μM)

| Compound | IL-23 (LPS, THP-1) | TNFα (PBMC, resiquimod) | TNFα (DC, Gard) | Average |
|---|---|---|---|---|
| I-1 | 0.008 | 0.003 | 0.005 | 0.005 |
| Comparison-1 | 0.063 | 0.015 | 0.019 | 0.032 |

The results obtained in the cell assays above demonstrate that compound I-1 is a potent inhibitor of TLR- and IL-1R-dependent cytokine production in multiple cell types (Table 5). Compound I-1 inhibits TLR4-induced IL-23 and TNF-α production by human THP-1 cells. In human primary dendritic cells (DC), compound I-1 blocks TLR4-induced IL-23 production, TLR7- and TLR2-induced TNF-α production. compound I-1 is also a potent inhibitor of TLR7-dependent cytokine production in human PBMCs and TLR4-dependent one in mouse macrophages. In addition, compound I-1 potently inhibits IL-10-induced production of the cytokine IL-6 in primary human endothelial cells. Compound I-1 broadly inhibits TLR- and IL-1R-dependent pro-inflammatory cytokine production in multiple primary human cell types through inhibition of IRAK1/4 kinase activity. Moreover compound I-1 is a more potent inhibitor of TLR- and IL-1R-dependent signaling in multiple cell types.

Assay Protocol: TLR4 and TLR2 Induced Cytokines in THP-1 Cells.

Materials
  Dimethyl Sulfoxide (DMSO) (Sigma-Aldrich, Cat #D2650)
  Fetal Bovine Serum (Sigma, Cat #F4135)
  RPMI 1640 (Cellgro, Cat #10-040-CM)
  THP-1 (ATCC, Cat #TIB-202)
  Recombinant Human IFN-γ (Peprotech, Cat #AF-300-02)
  Lipopolysaccharides from Escherichia coli K-235 (LPS) (Sigma-Aldrich, Cat #L2018)
  LTA (InvivoGen, Cat No. Tlrl-pslta)
  Anti-Human IL-23p19 (eBioscience, Cat #14-7238-85)
  Biotin Anti-Human IL-12 (p40/70) (eBioscience, Cat #13-7129-85)
  Albumin From Bovine Serum (BSA) (Sigma-Aldrich, Cat #A7906)
  1×PBST Washing Buffer (PBS-Tween tablet) (VWR International, Cat #80058-558)
  ELISA Blocking Buffer (PBS with 2% BSA)
  ELISA Dilution Buffer (0.2% BSA in PBST)
  Human TNF-α DuoSet ELISA Kit (R&D Systems, Cat #DY210)
  CellTiter-Glo® Luminescent Cell Viability Assay (Promega, Cat #G7571)
  96 Well Flat-Bottom, White With ClearBottom, Tissue Culture Plates (Costar 3903)
  96 Well Flat-Bottom, MaxiSorp Black Immuno Plates (Thermo Scientific, Cat #12-566-24)
  Super Signal ELISA Pico Chemiluminescent Substrate (Thermo Scientific, Cat #37070)

Equipment
  Scan Washer 400 plate washer (Molecular Devices)
  Luminometer, Wallac Victor2 1420 Multilabel Counter Method THP-1 cells (100K in 100 μL/well) were primed with 25 ng/mL IFN-γ for 18 hours at 37° C., 5% CO$_2$. Compound was serially diluted in DMSO from 2.5 mM in 4-fold dilutions, and then diluted 1:125 in RPMI 1640 complete media with 10% FBS. 100 μL/well 2× compound was mixed with the 100 μL/well IFN-7 primed THP-1 in 96 well flat-bottom white tissue culture plates. The cells were pre-incubated with compound for 1 hour at 37° C., 5% CO$_2$ and before addition of 10 μL/well 21×LPS to give a final concentration of 1 g/mL for LPS. The cells were stimulated with LPS for 18 hours at 37° C., 5% CO$_2$. After centrifugation, 100 μL/well supernatant was extracted by using a multichannel pipette. IL-23p19 or TNF-α protein in the supernatant were measured by sandwich ELISA. The remaining IFN-7 primed THP-1 cell pellets were used to perform cell viability assays to determine compound cell toxicity. The plates were read with a luminometer, and the chemiluminescence values were entered into Athena (Rigel) for curve fitting, EC$_{50}$ calculation, and database storage.

THP1 cells primed with IFN-7 as previously described were stimulated with LTA (10 μL per well of 20× concentrated LTA solution in RPMI media to give a final concentration of 4 μg/ml) at 37° C., 5% CO$_2$ for an additional 18 hours. The supernatant (155 μL/well) was harvested to measure TNF-α. TNF-α was quantitated by ELISA using Human TNF-α DuoSet ELISA kit following the kit protocol.

Human IL-23p19 Sandwich ELISA:

Maxisorp immuno ELISA plates were pre-coated with 100 μL/well of anti-IL-23p19 capture antibody (2.4 μg/mL) in PBS overnight at room temperature. After washing with 1×PBST, the plates were blocked using 300 μL/well of 1% BSA in PBS for 2 hours at room temperature. The plates were washed three times with 1×PBST and 100 μL/well supernatant was added. The plates were incubated at room temperature for 2 hours with shaking. The plates were washed three times with 1×PBST and 100 μL/well of biotin anti-human IL-12 (p40/70) detection antibody (10 ng/mL) in PBS with 0.1% BSA were added. The plates were incubated at room temperature for 2 hours with shaking. The plates were washed three times with 1×PBST and 100 μL/well streptavidin-HRP (1:200) in PBS with 0.1% BSA was added. The plates were incubated at room temperature for 20 minutes with shaking. The plates were washed three times with 1×PBST and 100 μL/well of Super Signal ELISA Pico Chemiluminescent Substrate were added. The plates were read with a luminometer, and the chemiluminescence values were entered into Athena (Rigel) for curve fitting, $EC_{50}$ calculation, and database storage.

Assay Protocol: TLR7-Induced TNF-α in Human Peripheral Blood Mononuclear Cells (PBMC).

Materials

Corning™ Costar™ 96-Well, Cell Culture-Treated, U-Shaped-Bottom Microplate (Fisher, Cat #07-200-95)
Human PBMC (ALL Cells, Cat #PB002)
Resiquimod (InvivoGen, Cat No. Tlrl-r848)
Human TNF-α DuoSet ELISA Kit (R&D Systems, Cat #DY210)
Recombinant Human IFN-α (Peprotech, Cat #300-02BC)
RPMI with 10% FBS
Axygen 96well, 1.1 mL, sterile (VWR International, Cat #47734-788)

Method

Human peripheral blood mononuclear cells (PBMC) were seeded at 100,000 cells per well in 100 μL of RPMI with 10% FCS and primed overnight with 8 ng/ml of IFN-β at 37° C., 5% $CO_2$. Compound was serially diluted in DMSO from 2 mM in 3-fold dilutions, and then diluted 1:100 in RPMI 1640 complete media with 10% FBS (2× stock). The PBMCs were pre-incubated with test compound for 1 hour at 37° C., 5% $CO_2$ by adding 100 μL of RPMI media containing 2× concentrated test compound per well (0.5% final DMSO concentration).

Resiquimod Stimulation:

The PBMCs were stimulated with resiquimod (10 μL per well of 21× concentrated resiquimod solution in RPMI media to give a final concentration of 0.1 μg/ml) at 37° C., 5% $CO_2$ for an additional 18 hours. 100 μL of supernatant per well was harvested to measure TNF-α. TNF-α was quantitated using DuoSet ELISA Kit per manufacturer's protocol.

Assay Protocol: TLR-Induced Cytokines in Human Primary Monocyte-Derived Dendritic Cells (DC).

Materials

Dimethyl Sulfoxide (DMSO) (Sigma-Aldrich, Cat #D2650)
Fetal Bovine Serum (Sigma, Cat #F4135)
Human PBMC cells (All Cells, Cat No. PB002)
RPMI growth media containing 10% FBS
IFN-7 (Peprotech, Cat No. 300-02)
GMCSF (Peprotech, Cat No. 300-03) and IL4 (Peprotech Cat No. 200-04)
White clear bottom 96 well plates (Fisher, Cat No. 07-200-587, Corning #3903)
LPS (Make 2.5 mg/ml Stock in PBS) from Sigma Aldrich (Cat No. L2018-5MG)
Lipopolysaccharides from Escherichia coli K-235 (LPS) (Sigma-Aldrich, Cat #L2018)
Gardiquimod NEW Imidazoquinoline compound (Invivo-Gen, Cat #tlrl-gdqs)
Anti-Human IL-23p19 (eBioscience, Cat #14-7238-85)
Biotin Anti-Human IL-12 (p40/70) (eBioscience, Cat #13-7129-85)
Albumin From Bovine Serum (BSA) (Sigma-Aldrich, Cat #A7906)
1×PBST Washing Buffer (PBS-Tween tablet) (VWR International, Cat #80058-558)
ELISA Blocking Buffer (PBS with 2% BSA)
ELISA Dilution Buffer (0.2% BSA in PBST)
Human TNF-α DuoSet ELISA Kit (R&D Systems, Cat #DY210)
Cell Titer Glo reagent (Promega, Cat No. G7573)
Positive controls, IKK2VI inhibitor (Calbiochem, Cat No. 401483)

Equipment

Scan Washer 400 plate washer (Molecular Devices)
Luminometer, Wallac Victor2 1420 Multilabel Counter Method Differentiation and IFNγ-Priming of Dendritic Cells:

Human peripheral blood mononuclear cells (PBMC) (400 million) were allowed to adhere in a T-175 flask containing 15 ml RPMI media (10% FBS) for 2 hours at 37° C., 5% $CO_2$ to capture the monocytes.

After 2 hours, the media including floating cells was carefully removed and 12 ml of fresh RPMI media (10% FBS) containing GM-CSF (100 ng/ml) and IL-4 (20 ng/ml) were added to the adherent monocytes. The monocytes were allowed to differentiate for 7 days at 37° C., 5% $CO_2$ for 7 days, supplementing with fresh GM-CSF and IL-4 after 3 days.

The differentiated dendritic cells (DC) were harvested by centrifugation (1200 rpm/5 min). The DCs were primed at 37° C., 5% $CO_2$ for 24 hours with 50 ng/ml IFN-7 (1000 U/ml) at 50K/well in 100 μL/well of fresh RPMI media (10% FBS) in a white clear bottom 96 well plate.

Compound Pre-Incubation:

Compound was serially diluted in DMSO from 2.5 mM in 4-fold dilutions, and then diluted 1:125 in RPMI 1640 complete media with 10% FBS. The primed DCs were pre-incubated with test compound for 1 hour at 37° C., 5% $CO_2$ by adding 100 μl of RPMI media containing 2× concentrated test compound per well (0.5% final DMSO concentration).

Lps Stimulation:

The DCs were stimulated with LPS (10 μL per well of 20× concentrated LPS solution in RPMI media to give a final concentration of 1 μg/ml) at 37° C., 5% $CO_2$ for an additional 18 hours.

The supernatant (155 μl/well) was harvested to measure IL-23 by ELISA (65 μL-Supernatant). Cell Titer Glo reagent (50 μL/well) was added to the remaining 50 μL/well of the cell culture plate, incubated for 1-2 minutes on a shaker and the plate was read for luminescence intensity to determine the compound cytotoxicity. The chemiluminescence values were entered into Athena (Rigel) for curve fitting, $EC_{50}$ calculation, and database storage.

Gardiquimod Stimulation:

The DCs were stimulated with gardiquimod (10 μL per well of 20× concentrated gardiquimod solution in RPMI media to give a final concentration of 4 μg/ml) at 37° C., 5% $CO_2$ for an additional 18 hours. The supernatant (155 μL/well) was harvested to measure TNF-α. TNF-α was quantitated by ELISA, following the kit protocol.

Whole Blood Assay:

To assess the effect of whole blood on the potency of compound I-1 and Comparison-1, the compounds were evaluated for their inhibitory potential on TLR dependent cytokine release in human blood. Freshly drawn peripheral blood from healthy volunteers was incubated with test compound and stimulated overnight with LPS or Gardiquimod. The serum was isolated after centrifugation and TNF-α and IL-6 were measured by ELISA. The results are shown in Table 6.

Assay Protocol: LPS Induced TNF-α in Human Blood.
Materials
  RPMI 1640 (Cellgro, Cat #10-040-CM)
  Fetal Bovine Serum (Sigma, Cat #F4135)
  Lipopolysaccharides from Escherichia coli K-235 (Sigma-Aldrich Chemicals Cat #L2018-5MG)
  BD Vacutainer Sodium Heparin Tube (BD Cat #4191982)
  96-Well Polystyrene Plates (Fisher Cat #12-565-500)
  Dimethyl Sulfoxide (DMSO) (Sigma-Aldrich, Cat #D2650)
  Human Cytokine MAGNETIC Panel: Magnetic (EMD Millipore Corp. Cat #HCYTOMAG-60K-02)
Equipment
  Luminex Flexmap 3d.
Method
Whole blood of healthy volunteers was collected in Vacutainer containing Sodium Heparin and plate 40 μL of blood to each well. Compound was serially diluted in DMSO from 2 mM in 3-fold dilutions, and then diluted 1:100 in media with 10% FBS. 50 μL of 2× compound was added per well in duplicate to each well and incubate for one hour. 10 μL LPS was added to each well at a final concentration of 0.5 ng/ml and allow cells to incubate overnight.

100 μL of PBS was added to each well and centrifuged for 10 minutes at 1000 RPM. 25 μL of supernatant were taken, and TNF-α was measured on Luminex Flexmap 3d.

Assay Protocol: Gardiquimod-Induced IL-6 in Human Blood Induced TNF-α in Human Blood.
Materials
  RPMI 1640 (Cellgro, Cat #10-040-CM)
  Fetal Bovine Serum (Sigma, Cat #F4135)
  Gardiquimod (InvivoGen Cat #tlrl-gdqs)
  BD Vacutainer Sodium Heparin Tube (BD Cat #4191982)
  96-Well Polystyrene Plates (Fisher Cat #12-565-500)
  Dimethyl Sulfoxide (DMSO) (Sigma-Aldrich, Cat #D2650)
  Human Cytokine MAGNETIC Panel: 116 Magnetic (EMD Millipore Corp. Cat #HCYTOMAG-60K-02)
Equipment
  Luminex Flexmap 3d.
Method
Whole blood of healthy volunteers was collected in Vacutainer containing Sodium Heparin and 40 μL of blood was plated to each well. Compound was serially diluted in DMSO from 2 mM in 3-fold dilutions, and then diluted 1:100 in media with 10% FBS. 50 μL of 2× compound per well in duplicate was added and incubated for one hour. 10 μL Gardiquimod was added to each well at a final concentration of 4 μg/ml and cells were incubated overnight.

100 μL of PBS was added to each well and centrifuged for 10 minutes at 1000 RPM 25 μL of supernatant were taken, and IL-6 was measured by Luminex Flexmap 3d.

TABLE 6

| | Human Whole Blood Assays | | |
|---|---|---|---|
| | Human Whole Blood Assays (IC50$_{50}$) (μM) | | |
| Compound | IL-6 Gard | TNFα LPS | Average |
| I-1 | 0.124 | 0.224 | 0.174 |
| Comparison-1 | 1.400 | 1.399 | 1.400 |

Compound I-1 demonstrates greater potency in blocking inflammatory signaling in cell-based assays and loses less potency than Comparison-1 when tested in the presence of human whole blood.

Example 25

Prodrug Compound I-3

TABLE 7

| Bioavailability of Compound I-3 | |
|---|---|
| Species | Bioavailability (% F) of Compound I-3 |
| Mouse | 34 |
| Rat | 12 |
| Monkey | 71 |
| Dog | 53 |

The bioavailability of compound I-3 was measured as the amount of the parent compound I-1 that was detected, thereby demonstrating that compound I-3 acts as a prodrug of I-1 in vivo.

In view of the many possible embodiments to which the principles of the disclosed technology may be applied, it should be recognized that the illustrated embodiments are only preferred examples of the technology and should not be taken as limiting the scope of the technology. Rather, the scope of the technology is defined by the following claims. We therefore claim as our technology all that comes within the scope and spirit of these claims.

We claim:
1. A compound having a structure according to Formula I

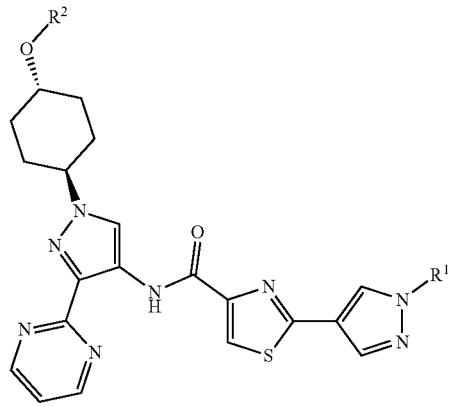

Formula I or a pharmaceutically acceptable salt or solvate thereof, wherein:
  $R^1$ is H, aliphatic, or alkyl phosphate;
  $R^2$ is $C_{1-6}$alkyl.
2. The compound of claim 1, wherein $R^1$ is H, alkyl, or -alkylOP(O)(OR)$_2$, where each OR is —OH, —Oalkyl, —Oaryl, —Oheteroaryl, —Oaralkyl, or —OM$^+$ where M$^+$ is a counter ion with a single positive charge.
3. The compound of claim 2, wherein $R^1$ is —CH(CH$_3$)OP(O)(OR)$_2$ or —CH$_2$OP(O)(OR)$_2$.
4. The compound of claim 1, wherein $R^2$ is $C_{1-4}$alkyl.
5. The compound of claim 1, wherein the compound has a structure according to Formula II Formula II

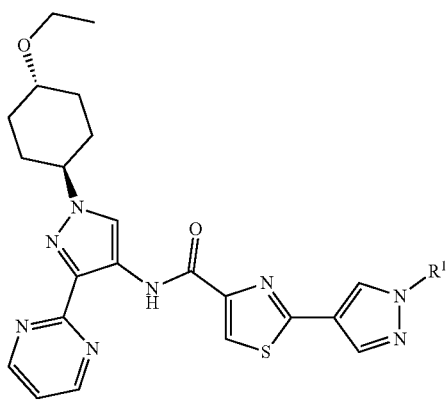

or a pharmaceutically acceptable salt or solvate thereof.

6. The compound of claim 5, wherein R¹ is wherein R¹ is H or $C_{1-4}$alkyl phosphate.

7. The compound of claim 5, wherein R¹ is —CH₂OP(O)(OH)₂, —CH(CH₃)OP(O)(OH)₂, or a pharmaceutically acceptable salt thereof.

8. The compound of claim 1, wherein R¹ is H, or $C_{1-4}$alkyl phosphate.

9. The compound of claim 2, wherein R¹ is —CH₂OP(O)(OR)₂.

10. The compound of claim 9, wherein:
R¹ is —CH₂OP(O)(OH)₂;
R¹ is —CH₂OP(O) (OC$_{1-6}$alkyl)₂; or
R¹ is —CH₂OP(O) (O⁻M⁺)₂.

11. The compound of claim 10, wherein R¹ is —CH₂OP(O)(O⁻Na⁺)₂.

12. The compound of claim 1, wherein the compound is a salt co-crystal.

13. The compound of claim 1, wherein the compound is in a free base form.

14. The compound of claim 12, wherein the salt co-crystal is a tartaric acid salt co-crystal or a tris salt co-crystal.

15. The compound of claim 1, selected from:
I-1: N-(1-((1r,4r)-4-ethoxycyclohexyl)-3-(pyrimidin-2-yl)-1H-pyrazol-4-yl)-2-(1H-pyrazol-4-yl) thiazole-4-carboxamide;
I-2: (4-(4-((1-((1r,4r)-4-ethoxycyclohexyl)-3-(pyrimidin-2-yl)-1H-pyrazol-4-yl) carbamoyl) thiazol-2-yl)-1H-pyrazol-1-yl)methyl dihydrogen phosphate;
I-3: sodium (4-(4-((1-((1r,4r)-4-ethoxycyclohexyl)-3-(pyrimidin-2-yl)-1H-pyrazol-4-yl) carbamoyl) thiazol-2-yl)-1H-pyrazol-1-yl)methyl phosphate;
I-4: N-(1-((1r,4r)-4-ethoxycyclohexyl)-3-(pyrimidin-2-yl)-1H-pyrazol-4-yl)-2-(1H-pyrazol-4-yl) thiazole-4-carboxamide tartaric acid salt;
I-5: (4-(4-((1-((1r,4r)-4-ethoxycyclohexyl)-3-(pyrimidin-2-yl)-1H-pyrazol-4-yl) carbamoyl) thiazol-2-yl)-1H-pyrazol-1-yl)methyl hydrogen phosphate 1,3-dihydroxy-2-(hydroxymethyl) propan-2-aminium (tris salt);
I-6:1-(4-(4-((1-((1r,4r)-4-ethoxycyclohexyl)-3-(pyrimidin-2-yl)-1H-pyrazol-4-yl) carbamoyl) thiazol-2-yl)-1H-pyrazol-1-yl)ethyl dihydrogen phosphate;
I-7: sodium 1-(4-(4-((1-((1r,4r)-4-ethoxycyclohexyl)-3-(pyrimidin-2-yl)-1H-pyrazol-4-yl) carbamoyl) thiazol-2-yl)-1H-pyrazol-1-yl)ethyl phosphate; and
I-8:1-(4-(4-((1-((1r,4r)-4-ethoxycyclohexyl)-3-(pyrimidin-2-yl)-1H-pyrazol-4-yl) carbamoyl) thiazol-2-yl)-1H-pyrazol-1-yl)ethyl hydrogen phosphate 1,3-dihydroxy-2-(hydroxymethyl) propan-2-aminium (tris salt).

16. The compound of claim 15, wherein the compound is I-1: N-(1-((1r,4r)-4-ethoxycyclohexyl)-3-(pyrimidin-2-yl)-1H-pyrazol-4-yl)-2-(1H-pyrazol-4-yl) thiazole-4-carboxamide.

17. The compound of claim 15, wherein the compound is I-2: (4-(4-((1-((1r,4r)-4-ethoxycyclohexyl)-3-(pyrimidin-2-yl)-1H-pyrazol-4-yl) carbamoyl) thiazol-2-yl)-1H-pyrazol-1-yl)methyl dihydrogen phosphate.

18. The compound of claim 15, wherein the compound is I-3: sodium (4-(4-((1-((1r,4r)-4-ethoxycyclohexyl)-3-(pyrimidin-2-yl)-1H-pyrazol-4-yl) carbamoyl) thiazol-2-yl)-1H-pyrazol-1-yl)methyl phosphate.

19. A compound that is I-1: N-(1-((1r,4r)-4-ethoxycyclohexyl)-3-(pyrimidin-2-yl)-1H-pyrazol-4-yl)-2-(1H-pyrazol-4-yl) thiazole-4-carboxamide or a pharmaceutically acceptable salt or solvate thereof.

20. A pharmaceutical composition comprising a compound according to claim 1, and a pharmaceutically acceptable excipient.

21. A pharmaceutical composition, comprising:
a means for delivering an IRAK inhibitory moiety, wherein the IRAK inhibitory moiety comprises the compound of claim 1; and
a pharmaceutically acceptable excipient.

22. The pharmaceutical composition of claim 21, wherein the means for delivering an IRAK inhibitory moiety comprises a means for inhibiting an IRAK protein in vivo.

* * * * *